US007070974B1

(12) United States Patent
Desgroseillers et al.

(10) Patent No.: US 7,070,974 B1
(45) Date of Patent: Jul. 4, 2006

(54) METALLOPROTEASES OF THE NEPRILYSIN FAMILY

(75) Inventors: Luc Desgroseillers, St-Basile-le-Grand (CA); Guy Boileau, Brossard (CA)

(73) Assignee: Universite de Montreal, Montreal (CA)

( * ) Notice: Subject to any disclaimer, the term of this patent is extended or adjusted under 35 U.S.C. 154(b) by 0 days.

(21) Appl. No.: 09/913,329

(22) PCT Filed: Feb. 11, 2000

(86) PCT No.: PCT/CA00/00147

§ 371 (c)(1),
(2), (4) Date: Aug. 21, 2001

(87) PCT Pub. No.: WO00/47750

PCT Pub. Date: Aug. 17, 2000

(30) Foreign Application Priority Data

Feb. 11, 1999  (CA)  .................................... 2260376

(51) Int. Cl.
 C12N 9/48   (2006.01)
 C12N 1/20   (2006.01)
 C12N 15/00  (2006.01)
 C12Q 1/37   (2006.01)
 C07H 21/04  (2006.01)

(52) U.S. Cl. ................................ 435/212; 435/4; 435/6; 435/252.3; 435/320.1; 435/69.1; 435/71.1; 435/440; 435/24; 536/23.2; 536/23.5

(58) Field of Classification Search ................ 435/183, 435/252.3, 320.1, 4, 71.1, 212, 440, 6, 69.1; 536/23.2, 23.1, 23.5; 530/350
See application file for complete search history.

(56) References Cited

U.S. PATENT DOCUMENTS 5,688,640 A    11/1997  Yanagisawa
5,817,482 A *  10/1998  Bandman et al. .......... 435/69.1

FOREIGN PATENT DOCUMENTS

WO    WO 99/53077    10/1999

OTHER PUBLICATIONS

Marra et al. EST database—Accession # AA146423. 1996.*

(Continued)

Primary Examiner—Manjunath Rao
Assistant Examiner—Yong Pak
(74) Attorney, Agent, or Firm—Nixon & Vanderhye

(57) ABSTRACT

In this paper, we describe RT-PCR strategies that allowed us to identify and clone members of the NEP-like family. Degenerate oligoncleotide primers corresponding to consensus sequences located on either side of the HEXXH consensus sequence for zincins were designed and used in RT-PCR with mouse and human testis cDNAs. DNA fragments with lengths expected from the sequence of this class of enzympes were obtained. These DNA fragments were cloned and sequenced. Using this PCR strategy and the PCR fragments as probes to screen cDNA libraries, three zincin-like peptidases were identified in addition of known members of the family. The cDNA sequences allowed to derive specific probes for Northern and in situ hybridization, and probe human chromosomes to localize the gene and establish potential links to genetic diseases. Furthermore, these cDNA sequences were used to produce recombinant fusion proteins in *Escherichia coli* in order to raise specific antibodies. Finally, the cDNA sequences were cloned in mammalian expression vectors and transfected in various mammalian cell lines to produce active recombinant enzymes suitable for testing specific inhibitors.

6 Claims, 22 Drawing Sheets

OTHER PUBLICATIONS

Scott et al, "Molecular cloning, expression and chromosomal localization . . . ," Gene, vol. 174, pp. 135-143 (1996).

Hooper, N., "Families of zinc metalloproteases," FEBS Letters 354, pp. 1-6 (1994).

Ikeda et al, "Molecular Identification and Characterization. . . ," The Journal of Biological Chemistry, vol. 274, No. 45, pp. 32469-32477 (1999).

Valdenaire et al, "XCE, a new member of the endothelin. . . ," Molecular Brain Research, vol. 64, pp. 211-221 (1999).

Lipman et al, "Cloning of Human PEXcDNA," The Journal of Biological Chemistry, vol. 273, No. 22, pp. 13729-13737 (1998).

Devault et al., "Expression of Neutral Endopeptidase. . . ," The Journal of Biological Chemistry, vol. 263, No. 8, pp. 4033-4040.

Lemay et al, "Fusion of a Cleavable Signal Peptide. . . ," The Journal of Biological Chemistry, vol. 264, No. 26, pp. 15620-15623.

Korth et al, "Construction, expression and characterization of. . . ," FEBS Letters 417, pp. 365-370 (1997).

Helene et al, "Effects of Monoclonal Antibodies Raised. . . ," Biochemical Pharmacology, vol. 43, No. 4, pp. 809-814 (1992).

Fenton et al, "Long-Term Culture of Disaggregated Rat. . . ," Journal of Cellular Physiology, vol. 155, pp. 1-7 (1993).

Valdenaire, "Home sapiens mRNA for XCE protein"; EMBL database — Accession +Y16187 whole document (1999).

* cited by examiner

```
                  1         10            20                    30
       NEP1-HU    MGK.......SESQMDITDINT..PKPKKQRWTPLEI............SLSVLVLLL
                   *              +       *          *                    +
       PEX-HUM    MEA.......ETG....SSVET..GKKANRGTRIALVV............FVGGTLVLG
                   ++                *         *                         + +
       KELL-HU    MEGGDQSEEEPRERSQAGGMGTLWSQESTPEERLPVEGSRPWAV....ARRVLTAILIL.
                   *                  *            + + ++                 *
       ECE1-HU    MSTYKRATLDEEDLVDSLSEGDAYPNGLQVNFHSPRSGQRCWAARTQVEKRLVVLVVLLA consens    M                  T             P                    L 40        50          60         70         80         90
       NEP1-HU    TIIAVTMIALYA.TYDD...GICKSSDCIKSAARLIQNMDATTEPCTDFFKYACGGWLKR
                   ++          +        *     ++  ++        ++   ++   ++   ++
       PEX-HUM    TILFLVSQGLLSLQAKQ...EYCLKPECIEAAAAILSKVNLSVDPCDNFFRFACDGWISN
                   *  +     ++   *       +   *      +  + ++  ++  ++   +  +++
       KELL-HU    .GLLLCFSVLLFYNFQNCGPRPCETSVCLDLRDHYLASGNTSVAPCTDFFSFACG...RA
                   ++  +  +    +  +       + ++     *    +  + ++  ++++ +++    +
       ECE1-HU    AGLVACLAALGI.QYQTRSPSVCLSEACVSVTSSILSSMDPTVDPCHDFFSYACGGWIKA consens       L        L          C        C         L    V PC DFF  ACGGW 100        110        120        130        140        150
       NEP1-HU    NVIPETSSRYGNFDILRDELEVVLKDVLQEP..KTEDIVAVQKAKALYRSCINESAIDSR
                   + ***    *   ++ +     ++    +++++           ++  ++  ++   ++
       PEX-HUM    NPIPEDMPSYGVYPWLRHNVDLKLKELLEKSISRRRDTEAIQKAKILYSSCMNEKAIEKA
                    *       +     *   ++   + + ++                 ++  ++   +++
       KELL-HU    KETNNS......FQELATKNKNRLRRILEVQ.NSWHPGSGEEKAFQFYNSCMDTLAIEAA
                    *  +       -       +     + ++   ++                ++  ++ +
       ECE1-HU    NPVPDGHSRWGTFSNLWEHNQAIIKHLLENS.TA.SVSEAERKAQVYYRACMNETRIEEL consens    N  P       G F L         LK  LE           A KA  Y SCMNE AIE 160        170        180        190        200
       NEP1-HU    GGEPLLKLLPDI.YGWP..VATENWEQKYGAS.WTAEKAIAQLNSKYGKKVLINLFVGTD
                     ***  ++      ++           ++                   +   +  + +
       PEX-HUM    DAKPLLHILRHSPFRWPVLESNIGPEGVWSERKFSLLQTLATFRGQYSNSVFIRLYVSPD
                   ++                                  +   ++     ++     *   *
       KELL-HU    GTGPLRQVIEEL........GGWRISGKWTSLNFN..RTLRLLMSQYGHFPFFRAYLGPH
                    ++   ++  +         *** + + ++ ++     ++   ++  ++  +  +++  +
       ECE1-HU    RAKPLMELIERL........GGWNITGPWAKDNFQ..DTLQVVTAHYRTSPFFSVYVSAD consens      PL                 G W   F          TL     Y     F   YV  D 220        230        240        250        260
       NEP1-HU    DKNSVNHVIHIDQPRLGLPSR.DYYECTGIYKEACTAYVDFMISVARLIRQEERLPI.DE
                   *+  +     *  + ++    +  ++                +    ++  *  *     -
       PEX-HUM    DKASNEHILKLDQATLSLAVREDYLDHSTEAKSYRDALYKFMVDTAVL......LGA.NS
                   ++        +                                    +               +   +-
       KELL-HU    PASPHTPVIQIDQPEFDVPLKQDQEQKI.YAQIFRE.YLTYLNQLGTL......LGG.DP
                   +++  -+    +         +      +        ++   +++ +       +++ *
       ECE1-HU    SKNSNSNVIQVDQSGLGLPSRDYYLNKTENEKVLTG.YLNYMVQLGKL......LGGGDE consens    K S   VI DQ  L LP R DY        K      Y  M   L      LG  D
```

FIG. 1

```
         270       280       290       300       310       320
NEP1-HU  NQLALEMNKVMELEKEIANATAKPEDRNDPMLLYNKMTLAQIQNNFSLEINGKPFSWLNF
          +   +    ++   ++    + +         +++                 +   *
PEX-HUM  SRAEHDMKSVLRLEIKIAEIMIPHENRTSEAMY.NKMNISELSAMIP......QFDWLGY
          *         *  * **              **  *             ***
KELL-HU  SKVQEHSSLSISITSRLFQFLRPLEQRRAQGKLFQMVTIDQLKEMAP......AIDWLSC
           +      +    + ++         **   *   **           ** * **
ECE1-HU  EAIRPQMQQILDFETALANITIPQEKRRDEELIYHKVTAAELQTLAP......AINWLPF
consens          M       E   A       PER             KT L        WL 330       340       350       360       370       380
NEP1-HU  TNEIMSTVNISITNEEDVVVYA....PEYLTKLKPILTKYSARDLQNLMSWRFIMDLVSS
              *                      + +   + ++          ++     **
PEX-HUM  IKKVIDTRLYPHLKDISPSENVVVRVPQYFKDLFRILGSERKKTIANYLVWRMVYSRIPN
                                                *            *    +
KELL-HU  LQATFTPMSLSPSQSLVVHDVEYL...KNMSQLVEEMLLKQRDFLQSHMILGLVVTLSPA
            + *    + ++ + ***      +         +  *   + ** **      +
ECE1-HU  LNTIFYPVEINESEPIVVYDKEYL...EQISTLIMT...TDRCLLNNYMIWNLVRKTSSF
consens                V              L              L N M W  V 390       400       410       420       430
NEP1-HU  LSRTYKESR....NAFRKALYGTT.SETATWRRCANYVNGNMENAVGRLYVEAAFAGESK
         ***            +   +++      + +          ++    *  *  *     *
PEX-HUM  LSRRFQYRW....LEFSRVIQGTT.TLLPQWDKCVNFIESALPYVVGKMFVDVYFQEDKK
          +   **                   *  * ***      ++     ** *
KELL-HU  LDSQFQEARRKLSQKLRELTEQPPMPARPRWMKCVEETGTFFEPTLAALFVREAFGPSTR
         ++  ++ +        +  +            +++ ++ +      +   **   *
ECE1-HU  LDQRFQDA....DEKFMEVMYGTKKTCLPRWKFCVSDTENNLGFALGPMFVKATFAEDSK
consens  L   FQ       F        GT     P W   CV           G FV  F  K 440       450       460       470       480       490
NEP1-HU  HVVEDLIAQIREVFIQTLD.DLTWMDAETKKRAEEKALAIKERIGYPDDIVSNDNKLNNE
           *       +   ++  +   ++++  *+   * +++ +       +++    +
PEX-HUM  EMMEELVEGVRWAFIDMLEKENEWMDAGTKRKAKEKARAVLAKVGYPE.FIMNDTHVNED
           +   +   +  +  *   + ++          + *      *    +       *
KELL-HU  SAAMKLFTAIRDALITRLR.NLPWMNEETCNMAQDKVAQLQVEMGASE.WALKPELARQE
          * +    *     +  +      * +++         *  ++      +
ECE1-HU  SIATEIILEIKKAFEESLS.TLKWMDEETRKSAKEKADAIYNMIGYPN.FIMDPKELDKV
                 (4)    ┌──────────────────┐
consens    L    IR AFI │  L  L WMD ET     │  A EKA A     GYP
                      └─(1A/B)────────────▷

500       510       520       530       540       550
NEP1-HU  YLELNYKEDEYFENIIQNLKFSQSKQLKKLREKVDKEWISGAAVVNAFYSSGRNQ┌IVFP
          + ** *    * *  *  * +  *+    *  ** +  +  +  ******  ++│ * **
PEX-HUM  LKAIKFSEADYFGNVLQTRKYLAQSDFFWLRKAVPKTEWFTNPTTVNAFYSASTNQ│IRFP
                  **   +                    +   *  +** ++ +    ++
KELL-HU  YND.IQLGSSFLQSVLSCVRSLRARIVQSFLQPHPQHRWKVSPWDVNAYYSVSDHV│VFP
          ++                                         +  ******   │***
ECE1-HU  FNDYTAVPDLYFENAMRFFNFSWRVTADQLRKAPNRDQWSMTPPMVNAYYSPTKNE│IVFP
                                                           (2A/B)├──
consens          YF N              LR          W   P  VNA YS  N │IVFP
```

FIG. 1 (cont'd)

```
             560       570       580       590       600       610
NEP1-HU  AGILQPPFFSAQQ.SNSLNYGGIGMVIGHEITHGFDDNGRNFNKDGDLVDWWTQQSASNF
         ** ** +++     ++  ++  ++   +++ +++++ +++   +   +  **    *    *
PEX-HUM  AGELQKPFFWGTEYPRSLSYGAIGVIVGHEFTHGFDNNGRKYDKNGNLDPWWSTESEEKF
         ** ** ++      ++      ++ ++  ++  +  +           +    *
KELL-HU  AGLLQPPFFHPGY.PRAVNFGAAGSIMAHELLHIFYQL...LLPGGCL.....ACDNHAL
         ** ** ++     * * +++  *   +++ +++  +       + +           +
ECE1-HU  AGILQAPFYTRSS.PKALNFGGIGVVVGHELTHAFDDQGREYDKDGNLRPWWKNSSVEAF
         ──────▷
consens  AG LQ PFF      P  LN G IG  GHE TH FD  GR   K G L WW   S    F 620       630       640       650       660       670
NEP1-HU  KEQSQCMVYQYGNFSWDLAGGQHLNGINTLGENIADNGGLGQAYRAYQNYI..KKNG.EE
         ++    ++    ++ **   +    +   +++|*********|+ +++    +   + ++
PEX-HUM  KEKTKCMINQYSNYYWK.KAGLNVKGKRTLGENIADNGGLREAFRAYRKWINDRRQGLEE
         +      +     *                 |++ ++ +++|+  ++       +    +
KELL-HU  QEAHLCLKRHYAAF..PLPSRTSFNDSLTFLENAADVGGLAIALQAYSKRL..LRHH.GE
         +      +              *         |++ ** +++|+ ++  *        +
ECE1-HU  KRQTECMVEQYSNY..SVNG.EPVNGRHTLGENIADNGGLKAAYRAYQNWV..KKNG.AE
                                          ◁─────(3)
consens  KE  CM QY N         NG   TLGENIADNGGL A RAY          G E 680       690       700       710       720       730
NEP1-HU  KLLPGLDLNHKQLFFLNFAQVWCGTYRPEYAVNSIKTDVHSPGNFRIIGTLQNSAEFSEA
         ++++   *****   + + *  ++++  *       ++  ++ +     +  + ++   *
PEX-HUM  PLLPGITFTNNQLFFLSYAHVRCNSYRPEAAREQVQIGAHSPPQFRVNGAISNFEEFQKA
         ++     + +- +++  + +  *             +++* ++ +      *
KELL-HU  TVLPSLDLSPQQIFFRSYAQVMCRKPSPQDSH.....DTHSPPHLRVHGPLSSTPAFARY
         *+ + +     *  ++  +++ +  *  *         + +++ ++ +  ++    +
ECE1-HU  HSLPTLGLTNNQLFFLGFAQVWCSVRTPESSHEGLITDPHSPSRFRVIGSLSNSKEFSEH
consens    LP L L  QLFFL AQV C    PE       D HSP  FRV G LSN  EF 740       750
NEP1-HU  FHCRKNSYMNPEKK.CRVW
         +   ++ ++ +|+    ++ *
PEX-HUM  FNCPPNSTMNRGMDSCRLW
         ++    ++ +|+       - ++
KELL-HU  FRCARGALLNPSSR.CQLW
         +++   *   +|++    +    +
ECE1-HU  FRCPPGSPMNPPHK.CEVW
                    ◁────(5)
consens  F C   S MNP   C W
```

FIG. 1 (cont'd)

| PRIMER | SEQUENCE |
|---|---|
| (1A) | 5'-TGGATGGAT/CGA/CIGG/A1ACIA/CA-3' |
| (1B) | 5'-TGGATGGAT/CGA/CIGG/A1ACIA/CG-3' |
| (2A) | 5'-A/GT1GT1TT/CCCIGCIGG1A/GT/A1C/TTA/TCA-3' |
| (2B) | 5'-A/GT1GT1TT/CCCIGCIGG1A/GT/A1C/T1G/CCA-3' |
| (3) | 5'-A11CCICC1A/TC/TA/GTCIGCIG/AC/TA/GT1T/CTC-3' |
| (4) | 5'-GAT/CAAT/CT/CT1GAT/CGAA/GT/CT1AAT/CTGGATGG-3' |
| (5) | 5'-T/CT/CACCA1A/TCT/GA/GCATCG/TT/CTTCAT1GGG/ATG-3' |

FIG. 2

Sequence of NL-1 cDNA from mouse

```
ctgcctactccaccggagccacctggccagctccacccaaccctggacattcaagacttgcctagcactgactgagagcaccaggtcctgtgacctcaccagctcag
agaccaggacagtgcaccaccagctcagtgtgtcctaggcatccagtgccttctcccagcctgcctgggggcttagcgtgcctgtgcctcaccagaaccggctgatcaggaaagcctgaaggccagtgggg
                                                                                                        cgggaggccagcagccgctgtgacctcaccagctcag
```

|     |  |  |  |  |  |  |  |  |  |  |  |  |  |  |  |  |  |  |  |  |     |
|----:|--|--|--|--|--|--|--|--|--|--|--|--|--|--|--|--|--|--|--|--|----:|
|     | met | val | glu | arg | ala | gly | trp | cys | arg | lys | lys | ser | pro | gly | phe | val | glu | tyr | gly | leu | met | val | leu | leu | leu | leu | gly | ala | 30 |
|   1 | ATG | GTG | GAG | AGA | GCA | GGC | TGG | TGT | CGG | AAG | AAG | TCC | CCA | GGC | TTC | GTG | GAG | TAT | GGG | CTG | ATG | GTG | CTG | CTG | TTG | CTG | GGA | GCC | 60 |
|     | ile | val | thr | leu | gly | val | phe | tyr | ser | ile | gly | lys | ile | gln | leu | pro | leu | leu | thr | ser | gln | his | phe | ser | trp | asp | glu | arg | thr | val |
|  91 | ATA | GTC | ACT | CTG | GGT | GTC | TTC | TAC | AGC | ATA | GGG | AAG | ATA | CAG | CTG | CCC | CTC | TTA | ACT | AGC | CAG | CAC | TTC | TCC | TGG | GAT | GAG | AGG | ACG | GTT | 90 |
|     | val | lys | arg | ala | leu | arg | asp | ser | ser | leu | lys | ser | asp | ile | cys | val | thr | pro | ser | cys | val | ile | ala | ala | arg | ile | leu | glu | asn |
| 181 | GTA | AAA | CGA | GCC | CTC | AGG | GAT | TCA | AGT | CTG | AAA | TCA | GAT | ATC | TGC | GTG | ACC | CCA | AGC | TGT | GTG | ATA | GCA | GCT | AGA | ATC | CTC | GAA | AAC | 120 |
|     | met | asp | gln | ser | arg | asn | pro | cys | glu | asn | phe | tyr | gln | tyr | ala | cys | gly | trp | leu | arg | his | his | val | ile | pro | glu | thr | asn | ser |
| 271 | ATG | GAC | CAA | TCG | AGG | AAC | CCC | TGT | GAA | AAC | TTC | TAC | CAG | TAC | GCC | TGC | GGC | TGG | CTG | AGG | CAC | CAC | GTG | ATC | CCA | GAG | ACC | AAC | TCC | 150 |
|     | arg | tyr | ser | val | phe | asp | ile | leu | arg | leu | glu | leu | val | gly | leu | lys | ile | ser | val | asp | ser | thr | ser | gln | his | arg | pro | ala |
| 361 | CGA | TAC | AGC | GTC | TTT | GAC | ATC | CTG | CGG | CTG | GAG | CTG | GTG | GGG | CTC | AAA | ATC | AGT | GTG | GAC | AGT | ACT | TCC | CAG | CAT | CGC | CCG | GCC | 180 |
|     | val | glu | lys | ala | thr | lys | lys | ile | glu | ser | val | met | gln | asn | glu | ile | asp | ser | arg | asp | pro | leu | glu | gln | leu | ala | val | leu | lys |
| 451 | GTG | GAG | AAG | GCC | ACA | AAG | AAG | ATC | GAG | AGT | GTG | ATG | CAA | AAT | GAG | ATC | GAC | TCT | AGA | GAC | CCG | CTG | GAG | CAG | TTG | GCT | GTC | TTA | AAA | 210 |
|     | met | val | gly | gly | trp | pro | val | ala | met | asp | lys | trp | asn | glu | thr | met | gly | leu | glu | trp | glu | leu | glu | arg | gln | leu | ala | val | ile | tyr | ile | leu | asn |
| 541 | ATG | GTA | GGA | GGT | TGG | CCT | GTG | GCC | ATG | GAT | AAG | TGG | AAT | GAG | ACC | ATG | GGC | CTC | GAG | TGG | GAA | CTG | GAG | CGA | CAG | TTG | GCT | GTC | ATC | TAC | ATA | TTA | GAC | AAC | 240 |
|     | ser | gln | phe | asn | arg | val | leu | ile | leu | phe | arg | gln | asn | asp | gln | asn | ser | ser | arg | gln | asn | his | lys | val | arg | his | asn | his | lys | gln | gln | gln | gln | pro |
| 631 | TCG | CAG | TTC | AAC | AGG | GTC | CTC | ATC | CTC | TTC | AGA | CAG | AAT | GAC | CAG | AAT | TCC | AGC | AGG | CAG | AAT | CAT | AAG | GTA | CGG | CAC | AAC | CAC | AAG | CAG | CAG | CAG | CAG | CCC | 270 |
|     | thr | leu | gly | met | pro | ser | arg | phe | tyr | tyr | glu | gln | glu | asp | asn | his | lys | val | arg | lys | ala | tyr | leu | glu | phe | met | thr | ser | val |
| 721 | ACC | TTG | GGC | ATG | CCA | TCC | CGG | TTC | TAT | TAC | GAG | CAG | GAG | GAC | AAC | CAC | AAG | GTA | CGG | AAA | GCC | TAC | CTG | GAG | TTC | ATG | ACG | TCA | GTG |

FIG. 3

|     |     | ala | thr | met | leu | arg | lys | asp | gln | asn | leu | ser | lys | glu | ser | ala | met | val | arg | glu | glu | met | ala | glu | val | leu | glu | leu | glu | thr | his |
| --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| 811 |     | GCC | ACT | ATG | CTT | AGG | AAA | GAC | CAG | AAC | CTG | TCC | AAG | GAG | AGC | GCC | ATG | GTG | CGG | GAG | GAG | ATG | GCG | GAG | GTG | CTG | GAA | CTG | GAG | ACG | CAT |
|     |     |     |     |     |     |     |     |     |     |     |     |     |     |     |     |     |     |     |     |     |     |     |     |     |     |     |     |     |     |     | 330 |
|     |     | leu | ala | asn | ala | thr | val | pro | gln | lys | arg | his | asp | val | thr | ala | met | val | tyr | his | arg | glu | met | asp | leu | glu | leu | gln | glu | arg | phe |
| 901 |     | CTG | GCC | AAC | GCC | ACA | GTC | CCC | CAG | AAA | AGG | CAT | GAT | GTC | ACT | GCC | ATG | GTG | TAC | CAC | CGA | GAG | ATG | GAC | CTG | GAG | CTA | CAG | GAA | AGG | TTT |
|     |     |     |     |     |     |     |     |     |     |     |     |     |     |     |     |     |     |     |     |     |     |     |     |     |     |     |     |     |     |     | 360 |
|     |     | gly | leu | lys | gly | phe | asn | trp | thr | leu | phe | ile | gln | asn | val | leu | ser | ser | ala | met | val | glu | val | leu | phe | pro | asp | tyr | leu | val | val |
| 991 |     | GGT | CTG | AAG | GGG | TTT | AAC | TGG | ACT | CTC | TTC | ATA | CAA | AAC | GTG | TTG | TCT | TCT | GCC | ATG | GTG | GAA | GTC | CTG | TTC | CCA | GAT | TAC | CTG | GTG | GTG |
|     |     |     |     |     |     |     |     |     |     |     |     |     |     |     |     |     |     |     |     |     |     |     |     |     |     |     |     |     |     |     | 390 |
|     |     | tyr | gly | ile | pro | tyr | ile | gly | asn | leu | glu | asn | leu | ile | ile | asp | ser | tyr | ser | ala | arg | thr | met | gln | asn | tyr | leu | val | trp | arg | leu |
| 1081|     | TAC | GGC | ATC | CCC | TAC | ATT | GGC | AAT | CTG | GAG | AAT | CTG | ATT | ATT | GAT | AGC | TAC | AGC | GCA | CGA | ACC | ATG | CAG | AAC | TAC | CTG | GTA | TGG | CGC | CTG |
|     |     |     |     |     |     |     |     |     |     |     |     |     |     |     |     |     |     |     |     |     |     |     |     |     |     |     |     |     |     |     | 420 |
|     |     | leu | asp | arg | ile | ser | gly | ser | leu | ser | gln | arg | phe | lys | arg | ala | arg | val | asp | tyr | arg | lys | ala | leu | tyr | gly | thr | thr | val | gln | glu | val |
| 1171|     | CTA | GAT | CGA | ATT | GGC | AGC | AGC | CTG | AGC | CAG | AGA | TTC | AAA | AGA | GCG | CGT | GTG | GAC | TAC | CGC | AAG | GCG | CTG | TAC | GGC | ACG | ACC | GTG | GAG | GTA |
|     |     |     |     |     |     |     |     |     |     |     |     |     |     |     |     |     |     |     |     |     |     |     |     |     |     |     |     |     |     |     | 450 |
|     |     | arg | trp | arg | glu | cys | val | ser | asn | ser | asn | met | glu | met | ala | val | gly | ser | leu | tyr | ile | lys | ser | lys | glu | ala | phe | ser | lys | asp | ser |
| 1261|     | CGC | TGG | CGA | GAG | TGT | GTC | AGC | AAC | AGT | AAC | ATG | GAG | ATG | GCC | GTG | GGG | TCC | CTC | TAC | ATC | AAG | TCC | AAG | GAA | GCC | TTC | TCC | AAG | GAC | AGC |
|     |     |     |     |     |     |     |     |     |     |     |     |     |     |     |     |     |     |     |     |     |     |     |     |     |     |     |     |     |     |     | 480 |
|     |     | lys | ser | thr | val | arg | glu | glu | leu | lys | ile | arg | ile | val | phe | val | ser | arg | ile | leu | asn | leu | asp | met | trp | asp | glu | glu | ser | lys |
| 1351|     | AAG | AGC | ACG | GTC | AGA | GAG | GAG | CTG | AAG | ATA | CGG | ATT | GTG | TTT | GTC | TCC | AGG | ATA | CTG | AAC | CTG | GAT | ATG | TGG | GAC | GAA | GAA | TCC | AAG |
|     |     |     |     |     |     |     |     |     |     |     |     |     |     |     |     |     |     |     |     |     |     |     |     |     |     |     |     |     |     |     | 510 |
|     |     | lys | lys | ala | gln | glu | lys | glu | met | asn | ile | arg | glu | glu | asp | asn | asn | ala | gln | arg | his | leu | asp | glu |
| 1441|     | AAG | AAG | GCC | CAG | GAA | AAG | GAA | ATG | AAT | ATA | CGG | GAA | GAG | GAT | AAC | AAT | GCC | CAG | AGG | CAC | CTG | GAT | GAG |
|     |     |     |     |     |     |     |     |     |     |     |     |     |     |     |     |     |     |     |     |     |     |     |     |     |     |     |     |     |     |     | 540 |
|     |     | glu | tyr | ser | ser | leu | thr | phe | phe | gln | asp | leu | tyr | glu | asn | gly | leu | gln | asn | leu | lys | ser | arg | leu | lys |
| 1531|     | GAA | TAC | TCC | AGT | TTG | ACT | TTC | TTC | CAG | GAC | CTG | TAT | GAG | AAT | GGA | CTT | CAG | AAC | CTC | AAG | AGC | AGG | CTC | AAG |
|     |     |     |     |     |     |     |     |     |     |     |     |     |     |     |     |     |     |     |     |     |     |     |     |     |     |     |     |     |     |     | 570 |
|     |     | leu | arg | glu | lys | val | asp | gln | leu | asn | ala | phe | tyr | ser | pro | asn | arg | asn | gln | ile | val | phe |
| 1621|     | CTT | CGG | GAA | AAG | GTG | GAC | CAG | CTC | AAT | GCA | TTC | TAC | TCC | CCA | AAC | AGA | AAC | CAG | ATC | GTC | TTT |

FIG. 3 (cont'd)

```
                                                                                                                              600
      pro ala gly ile leu gln pro pro phe phe ser lys asp gln pro gln ser leu asn phe gly gly ile gly met val ile gly his glu
1711  CCA GCA GGG ATT CTC CAG CCG CCC TTC TTC AGC AAG GAC CAA CCA CAG TCC TTG AAT TTT GGG GGC ATC GGG ATG GTG ATT GGG CAC GAG
                                                                                                                              630
      ile thr his gly phe asp asp asn ile tyr gln arg asn gly asp lys asp phe leu asp trp trp ser ser asn phe ser ala arg his phe
1801  ATC ACA CAC GGC TTT GAT GAT AAT ATC TAT CAG CGT AAC GGT GAC AAG GAC TTT GAC CTG ATG TGG TGG AGT TCG GCC CGG CAC TTC
                                                                                                                              660
      gln gln ser gln cys met arg tyr gly asn phe ser trp glu leu ala asp asn val asn gln asn gly phe ser thr leu
1891  CAA CAG TCG CAA TGC ATG CGA TAC GGC AAC TTC TCT TGG GAA CTA ATG GCA GAC AAT GTG AAC CAG AAT GGA TTC AGT ACC CTC
                                                                                                                              690
      gly glu asn ile ala asp asn gly gly val arg gln ala tyr leu arg trp leu ala asp gly lys gly gln arg leu
1981  GGG GAG AAC ATT GCC GAC AAC GGA GGT GTG CGA CAG GCA TAC CTG CGA TGG CTG GCT GAT GGC AAA GGT CAG CGA CTG
                                                                                                                              720
      pro gly leu asn thr tyr ala gln leu phe ile asn tyr ala gln val trp cys gly ser tyr arg pro glu phe ala val gln
2071  CCG GGA CTG AAC ACC TAT GCC CAG CTT TTC ATC AAC TAT GCC CAG GTG TGT GGT TCC TAT AGG CCG GAG TTC GCC GTC CAG
                                                                                                                              750
      ser ile lys thr asp val his ser pro leu lys tyr arg val leu gly ser leu gln asn leu pro gly phe ser glu ala phe his cys
2161  TCC ATC AAG ACG GAC GTC CAC AGT CCT CTT AAG TAC AGG GTG CTG GGC TCA CTA CAG AAC CTG CCA GGC TTC TCT GAG GCA TTC CAC TGC
                                                                                                                              765
      pro arg gly ser pro met his pro lys met arg cys arg ile trp ***
2251  CCA CGA GGC AGC CCC ATG CAC CCC AAG ATG CGA TGT CGC ATC TGG TAG  CCAAGGCTGAGCTATGCTGCGGCCACGCCCGCCACCCGGCGGATGAGTGGTGCCGGTC
2354  CTGCGCCCCCCTCAGGCCAGTGAGGTCAGCCAGGAAGAGCAGTCAGCCCTGCCTTCCACCCTCTCCATAGTGTGTGGCTAAATGTTCTCGAGCTTCAGACTTGAGCTAAGTAAACGC
2473  CTGCGCCCCCCTCAGGCCAGTGAGGTCAGCCAGGAAGAGCAGTCAGCCCTGCCTTCCACCCTCTCCATAGTGTGTGGCTAAATGTTCTCGAGCTTCAGACTTGAGCTAAGTAAACGC
2925  TTC
```

FIG. 3 (cont'd)

Sequence of NL-2 cDNA from humans

```
                met val glu ser ala gly arg ala gly gln lys arg ala gly phe leu glu gly leu leu leu leu leu leu val thr        28
  1 GTG GGG ATC GTG GAG AGC GCC GGC CGT GCA GGG AAG CGC GCA GGG TTC CTG GAG GGG CTG CTG CTG CTG CTG CTG GTG ACC                 58
    ala ala leu val ala leu gly val leu tyr ala asp arg arg arg gly ala arg leu pro arg leu cys phe leu gln glu
 91 GCT GCC CTG GTG GCC TTG GGT GTC CTC TAC GCC GAC CGC CGC AGA GGG GCA CGG CTT CCA CGG CTG TGC TTC TTA CAG GAG                  88
    glu arg thr phe val lys arg lys pro arg pro arg gly ile pro ala val ser glu gln val cys thr thr pro gly cys val ile ala    118
181 GAG AGG ACC TTT GTA AAA CGA AAA CCC CGA CCC CGA GGG ATC CCA GCC GTG AGC GAG CAG GTG TGC ACC ACC CCT GGC TGC GTG ATA GCA
    ala ala arg ile leu gln asn met asp thr glu thr pro cys asp phe gln gly ala cys gly gly trp leu arg arg his                148
271 GCC GCC AGG ATC CTC CAG AAC ATG GAC ACG GAA CCG TGT GAT TTT CAG GGC GCA TGC GGA GGC TGG CTG CGG CGG CAC
    val ile pro glu ile asn thr arg ser arg tyr arg asp val leu arg thr arg val ile leu lys lys ala leu glu leu asn ser        178
361 GTG ATC CCT GAG ATC AAC ACC AGA TCA AGA TAC AGA GAC GTC CTC CGC ACG AGA GTG ATC CTC AAA AAG GCG CTG GAG CTG AAT TCG
    thr ala lys asp arg pro ala pro val glu thr tyr leu ala arg met cys gln ser met asn gln ile glu arg lys arg gly ser gln    208
451 ACT GCC AAG GAC CGG CCG GCT CCC GTG GAG ACG TAC CTG GCG ATG TGT CAG AGT ATG AAT CAG ATA GAG AGA AAG CGA GGC TCT CAG
    pro leu asp leu asp ile leu glu val gly val gly trp pro val leu ile thr trp asn asp gln asn ser ser glu leu glu            238
541 CCC CTG GAC CTG GAC ATC TTG GAG GTG GGT GTG GGA TGG CCG GTG CTG ATC ACC TGG AAC GAC CAG AAC TCC AGC GAG GAG CTG
    arg gln leu ala leu met ser asn phe gln ala val leu asp phe tyr asn asn lys lys val arg arg his                            268
631 CGG CAG CTG GCG ATG TCA AAC TTC CAG GCC CGC AGG CGC GTC CTC TTC TAC AAC AAC AAG AAG GTG CGG GAA CAC
    ile ile tyr ile asp gln pro thr pro met gly tyr tyr glu asp ala asn arg gly ser asn arg lys val arg glu ala tyr            298
721 ATC ATC TAC ATA GAC CAG CCC ACC CCC ATG GGC TAC TAC GAG GAT GCA AAC CGG GGC AGC AAC CGG AAA GTG CGG GAA GCC TAC
    leu gln phe met val ser val ala thr leu leu arg asn leu asp glu arg pro cys leu val gln glu asp met val gln                328
811 CTG CAG TTC ATG GTG TCA GTG GCC ACG TTG CTG CGA AAC CTG GAT GAG CGG CCC TGC CTG GTG CAG GAG GAC ATG GTG CAG
```

FIG. 4

```
 901 val leu glu leu thr gln leu ala lys ala thr val pro gln glu arg his asp val ile ala leu tyr his arg met gly leu
     GTT CTG GAG CTG ACA CAG CTG GCC AAG GCC ACG GTA CCC CAG GAG AGA CAC GAC GTC ATC GCC TTG TAC CAC CGG ATG GGA CTG  358

991 glu glu leu gln ser gln phe gly leu lys gly asn trp thr leu gln thr val leu ser ser val lys ile lys leu leu
     GAG GAG CTG CAA AGC CAG TTT GGC CTG AAG GGA AAC TGG ACT CTG CAA ACT GTG CTA TCC TCT GTC AAA ATC AAG CTG CTG  388

1081 pro asp glu val val gly leu pro tyr gly ile pro tyr leu gln asn leu ile ile asp thr ser ala thr ile gln asn
     CCA GAT GAA GTG GTG GGC CTG CCC ATC CCC TAC CTG CAG AAC CTT ATC ATC GAA ACC TAC TCA GCC ACC ATA CAG  418

1171 tyr leu val trp arg leu val leu gly ser leu ser gln arg phe arg val asn tyr arg lys ala leu phe
     TAC CTG GTC TGG CGC CTG GTG CTG GGT AGC CTA AGC CAG AGA TTC AGA GAC CAG AAC TAC CGC AAG GCG CTG TTT  448

1261 gly thr met val glu glu val arg trp arg glu cys val gly tyr val asn ser asn met glu asn ala val gly ser leu tyr val arg
     GGC ACA ATG GTG GAG GAG GTG CGC TGG CGT GAA TGT GTG GGC TAC GTC AAC AGC AAC ATG GAG AAC GCC GTG GGC TCC CTC TAC GTC AGG  478

1351 glu ala phe pro gly ser lys ser met val arg glu leu ile asp lys val arg thr val phe val glu thr ile leu asp gly glu leu gly
     GAG GCG TTC CCT GGA AGC AAG AGC ATG GTC AGA GAA CTG ATT GAC AAG GTG CGG ACA GTG TTT GTG GAG ACG ATC CTG GAC GGG GAG CTG GGC  508

1441 trp met asp glu glu ser lys lys lys ala gln glu lys ile arg gln ile met ser ile ala met ser glu asp tyr ile leu glu glu
     TGG ATG GAC GAG GAG TCC AAG AAG AAG GCC CAG GAG AAG ATC CGG CAG ATC ATG AGC ATC GCC ATG AGT GAG GAC TAC ATC CTG GAG GAG  538

1531 met asn arg arg leu asp glu tyr ser asn leu asn phe ser gln glu leu tyr phe glu asn ser leu gln asn leu lys val gly
     ATG AAC CGC AGG CTG GAC GAG TAC TCC AAT CTG AAT TTC TCA CAG GAG CTG TAC TTT GAG AAC AGT CTG CAG AAC CTC AAG GTG GGC  568

1621 ala gln arg leu ser arg lys val asp pro asn leu trp ile ile gly ala ala val val asn ala phe tyr ser pro
     GCC CAG CGG AGC CTC AGG AAG GTG GAC CCA AAT CTC TGG ATC ATC GGG GCG GCG GTC GTC AAT GCG TTC TAC TCC CCA  598

1711 asn arg asn gln val phe ile leu gln pro pro phe ser phe ala gly ile leu asn phe gly gly ile
     AAC CGA AAC CAG GTA ATT TTC CTT CAG CCC CCC TTC TTC AGC TTT GCC GGG ATC CTG AAC TTT GGA GGC ATT  628
```

FIG. 4 (cont'd)

|      |     |     |     |     |     |     |     |     |     |     |     |     |     |     |     |
|------|-----|-----|-----|-----|-----|-----|-----|-----|-----|-----|-----|-----|-----|-----|-----|
|      | gly | met | val | ile | gly | his | glu | ile | thr | his | gly | phe | asp | asn | gly | arg | asn | phe | asp | lys | asn | gly | asn | met | met | asp | trp | ser |
| 1801 | GGG | ATG | GTG | ATC | GGG | CAC | GAG | ATC | ACG | CAC | GGC | TTT | GAC | AAT | GGC | CGG | AAC | TTC | GAC | AAG | AAT | GGC | AAC | ATG | ATG | GAT | TGG | AGT |
|      |     |     |     |     |     |     |     |     |     |     |     |     |     |     |     |     |     |     |     |     |     |     |     |     |     |     |     | 658 |
|      | asn | phe | ser | thr | gln | his | phe | arg | ser | glu | cys | met | ile | tyr | gln | tyr | asn | tyr | ser | trp | asp | leu | ala | asp | glu | gln | asn |
| 1891 | AAC | TTC | TCC | ACC | CAG | CAC | TTC | CGC | TCA | GAG | TGC | ATG | ATC | TAC | CAG | TAC | AAC | TAC | TCC | TGG | GAC | CTG | GCA | GAC | GAA | CAG | AAC |
|      |     |     |     |     |     |     |     |     |     |     |     |     |     |     |     |     |     |     |     |     |     |     |     |     |     |     | 688 |
|      | val | asn | gly | phe | asn | thr | gly | glu | asn | ile | ala | asp | gln | ala | tyr | lys | tyr | ala | gln | val | trp | leu | lys | trp | met | ala | glu |
| 1981 | GTG | AAC | GGA | TTC | AAC | ACC | GGG | GAA | AAC | ATT | GCT | GAC | CAA | GCC | TAT | AAG | TAC | GCC | CAG | GTG | TGG | CTC | AAG | TGG | ATG | GCA | GAG |
|      |     |     |     |     |     |     |     |     |     |     |     |     |     |     |     |     |     |     |     |     |     |     |     |     |     |     | 718 |
|      | gly | gly | lys | asp | gln | gln | pro | gly | leu | asp | phe | thr | his | ile | asn | phe | phe | arg | tyr | lys | trp | cys | gly | ser | tyr |
| 2071 | GGT | GGC | AAG | GAC | CAG | CAG | CCC | GGT | CTC | GAT | CTC | ACC | CAT | GAG | TTC | TTC | ATC | AGC | TAT | AAG | TGG | TGC | GGG | TCC | TAC |
|      |     |     |     |     |     |     |     |     |     |     |     |     |     |     |     |     |     |     |     |     |     |     |     |     | 748 |
|      | arg | pro | glu | phe | ala | ile | ser | gln | thr | asp | val | his | ser | pro | leu | lys | tyr | arg | val | leu | gly | ser | leu | gln | asn | leu | ala | ala |
| 2161 | CGG | CCC | GAG | TTC | GCC | ATC | TCC | CAA | ACA | GAC | GTC | CAC | AGT | CCC | CTG | AAG | TAC | AGG | GTA | CTG | GGG | TCG | CTG | CAG | AAC | CTG | GCC | GCC |
|      |     |     |     |     |     |     |     |     |     |     |     |     |     |     |     |     |     |     |     |     |     |     |     |     |     |     |     | 770 |
|      | phe | ala | asp | thr | phe | his | cys | ala | arg | gly | thr | pro | met | his | pro | lys | glu | arg | cys | arg | val | trp | ter |
| 2251 | TTC | GCA | GAC | ACG | TTC | CAC | TGT | GCC | CGC | GGC | ACC | CCC | ATG | CAC | CCC | AAG | GAG | CGA | TGC | CGT | GTG | TGG | TAG | CCA | AGG | CCC | TGC | CGC | GCT | GTG |
| 2341 | CGG | CCC | ACG | TCT | GTG | CGA | AGG | GCA | TCT | GTG | CGA | AGG | GCA | TCT | GTG | CGA | CCC | AGT | CGT | CCC | GCC | AAC | CAT | GCC |

| 2341 | CGG | CCC | ACG | TCT | GTG | CGA | AGG | GCA | TCT | GTG | CGA | CCC | AGT | CGT | CCC | GCC | AAC | CAT | GCC |
| 2431 | AAG | CCT | GCC | TGC | CAG | GGC | CCT | GGC | TGG | AGC | CTG | CAC | CTG | AGC | CTG | AGC | CAG | GTA | GCA | GTG | TCC | AGT | GCA | GTA | CCT | GGA |
| 2521 | CCG | GAG | CCC | TCA | CAG | ACA | CCC | GGG | CTC | AGT | GCC | CCC | GTC | ACA | ACT | CTG | TAG | TCC | TGC | CCA | CCC | TTC | AAG |
| 2611 | GTG | CAT | TGT | CTT | CCA | GTA | TCT | ACA | GCT | TCA | GAA | CTT | GAG | CTA | CAG | AAA | TGC | TTT | CAA | AGA | AGA | AAA | AAA |

FIG. 4 (cont'd)

Sequence of NL-3 cDNA from human

```
   1 GGC GCT GGG AGA CAC CGG ACG CCC GCT CGG CTG CGC TGC GGC TCA GGC CCC TCG CGG CCC GGC GCT CGG CCG GCC CAG GCG
  91 CGG ACC TGC CGG CTG CGG CCC CAG GGC CAT GGC GAG GCC GAG GAG GCC CAC GCG GGC CAC GTA GCC CAT CCC CAG GTG GCC CAG GTC
                                                                                                                          22
 181 met glu pro pro tyr ser leu thr ala his tyr asp glu phe gln val lys tyr val ser arg
     ATG GAG CCC CCG TAT TCG ACG GCG CAC TAC GAT GAG TTC CAA GAG GTC AAG TAC GTG AGC CGC
                                                                                          52
 271 cys gly ala gly gly ala ser leu pro pro leu gly phe pro pro leu ala ala ser ala ala arg thr gly ala arg ser gly leu
     TGC GGC GCC GGG GGC GCC TCC CTG CCG CCC CTG GGC TTC CCG CCG TTG GCC GCC AGC GCC GCG CGC ACC GGG GCC CGG TCC GGG CTG
                                                                                                                          82
 361 cys val glu arg arg trp asn arg pro pro phe pro pro phe leu leu ser gly gly ala ala ile leu ala ala met leu ala leu
     TGC GTG GAG CGC CGG TGG AAC CGG CCC CCC TTC CCG CCG TTC CTG CTG TCG GGG GGC GCC GCC ATT CTG GCT GCT ATG CTG GCC CTC
                                                                                                                         112
 451 lys tyr leu gly pro val ala gly gly cys cys pro gly glu arg lys gln gly lys ala phe ala arg ala ala arg phe leu
     AAG TAC CTG GGC CCG GTC GCC GGG GGC TGT TGT CCT GAG CGC AAG CAA GGC AAG GCG TTC GCG CGC GCT GCC CGC TTC CTG
                                                                                                                 142
 541 ala ala asn leu asp ser ile asp pro cys gln asp phe tyr ser phe ala cys gly gly trp leu arg arg his ala ile pro asp
     GCC GCC AAC CTC GAC AGC ATC GAC CCA TGC CAG GAC TTC TAC TCG TTC GCC TGC GGC GGT TGG CTG CGG CGC CAC GCC ATC CCC GAC
                                                                                                                         172
 631 asp lys leu thr tyr gly thr ile ala ala ala ile glu gln asn asn glu glu leu ala arg leu leu ala arg pro gly gly pro
     GAC AAG CTC ACC TAT GGC ACC ATC GCA GCG GCC ATC GAG CAA AAC GAG GAG CTA CGG CTG CTG GCG CGG CCC GGG GGT CCT
                                                                                                                 202
 721 gly gly ala ala gln gln lys arg val ala phe phe arg ala phe phe arg ser cys met arg asp met arg pro met leu
     GGG GGC GCC GCA CAG CAG AAG CGC GTG GTG GTG GCC TTC TTC CGC GCC TTC TTC CGC AGC TGC ATG CGC GAC ATG CGA CCC ATG CTA
                                                                                                                         232
 811 glu ile glu gly cys gly pro leu pro asp trp asp val ala ala arg leu arg asp leu asn arg leu leu
     GAG ATC GAG GGG TGC GGC CCG CTG CCG GAC TGG GAC GTC GCG GCG CGA CGG TGG GAC CTC AAC CGG CTG CTG
                                                                                                  262
 901 tyr lys ala gln gly val tyr phe ser leu val thr ala asp asp pro ala ser arg tyr ala arg val ile arg
     TAC AAG GCG CAG GGC GTG TAC TTC TCG GTC ACC GTC CTG GAC GAC CCT GCC TCC AGG TAC GTC ATC CGC
                                                                                                  292
 991 ile asp asp gly leu gly leu pro glu arg thr leu tyr leu ala gln asp glu lys ser glu val leu ala tyr arg val
     ATT GAT GAT GGG CTG GGT CTG CCA GAG AGG ACC CTG TAC CTG GCT CAG GAT GAG AAG AGT GAG GTC CTG GCA TAC AGG GTG
                                                                                                                 322
1081 phe met glu val ser leu ala asp ala val val lys gln ile leu val glu leu gln gln leu ala asn
     TTC ATG GAG GTG CGA GTG GCT GCA GAC GCT GGT AAG CAG CAG ATC CTG GAA CAG CAG CTG GCC AAC
```

FIG. 5

```
      ile thr val ser glu tyr asp asp leu arg arg asp val ser ser met tyr asn lys val thr leu gly gln leu gln lys ile thr pro     352
1171  ATC ACT GTG TCA GAG TAT GAC GAC CTA CGG CGA GAT GTC AGC TCC ATG TAC AAC AAG GTG ACG CTG GGG CAG CTG CAG AAG ATC ACC CCC     382
      his leu arg trp lys trp leu asp leu phe gln ile phe gln glu glu ser phe val leu val val leu ala thr leu ala thr asp tyr met
1261  CAC TTG CGG TGG AAG TGG CTA GAC CTG TTC CAG ATC TTC CAG GAG GAG TCA TTC GTC CTG GTG GTG CTG GCG ACA CTG GCT GAC TAC ATG     412
      gln gln val ser gln leu ile leu his arg pro his pro thr asn tyr leu val trp arg tyr gln gly ser asp lys pro gln glu his     442
1351  CAG CAG GTG TCG CAG CTC ATC CTG CAC CGG CCA CAC CCC ACA AAC TAC CTG GTG TGG CGC TAC CAG GGC AGC GAC AAG CCA CAG GAG CAC     442
      leu ser pro pro phe arg val leu his glu ala gln glu met gly ser asp lys pro gln glu his leu ala arg val cys leu
1441  CTG TCC CCG CCA TTC CGT GAG GTG CTG CAC GAG GCA CAG GAG ATG GGC AGC GAC AAG CCA GAG CAC CTG GCC CGG GTC TGC TTG     472
      gly gln ala asn arg his phe gly met ala leu gly ala leu phe val his glu leu phe gly ala leu ala ser lys ala lys val gln gln
1531  GGC CAG GCC AAT CGC CAC TTT GGC ATG GCC CTC GGC GCC CTC TTT GTA CAT GAG CTC TTC GGC GCC CTC GCC AGC AAA GCC AAG GTG CAG CAG     502
      leu val glu asp ile lys tyr ile leu gly gln arg leu glu glu leu asp trp met asp ala glu phe glu val his glu
1621  CTA GTG GAA GAC ATC AAG TAC ATC CTG GGC CAG CGC CTG GAG GAG CTG GAC TGG ATG GAC GCC GAG AAG TTT GAG GTC CAT GAG     532
      leu gln tyr met met val met val gly tyr pro asp leu lys pro phe leu leu lys ala val asp lys val lys ile arg gln val asp lys val lys pro thr     562
1711  CTC CAG TAC ATG ATG GTG ATG GTC GGC TAC CCC GAT GCT GTG GAC AAG TAT AAG GAG TTT AAG CGG GAC GTG AAG TCC ACG     592
      lys thr tyr phe lys asn ile leu asn ser ile arg phe asp ile lys val lys ile arg gln val asp gly ile asp lys pro thr leu
1801  AAG ACC TAC TTC AAG AAC ATC TTG AAC AGC ATC CGC TTC GAC ATC AAG GTT AAG AAC CAG CCG ATC CTG CAG CCC ACC CTG     622
      trp leu pro pro gln pro ala leu asn ala tyr tyr leu pro asn lys asn gln met val phe pro ala gly ile leu gln pro thr leu
1891  TGG CTG CCC CCA CAG CCG CTC AAT GCC TAC TAT CTA CCC AAC AAG AAC CAG ATG GTG TTC CCC GCG GGC ATC CTG CAG CCC ACC CTG     622
      tyr asp pro phe pro gln ser leu asn tyr gly ile gly thr ile ile gly his glu leu thr his gly phe asp glu thr leu
1981  TAC GAC CCT GAC TTC CCA CAG TCT CTC AAC TAC GGG ATC GGC ACC ATC ATT GGA CAT GAG CTG ACC CAC GGC TTC GAC GAC TGG GGG     652
```

FIG. 5 (cont'd)

```
     gly gln tyr asp arg ser gly asn leu leu his trp thr glu ala ser tyr ser arg phe leu arg lys ala glu cys ile val arg
2071 GGC CAG TAT GAC CGC TCA GGG AAC CTG CTG CAC TGG ACG GAG GCC TCC TAC AGC CGC TTC CTG CGA AAG GCT GAG TGC ATC GTC CGT
                                                                                                                       682
     leu tyr asp asn phe thr val tyr asn gln arg val asn gly lys his thr leu gly glu asn ile ala asp met gly leu phe leu
2161 CTC TAT GAT AAC TTC ACT GTC TAC AAC CAG CGG GTG AAC GGG AAA CAC ACG CTT GGG GAG AAC ATC GCA GAT ATG GGC CTC AAG CTG
                                                                                                                       712
     ala tyr his ala tyr gln lys trp val arg arg glu his gly pro leu pro arg leu lys tyr thr his asp gln leu phe phe
2251 GCC TAC CAC GCC TAT CAG AAG TGG GTG CGT CGG GAG CAC GGG CCA CTT CCC CGG CTC AAG TAC ACA CAT GAC CAG CTC TTC TTC
                                                                                                                       742
     ile ala phe gln asn trp cys ile lys arg arg pro ser gln val leu thr asp lys his ala pro glu his tyr
2341 ATT GCC TTT CAG AAC TGG TGC ATC AAG CGG CGG CCA TCC CAG GTG CTG ACT GAC AAG CAT GCC CCT GAG CAC TAC
                                                                                                                       772
     arg val leu gly ser val ser gln phe glu glu gly phe arg val leu his cys pro lys ser val pro met asn pro ala his lys cys
2431 AGG GTG CTG GGT AGT GTG TCC CAG TTT GAG GAG GGC TTT CGG GTT CTA CAC TGT CCA AAG TCA CCC ATG AAC CCT GCC CAC AAG TGT
     ser val trp ter
     775
2521 TCC GTG TGG TGA CCC CTG CCC GCC TGC ACG CCC CCA CTG CCC CCG CAC GAA TCA CCT CCT GCT CCC GGC TAC CGG AGG CAT GCA CCC
2611 GGT GCC AGC CCC GGT CTG GGC ACC ACC TGC CTT CCA GCC CCT CCA GCC CCT CCT GCT GCC CCT CAC TTC AGG AGG GGC CTG GAG
2701 CAG GGT GAG GCT GGA CTT TGG GGG GCT GTG AGG GAA ATA TAC TGG GGT CCC CAG ATT CTG CTC TAA GGG ACC CTC TGC CAG GCT
2791 GGA TTG TAC GGG CCC CAC CTT CGC TGT GTT CTT GCT GCA AGT CTG GTC AAA TAA ATC ACT GCA CTG TTA AAA AAA AAA AAA
```

FIG. 5 (cont'd)

Sequence comparison between NEP, NL1, NL2 and NL3

```
              1         10        20        30        40
NEP-HUM    MG............KSESQMDITDINTPKPKKKQRWTPLEISLSVLVLL..LTII...AV
              *                                *       *             *
NL1-MOU    MV............ERAGWCRKKSPGFVEYGLMVLLLLLLGAIVTLG.V..FYSI.GKQL
              **          *  **     *  ***  *  ****    *  *       ****
NL2-HUM    MV............ESAGRAGQKRPGFLEGGLLLLLLLVTAALVALGVL..YADRRGKQL
              *                                **  *    **       *
NL3-HUM    MEPPYSLTAHYDEFQEVKYVSRCGAGGARGASLPPGFPLGAARSATGARSGLPRWNRREV 50                            60        70
NEP-HUM    TMIA.......LYATYDD................GICKSSDCIKSAARLIQ.NMDATT
              *        *                       **  *   ***      ***
NL1-MOU    PLLTSL.....LHFSWDERTVVKR...ALRDSSLKSDICTTPSCVIAAARILE.NMDQSR
            * *       * *    ***  ***            *  ****  ********** ***
NL2-HUM    PRLASR.....LCFLQEERTFVKRKPRGIPEAQEVSEVCTTPGCVIAAARILQ.NMDPTT
                 *    **         *                *  *    ***  *  *  *
NL3-HUM    CLLSGLVFAAGLCAILAAMLALKYLGPVAAGGGACPEGCPERKAFARAARFLAANLDASI 80        90       100       110       120       130
NEP-HUM    EPCTDFFKYACGGWLKRNVIPETSSRYGNFDILRDELVVLKDVLQEPKTEDIVAVQ.KA
             **   *  *******   ***** ***   **********  **  **         ** **
NL1-MOU    NPCENFYQYACGGWLRHHVIPETNSRYSVFDILRDELEVILKGVLEDSTSQHRPAVE.KA
             **   ***  ********  ************  *  *********  ***  **    ***** **
NL2-HUM    EPCDDFYQFACGGWLRRHVIPETNSRYSIFDVLRDELEVILKAVLENSTAKDRPAVE.KA
             **   ***  **********  **          *  *   *           *    *     *
NL3-HUM    DPCQDFYSFACGGWLRRHAIPDDKLTYGTIAAIGEQNEERLRRLLARPGGGPGGAAQRKV 140       150       160       170       180       190
NEP-HUM    KALYRSCINESAIDSRGGEPLLKLLPDIYGWPVATENWEQKYGASWTAEKAIAQLNSKYG
              * *****  * *  *    ****   *  *****    *   *   *  *  *  ***
NL1-MOU    KTLYRSCMNQSVIEKRDSEPLLSVLKMVGGWPVAMDKWNETMGLKWELERQLAVLNSQFN
              **********  ****   *  *   *    *********   **   *   ** *******   *****
NL2-HUM    RTLYRSCMNQSVIEKRGSQPLLDILEVVGGWPVAMDRWNETVGLEWELERQLALMNSQFN
               *   ***     **    *    * ***                *       *   *   ***
NL3-HUM    RAFFRSCLDMREIERLGPRPMLEVIEDCGGWDLGGAEERPGVAARWDLNRLLYKAQGVYS 200       210       220       230       240       250
NEP-HUM    KKVLINLFVGTDDKNSVNHVIHIDQPRLGLPSRDYYECTGIYKEACTAYVDFMISVARLI
              ***  **     **  **    ***  ****   **    ** *              **    **   ***
NL1-MOU    RRVLIDLFIWNDDQNSSRHVIYIDQPTLGMPSREYYFQEDNNHKVRKAYLEFMTSVATML
              ************ *** *   *   *****************          *  ***  ***   **   ****  *
NL2-HUM    RRVLIDLFIWNDDQNSSRHIIYIDQPTLGMPSREYYFNGGSNRKVREAYLQFMVSVATLL
                *    *      **  ****   *  ***      *    *   *                    *          *
NL3-HUM    AAALFSLTVSLDDRNSSRYVIRIDQDGLTLPERTLYLAQDEDSE...KVLAAYRVFMERVL
```

FIG. 6

```
              260        270        280        290        300        310
NEP-HUM   RQEERLPIDENQLALEMNKVMELEKEIANATAKP..EDRNDPMLLYNKMTLAQIQNNFSL
            +    +      ++  + +++     ++++     -  + +  ++   +  +     + +
NL1-MOU   RKDQNLSKESAMVREEMAEVLELETHLANATVPQ..EKRHDVTALYHFMDLMELQERFGL
          +  -  ++       +   +  +  ++++++  ++  +++++    .  -++ ++++++*  -  +++   +++
NL2-HUM   REDANLPRDSCLVQEDMVQVLELETQLAKATVPQ..EERHDVIALYHRMGLEELQSQFGL
                +    +            +    +  +++  ++       +  ++   +     +    ++
NL3-HUM   SL...LGADAV..EQKAQEILQVEQQLANITVSEYDDLRRDVSSMYNKVTLGQLQKITP.

320        330        340        350        360        370
NEP-HUM   EINGKPFSWLNFTNEIMSTVNISITNEEDVVVYAPEYLTKLKPILTKYSARDLQNLMSWR
              +         ********* +++++   +    +   ++++   +++  +   ++++   ++
NL1-MOU   ....KGFNWTLFIQNVLSSVEVELFPDEEVVVVYGIPYLENLEDIIDSYSARTMQNYLVWR
              **********  *****  *  *+**************  *******   ******+*+
NL2-HUM   ....KGFNWTLFIQTVLSSVKIKLLPDEEVVVVYGIPYLQNLENIIDTYSARTIQNYLVWR
                       +                      ++++       + +      +         +        ++++++
NL3-HUM   .....HLRWKWLLDQIF...QEDFSEEEEVVLLATDYMQCVSQLIRSTPHRVLHNYLVWR 380        390        400        410        420        430
NEP-HUM   FIMDLVSSLSRTYKESRNAFRKALYGTTSETATWRRCANYVNGNMENAVGRLYVEAAFAG
             +     +++    ++ +    ******** +     ++ +   +++ +++  +++  ++     ++
NL1-MOU   LVLDRIGSLSQRFKEARVDYRKALYGTTVEEVRWRECVSYVNSNMESAVGSLYIKRAFSK
          ************   ++   *****  ++   ************   ******   ******        ++
NL2-HUM   LVLDRIGSLSQRFKDTRVNYRKALFGTMVEEVRWRECVGYVNSNMENAVGSLYVREAFPG
               +      +       +           +  +  +    +                 +  +  +     +         ++++++
NL3-HUM   VVVVLSEHLSPPFREALHELAQEMEGSDKPQELARVCLGQANRHFGMALGALFVHEHFSA 440        450        460        470        480        490
NEP-HUM   ESKHVVEDLIAQIREVFIQTLDDLTWMDAETKKRAEEKALAIKERIGYPDDIVSNDNK.L
            ++   +   ++   ++  ++        ++ +  +++   +  ++   +++    + +  +++++  +        ++  +
NL1-MOU   DSKSTVRELIEKIRSVFVDNLDELNWMDEESKKKAQEKAMNIREQIGYPDYILEDNNKHL
          ****  *****  +  +    +++     ****    ++++++**************+   ******  ******    +   +
NL2-HUM   DSKSMVRELIDKVRTVFVETLDELGWMDEESKKKAQEKAMSIREQIGHPDYILEEMNRRL
             ++      +   ++       +   ++  +++      +     +                  +
NL3-HUM   ASKAKVQQLVEDIKYILGQRLEELDWMDAETRAAARAKLQYMMVMVGYPDFLLKPDA..V 500        510        520        530        540        550
NEP-HUM   NNEYLELNYKEDEYFENIIQNLKFSQSKQLKKLREKVDKDEWISGAAVVNAFYSSGRNQI
           ++   +   ++  ++++   ++++        **********   ++  ************      +++
NL1-MOU   DEEYSSLTFYEDLYFENGLQNLKNNAQRSLKKLREKVDQNLWIIGAAVVNAFYSPNRNQI
          *****  + *  *******   *****   +****   ******  **************************
NL2-HUM   DEEYSNLNFSEDLYFENSLQNLKVGAQRSLRKLREKVDPNLWIIGAAVVNAFYSPNRNQI
            + +     + +++    -    +  +      +   +  + +   ++      ++  +   ++   ++
NL3-HUM   DKE.YEFEVHEKTYFKNILNSIRFSIQLSVKKIRQEVDKSTWLLPPQALNAYYLPNKNQM
```

FIG. 5 (cont'd)

```
             560        570        580        590        600        610
NEP-HUM  VFPAGILQPPFFSAQQSNSLNYGGIGMVIGHEITHGFDDNGRNFNKDGDLVDWWTQQSAS
         ++++++++++++  +  +++ +++++++++++++++++++++++ +  -   +++    ++
NL1-MOU  VFPAGILQPPFFSKDQPQSLNFGGIGMVIGHEITHGFDDNGRNFDKNGNMLDWWSNFSAR
         +++++++++++++ +++ ++ +++++++++ ++++ +++ ++ +  +      ++++++
NL2-HUM  VFPAGILQPPFFSKEQPQALNFGGIGMVIGHEITHGFDDNGRNFDKNGNMMDWWSNFSTQ
         ++++++++++   ++  ++ ++++   ++++ +++ +++ ++ +  +      ++  ++
NL3-HUM  VFPAGILQPTLYDPDFPQSLNYGGIGTIIGHELTHGYDDWGGQYDRSGNLLHWWTEASYS 620        630        640        650        660        670
NEP-HUM  NFKEQSQCMVYQYGNFSWDLAGGQHLNGINTLGENIADNGGLGQAYRAYQNYIKKNGEEK
          +   +++++ +++++++++ ++   +    ++++++++++++ ++++ ++        +
NL1-MOU  HFQQQSQCMIYQYGNFSWELADNQNVNGFSTLGENIADNGGVRQAYKAYLRWLADGGKDQ
         ++   ++ +++++++++  ++    +   +   +++++++++++ ++ ++ ++    +  + +++++
NL2-HUM  HFREQSECMIYQYGNYSWDLADEQNVNGFNTLGENIADNGGVRQAYKAYLKWMAEGGKDQ
              ++   ++  +  + ++++++++++++++++++++ ++ ++  ++   +  +
NL3-HUM  RFLRKAECIVRLYDNFT...VYNQRVNGKHTLGENIADMGGLKLAYHAYQKWVREHGPEH 680        690        700        710        720        730
NEP-HUM  LLPGLDLNHKQLFFLNFAQVWCGTYRPEYAVNSIKTDVHSPGNFRIIGTLQNSAEFSEAF
         ++++ +  ++++ +  +++++ ++++ ++ +++++++++++  +  + +++   +++++
NL1-MOU  RLPGLNLTYAQLFFINYAQVWCGSYRPEFAVQSIKTDVHSPLKYRVLGSLQNLPGFSEAF
         . ++++ ++ ++++++++++++++ ++++ + ++++++++++++++++++++  +    +     +
NL2-HUM  QLPGLDLTHEQLFFINYAQVWCGSYRPEFAIQSIKTDVHSPLKYRVLGSLQNLAAFADTF
         ++  +  ++  +++++ ++  +++++++ +     +    ++++++      +
NL3-HUM  PLPRLKYTHDQLFFIAFAQNWCIKRRSQSIYLQVLTDKHAPEHYRVLGSVSQFEEFGRVL 740        750
NEP-HUM  HCRKNSYMNPEKKCRVW
         ++     +  +  +  ++  +
NL1-MOU  HCPRGSPMHPMKRCRIW
         ++  ++  ++++    +++  +
NL2-HUM  HCARGTPMHPKERCRVW
         ++     ++ +     +   ++
NL3-HUM  HCPKVSPMNPAHKCSVW
```

FIG. 6 (cont'd)

NL1 in the TESTIS
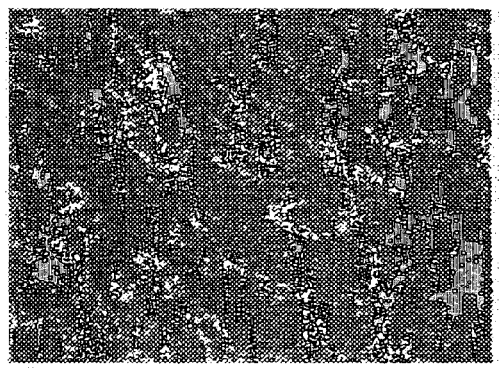
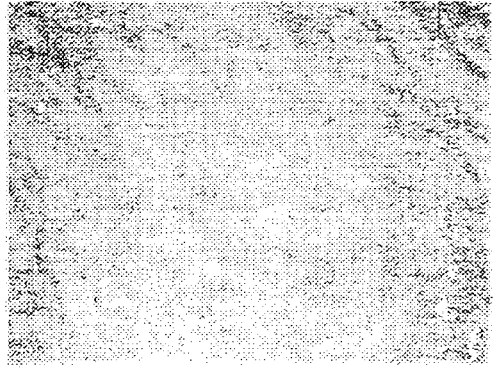
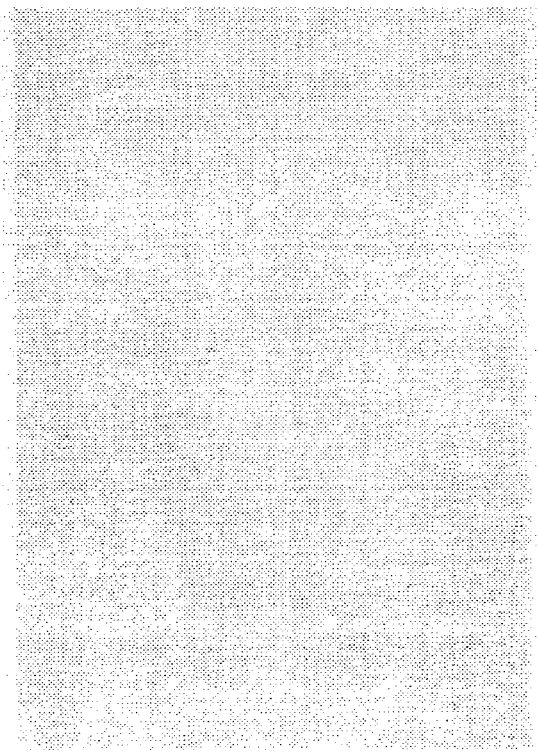
FIG. 7

NL3 in the BRAIN
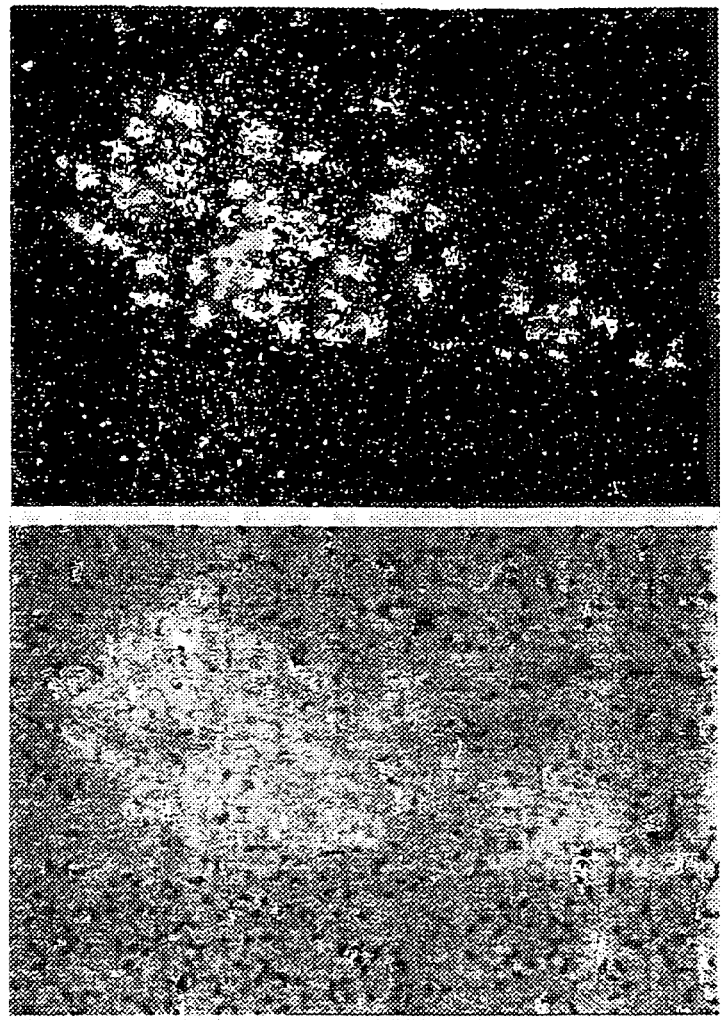
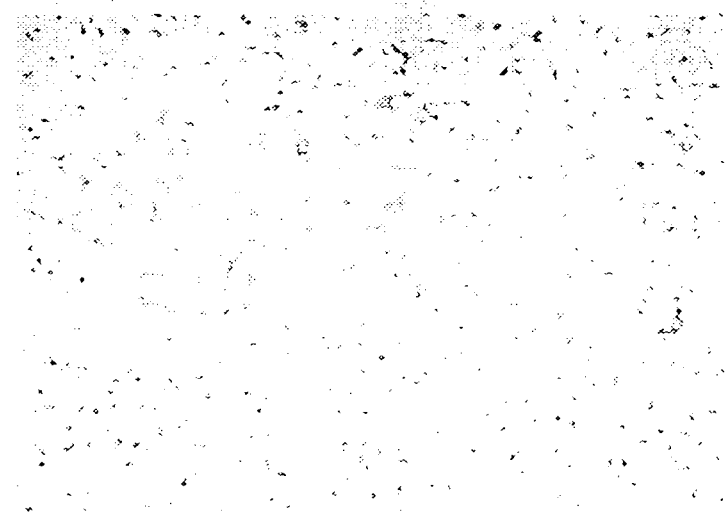
FIG. 9

Structure and expression of NL-1
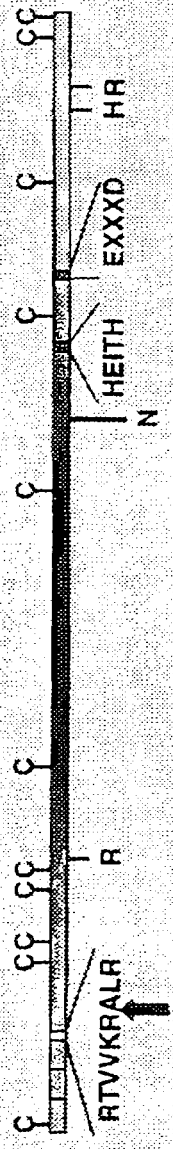
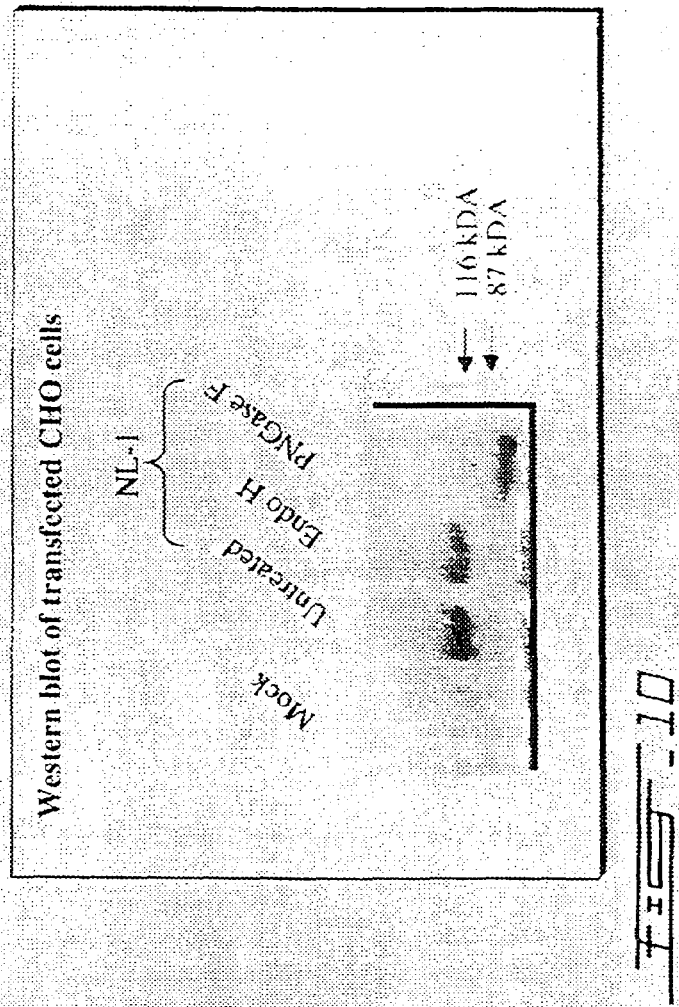
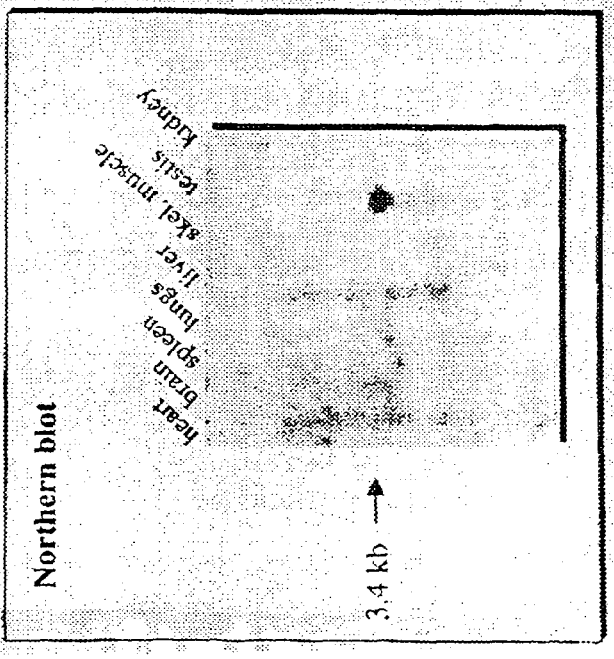
FIG-10

METALLOPROTEASES OF THE NEPRILYSIN FAMILY

This application is the U.S. National Phase of International Application PCT/CA00/00147, filed Feb. 11, 2000, published in English under PCT Article 21(2), which designated the U.S. PCT/CA00/00147 claims priority to Canadian Patent Application No. 2,260,376, filed Feb. 11, 1999. The entire content of these applications are incorporated herein by reference.

BACKGROUND OF THE INVENTION

Peptides are used by cells from yeast to mammals to elicit physiological responses. The use of peptides as messengers usually involves the following steps: 1) production and release of the peptide by a specific cell, 2) interaction of the peptide with a receptor on the surface of the target cell, and 3) degradation of the peptide to terminate its action. The first and last steps of this scheme require the participation of proteases/peptidases. There is increasing evidence that membrane-associated zinc-metallopeptidases play important roles in both of these steps. Although activation of prohormone precursors into bioactive peptides is generally performed by proteases of the subtilisin family located in the Trans-Golgi Network or in secretory granules of the cell (for a review see: (Seidah and Chretien, 1995)) a few peptides need a final processing step. This step involves the action of membrane-associated zinc-metallopeptidases. Two cases are particularly well documented: angiotensin-converting enzyme (ACE) which cleaves inactive angiotensin I into angiotensin II (Corvol and Williams, 1997) and endothelin-converting enzymes (ECEs) which cleave isoforms of big endothelins into endothelins (Turner, 1997a). In addition to their role in peptide activation, cell surface zinc-metallopeptidases have also been implicated in the termination of the peptidergic signal by breaking down the active peptides into inactive fragments. One of the best known of these peptidases is probably Neutral Endopeptidase-24.11 (Neprilysin, NEP) that has been implicated in the physiological degradation of several bioactive peptides (Kenny, 1993). Interestingly, NEP and the ECEs show significant structural similarities and appear to be members of a family of peptidases that also includes PEX, a newly discovered and not yet characterized peptidase, and the KELL blood group protein (Turner and Tanzawa, 1997b). Because of their important role as regulators of bioactive peptide activity, these enzymes (more specifically NEP and the ECEs) have been identified as putative targets for therapeutic intervention, similar to the way ACE inhibitors are used to control blood pressure. The recent discovery of PEX, another member of the family, which appears to be involved in phosphate homeostasis, raised the possibility that other yet unknown members might exist.

Members of the NEP-like family are type II membrane proteins consisting of three distinct domains: a short NH2-terminal cytosolic sequence, a single transmembrane region, and a large extracellular or ectodomain responsible for the catalytic activity of the enzyme. There are potential N-glycosylation sites and cysteine residues that are involved in disulfide bridges stabilizing the conformation of the active enzyme. These enzymes are metalloenzymes with a Zn atom in their active site. As such, they belong to the zincin family of peptidases which is characterized by the active site consensus sequence HEXXH (Hooper, 1994), where the two histidine residues are zinc ligands. In members of the NEP-like family of peptidases, the third zinc ligand is a glutamic acid residue located on the carboxy-terminus side of the consensus sequence. This characteristic puts them in the gluzincin sub-family (Hooper, 1994). The model enzyme for gluzincins is thermolysin (TLN) a bacterial protease whose 3D structure has been determined by X-ray crystallography (Holmes and Matthews, 1982). The active site of NEP has been extensively studied by site-directed mutagenesis and several residues involved in zinc binding (Devault et al., 1988b; Le Moual et al., 1991; Le Moual et al., 1994), catalysis (Devault et al., 1988a; Dion et al., 1993), or substrate binding (Vijayaraghavan et al., 1990; Beaumont et al., 1991; Dion et al., 1995; Marie-Claire et al., 1997) have been identified (for a recent review see Crine et al., 1997).

SUMMARY OF THE INVENTION

Here, we developed an RT-PCR strategy to look for other members of this important family of peptidases. This strategy allowed the molecular cloning and characterization of three additional NEP-like (NL) metallopeptidases (called NL-1, NL-2 and NL-3). Knowledge obtained through these studies allows the generation of reagents (nucleic acid probes and primers, antibodies and active recombinant enzymes) for further biochemical characterization of these enzymes and their pattern of expression and will greatly help the rational design of specific inhibitors that could be used as therapeutic agents.

Accordingly, the present invention relates to the following products:

A. Degenerate primers for screening new NEP-related enzymes;
B. NL-1, NL-2 and NL-3 proteins as NEP-related enzymes;
C. Nucleic acids encoding these enzymes;
D. Antibodies directed against the enzymes;
E. Recombinant vectors comprising the nucleic acids encoding the enzymes and hosts transformed therewith;
F. Fragments of the nucleic acids useful as probes or primers to hybridize and detect the presence of an NL-1, NL-2 and NL-3 genes, or to hybridize and amplify and produce gene fragments;
G. Soluble forms of NL-1, NL-2 and NL-3; and
H. Nucleic acids comprising the N-terminal part of NL-1 or NL-2 which terminates with a sequence encoding a furin recognition site, such nucleic acids being useful for making a fusion protein with the ectodomain of any protein of interest, and for releasing a soluble form of that protein of interest (containing the ectodomain) in the medium.

Also the present invention relates to the following methods:

A. A method for screening NEP-related enzymes that make use of degenerate primers or probes selected from a region of NEP family members in a highly conserved region, namely around the zinc-binding sites; and
B. A method for producing NL-1, NL-2 or NL-3 that includes the steps of culturing the above recombinant host and recovering NL-1, NL-2 and NL-3 gene products therefrom.

The present invention will be described hereinbelow by referring to specific embodiments and appended figures, which purpose is to illustrate the invention rather than to limit its scope.

In the first section, general procedures leading to the identification and localization of NL-1, NL-2 and NL-3 are given. In the second section, slightly different procedures are given for completing or reiterating the work performed on NL-1.

BRIEF DESCRIPTION OF THE FIGURES

FIG. 1: Amino acid sequence comparison of human NEP (SEQ ID NO: 1), PEX (SEQ ID NO: 2), KELL (SEQ ID NO: 3) and ECE1 (SEQ ID NO: 4) peptidases. Amino acid sequences in boxes are those used to design the oligonucleotide primers. Numbers and arrows under the sequences identify the primer and its orientation.

FIG. 2: Sequences of the oligonucleotide primers used in the PCR reactions (1A: SEQ ID NO: 5; 1B: SEQ ID NO: 6; 2A: SEQ ID NO: 7; 2B: SEQ ID NO: 8; 3: SEQ ID NO: 9; 4: SEQ ID NO: 10; and 5: SEQ ID NO: 11).

FIG. 3: Nucleotide (SEQ ID NO: 12) and amino acid (SEQ ID NO: 13) sequence of the mouse NL-1 cDNA. The sequence of the DNA fragment obtained by PCR is in brackets.

FIG. 4: Partial nucleotide (SEQ ID NO: 14) and amino acid sequence (SEQ ID NO: 15) of the human NL-2 cDNA. The sequence of the DNA fragment obtained by PCR is in brackets.

FIG. 5: Partial nucleotide (SEQ ID NO: 16) and amino acid sequence (SEQ ID NO: 17) of the human NL-3 cDNA.

FIG. 6: Amino acid sequence comparison of NEP (SEQ ID NO: 1), NL-1 (SEQ ID NO: 13), NL-2 (SEQ ID NO: 15) and NL-3 (SEQ ID NO: 17) peptidases.

FIG. 7: In situ hybridization of mouse testis sections using NL-1 as a probe.

FIG. 9: In situ hybridization of mouse spinal chord sections

FIG. 10: Expression of NL-1 in mammalian cells.

DESCRIPTION OF THE PREFERRED EMBODIMENTS OF THE INVENTION

Section 1)

Materials and Methods

DNA and RNA manipulations

Figure 8:
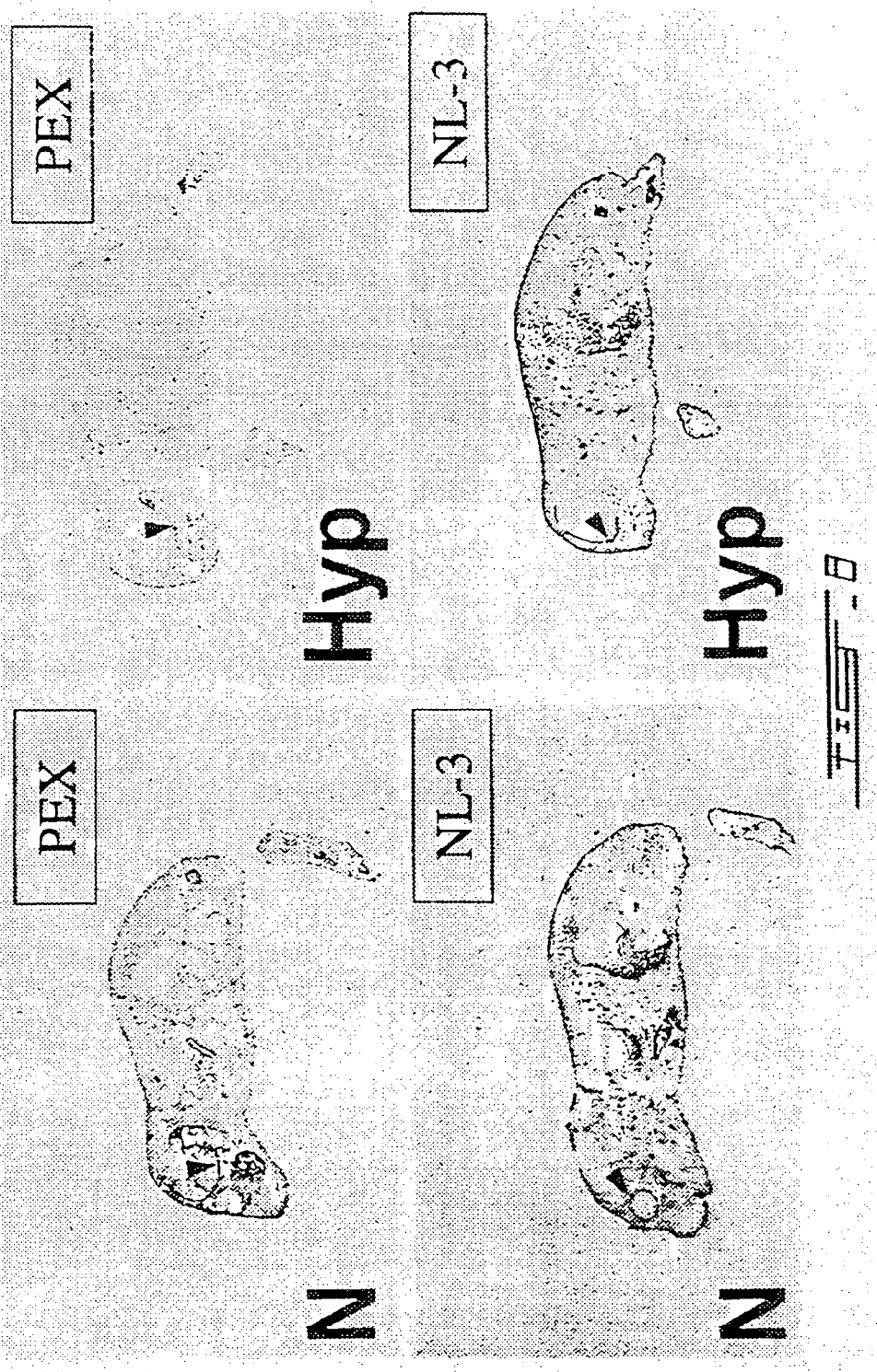
FIG. 8: In situ hybridization of mouse sections using mouse NL-3 as a probe.

All DNA manipulations and Northern blot analysis were performed according to standard protocols (Ausubel et al., 1988; Sambrook et al., 1989).

mRNA purification and cDNA synthesis mRNAs were prepared from mouse testis using Quick Prep Micro mRNA purification kit (Pharmacia Biotech). Purified mRNAs were kept at −70° until ready used. First strand cDNA was synthesized from 1 µg of mRNA using the First-Strand cDNA synthesis kit (Pharmacia Biotech). The human testis cDNA library was obtained from Clonetech.

Polymerase chain reaction protocol

PCR was performed in a DNA thermal cycler with 5 µl of cDNA template and 1 µl of Taq DNA polymerase in a final volume of 100 µl, containing 1 mM $MgCl_2$, 2 µM of each primer oligonucleotide, 20 µM of each dNTP and 5% DMSO. Cycling profiles included an initial denaturation step of 5 min at 94° C., followed by 30 cycles of 1 min at 94° C., 1 min at 40° C. and 1.5 min at 72° C. A final extension step was performed at 72° C. for 10 min. The amplified DNA was loaded on a 2% agarose gel and visualized by staining with ethidium bromide. Fragments ranging in size between 500–700 bp were cut and eluted from the gel. If needed, a second round of PCR was done with nested oligonucleotide primers, using 10 µl of the first PCR reaction, or of the eluted band cut from the agarose gel. Resulting fragments were ligated in pCR2.1 vector (Invitrogen) according to the distributor's recommendations. DH5α Escherichia coli cells were transformed with the ligation mixture and grown on 2YT plates in the presence of kanamycin. Plasmids were prepared from resistant cells and sequenced.

In situ hybridization on mouse tissues and chromosomal localization of human genes In situ hybridization on whole mouse slices or isolated tissues was performed as described previously (Ruchon et al., 1998).

To determine the chromosomal localization of human NL-2 and NL-3 genes, a technique for mapping genes directly to banded human chromosomes was used. Metaphase chromosomes were obtained from lymphocytes cultured from normal human peripheral blood. Cells were synchronized with thymidine and treated with 5-bromodeoxyuridine (BrdU) during the last part of the S phase to produce R-banding. Biotin-labeling of the probe was done by nick-translation (Bionick, BRL) and the probe was visualized by indirect immunofluorescence.

Antibody production

To raise antibodies against the new peptidases, the cDNA sequences of each protein was compared to that of other members of the family and the sequence segment showing the less homology was used. These sequences are from amino acid residues 273 to 354 for NL-1, from 75 to 209 for NL-2 and from 143 to 465 for NL-3. These cDNA fragments were cloned in vector pGEX2T (Pharmacia Biotechnology) downstream from and in phase with Gluthatione-S-transferase (GST). Plasmids were transformed in E. coli strain AP401 and, induction of synthesis and purification of the fusion proteins were performed as recommended by the supplier. The NL polypeptides were cleaved from the fusion protein with thrombin and purified by SDS-PAGE. NL polypeptides were injected to rabbits or mice according to the following schedules: for rabbits, initial injection of 150 µg of protein with boosts of the same amount 4 weeks and 8 weeks following the initial injection; for mice, initial injection of 100 µg of protein followed by boosts of the same amounts 3 and 6 weeks later. A month after the last injection, sera were collected from the animals and tested by immunoblotting against the initial E. coli-produced antigens and the recombinant proteins produced in mammalian cell lines.

Production of monoclonal antibodies cDNA fragments corresponding to amino acids segments of NLs selected to raise antibodies were used to construct a GST-fusion protein in E. coli. This fusion protein was purified from E. coli extracts by affinity chromatography on a glutathione-Sepharose column according to the supplier's instructions (Amersham-Pharmacia). After thrombin cleavage, the NL portion of the GST fusion protein was further purified by electroelution from a polyacrylamide gel. This material was used to immunise 4 mice (5 injections of ≈50 µg of NL polypeptide). Blood was collected from each mice after the immunisation schedule and the presence of antibodies in mice serum was assessed by ELISA using microtiter plates coated with NL polypeptide from E. coli extracts. Mice sera were also tested for the presence of NL antibodies by Western blotting extracts of mammalian cells transfected with the NL expression vectors. One mouse selected for its high titer of NL specific antibodies (as measured by ELISA)

was sacrificed and its spleen cells were collected and immortalised by fusion with myeloma cells(strain: P3-X63Ag.653 from ATCC) as described previously (Crine 1985). Hybridoma cells were selected for their ability to grow in HAT selection medium and cloned by several rounds of limiting dilution. Hybridomas showing proper affinity and specificity to the enzymes NL-1, NL-2 and NL-3 where selected.

Expression of NLs in cultured mammalian cells and enzymatic assays The cDNAs for NL-1 and NL-3 were cloned in vectors pcDNA3 or pRcCMV (Invitrogen) and introduced by transfection in mammalian cell lines according to procedures already described in our laboratory (Devault et al., 1988a). Procedures to prepare extracts of cellular proteins or culture media were also described in previous papers (Devault et al., 1988a; Lemay et al., 1989). The presence of NLs in these extracts was monitored by immunoblotting using specific antibodies.

Extracts of cellular proteins and culture media were assayed for enzymatic activity. Two tests were performed. The first used [$^3$H]-Tyr-(D)Ala$_2$-Leu-enkephalin as substrate and was performed according to Lemay et al., (1989). The second used bradykinin as substrate and was performed as described by Raut et al. (1999).

Results

Cloning of NL-1, a new member of the NEP family

The molecular cloning in the past few years of ECEs, PEX and KELL showed that all these proteins have between 50 and 60% similarity with NEP. This observation led us to believe that these peptidases are part of an extended family and that there could be still additional members to be discovered. To test this hypothesis, we aligned the amino acid sequences of the members of the NEP-like family and designed degenerate oligonucleotide primers to be used in RT-PCR reactions (FIGS. 1 and 2). These primers were located on either side of the HEXXH consensus sequence for zincins. Because they are highly degenerate, primers 1 and 2 were each subdivided into two pools, 1A-1B, and 2A-2B, respectively (FIG. 2). Any PCR amplified DNA fragment that corresponds to a peptidase of the family should normally contain the consensus sequence and be easily recognized by sequencing of the cloned fragments. Using this strategy, we first performed PCR reactions with primer pairs 1A-3 and 1B-3. The amplified DNA migrates mostly as a smear starting at around 700 bp and going down to 100 bp. As the expected fragments should be around 550 bp, we isolated from the gel the section corresponding to DNA fragments longer than 500 bp. A second round of PCR reactions was performed with both crude PCR products of the first reaction and isolated DNA bands, using primers 2A-3 and 2B-3. The expected 296 bp fragment was seen on the gel (not shown).

Cloning of these DNA fragments generated approximately 350 clones, of which 44 were sequenced. Nine of these had no inserts or corresponded to sequences not related to the NEP family, 24 corresponded to NEP, 3 to PEX, and 8 corresponded to one putative new member of the family, since they all contained the HEXXH consensus sequence for zincins and showed 65% homology with mouse NEP (in boxes FIG. 3). This fragment was then used to screen a mouse testis cDNA library, and allowed us to isolate a complete cDNA of 2592 nucleotides (FIG. 3). The identity of this sequence with other members of the family is presented in Table I. This new member was called NL-1, for NEP-like peptidase 1.

Cloning of NL-2 and NL-3

A strategy similar to that described for amplification of enzymes of the NEP family from mouse testis cDNAs was used with a human testis cDNA library using two different oligonucleotide primers. This time, DNA fragments of approximately 900 bp were obtained and cloned. Ten clones were sequenced, revealing the presence of NEP and two new peptidases of the family that we have called NL-2 and NL-3.

The NL-2 PCR fragment was 879 nucleotides in length and encoded a 293 amino acid residue segment probably located in the carboxy-terminal domain of this putative peptidase (in brackets FIG. 4). This PCR fragment was then used to screen a lambda gt10 human brain cDNA library. It allowed the isolation of other cDNA fragments which overlap partially with the NL-2 PCR fragment. Fusion of these lambda clones and the PCR fragment resulted in an open reading frame of 770 amino acid residues. The use of 5' RACE protocols with human testis cDNA libraries allowed completion of the sequence of NL-2 ORF (FIG. 4). This ORF codes for a putative protein that is about 80% identical to the mouse NL-1 protein (FIG. 6). Across species, members of the NEP, PEX, ECEs sub-families have highly conserved sequences (more than 94% identity). Although a sequence identity of about 80% only exists between the novel human protein and mouse NL-1, these proteins share unique characteristics that make possible the fact that NL-2 protein may be the human homologue of NL-1. The identity of NL-2 with other members of the family is presented in Table I.

The 879 bp PCR fragment encoding NL-3 showed an open reading frame of 293 amino acid residues (FIG. 5, in brackets). Sequence analysis of NL-3 showed that it was 94.2% identical to an EST sequence from mouse embryonic tissue present in publicly accessible DNA data banks. This mouse EST sequence, commercially available from American Tissue and Cell Culture (ATCC), had been obtained previously by our laboratories.

Since Northern blot analysis of human tissues with the NL-3 PCR fragment showed the expression of this protein in spinal chord (see below), the same PCR DNA fragment was used to screen by hybridization a human spinal chord cDNA library constructed in phage A vectors. One clone contained a full-length ORF of 752 amino acid residues that encompassed the 293 amino acid residue ORF of the PCR fragment. Further probing, cloning and sequencing lead to the obtention of NL-3 full sequence, shown in FIG. 5.

FIG. 6 presents a comparison of the amino acid sequence of the new NEP-like enzymes and Table I shows the extent of identity between members of the family.

Cellular distribution of NL-1, NL-2 and NL-3 peptidases

Determining the tissue distribution of NL-1, NL-2 and NL-3 may provide clues to identify the peptidergic systems in which they are involved. It will be particularly interesting to compare the tissue distribution of these peptidases with that of NEP and the ECEs to determine whether or not the physiological functions of NL-1 and/or NL-2 and/or NL-3 may overlap those of NEP and/or ECEs.

In situ hybridization (ISH), using our mouse cDNA, was used to determine the spatial and temporal expression of NL-1 during mouse development, as done previously for PEX (Ruchon et al., 1998)). Serial sections of whole foetal (12, 15 and 19 dpc) and adult mice (1, 3 and 6 days old) were hybridized with an [$^{35}$S]-labeled RNA probe. FIG. 7 shows a section of mouse testis which was the only tissue identified to express NL-1 by this technique. Cells of seminiferous tubules are specifically labeled but spermatids located near the center of the tubule showed strongest labeling. These cells are in the last stage of maturation into spermatozoids. The presence of NL-1 in testis has now been confirmed by Northern analysis of mouse tissues (see FIG. 10). Other tissues express NL-1, when analyzed by RT-PCT, which is a more sensitive assay (not shown).

A similar approach was used to determine the localization of NL-3 using the mouse EST obtained from ATCC. FIG. 8 shows sections of whole mouse at 17 days of embryonic development and 4 days post-natal. Several tissues are expressing this putative peptidase including brain, where it is associated with neurons (FIG. 9), spinal chord, liver, spleen and bones. Labeling was stronger in bones from Hyp mouse, an animal model for hypophosphatemic rickets (FIG. 8). In bones, NL-3 was found to be expressed by osteoblasts (not shown).

Northern blotting experiments were performed on several tissues with NL-2 and NL-3 probes. A Human Multiple Tissues Northern Blot (Clontech) was hybridized with specific probes. A single RNA band of approximately 4.0 kb was revealed by the probe for NL-2. Expression of NL-2 is restricted to brain and spinal cord (not shown). However, RT-PCR has shown the presence of this enzyme in testis (not shown).

A single RNA band of approximately 3.0 kb was detected with the specific probe for NL-3 (not shown). NL-3 expression was observed mainly in ovary, spinal cord and adrenal gland.

Chromosomal localisation of the human gene for NL-2 and NL-3

As a mean to get clues on the function of the new metallopeptidases in vertebrates, we have localized the new cDNAs on human chromosomes, in order to look for a possible link between the gene locus and mapped genetic diseases in humans. To do so, we have mapped the NL-2 and NL-3 genes by high-resolution fluorescence in situ hybridization (FISH). NL-2 was localized to chromosome band 1p36. Consistent with the cellular distribution of NL-2 in humans, genetic diseases of the CNS such as dyslexia, neural tube defect, neuroblastoma, neuronal type of Charcot-Marie-Tooth disease have all been mapped in this region and represent potential targets for a role of NL-2 in humans. NL-3 was localized to chromosome band 2q37. Consistent with a role of NL-3 in bones, a form of Albright hereditary osteodystrophy was mapped to the same chromosomal locus (Phelan et al., 1995).

In view of the foregoing, NL-2 and NL-3 are metallopeptidases that are assumed to be immediately useful as markers for a disease or disorder associated with human chromosomal locus 1p36 and 2q37, respectively. Their localization on a chromosome band associated with known diseases suggests that they may be expressed or co-expressed with one or more genes, as a cause or a consequence of disease development. It is possible that these enzymes are up or down regulated, alone or along with other genes involved in a disease. Therefore, antibodies or other ligands specific to NL-2 or NL-3 may be used for a diagnostic purpose, as well as primers or probes in diagnostic assays using nucleic acid hybridization or amplification techniques. Otherwise, primers or probes directed against the nucleic acids of NL-2 and NL-3 would be useful to map the mutations of a gene located in close proximity and involved in the disease. Therefore, no matter which exact function NL-2 and NL-3 gene products have, their chromosomic localization provides one diagnostic utility. This localization as well as the tissular distribution provide information as to the disease and tissue to be investigated to elucidate the exact function of these enzymes.

NL-1 resembles NL-2, sharing with the latter about 80% homology in the amino sequence and sharing structural characteristics such as the furin recognition sequence located at the proximal end of the ectodomain. NL-2 might be the human homologue of mouse NL-1. If such was the case, these two proteins would have a substantial degree of divergence and, maybe, different profiles of activity varying from one species to another.

Chromosomal localization of NL-1 was determined in mouse genome by Single Strand Conformational Polymorphism (SSCP) in collaboration with The Jackson Laboratory Backcross DNA Panel Mapping Resource. NL-1 was localized to the distal region of mouse chromosome 4 which corresponds to human chromosome region 1p36 where is located NL-2 gene. This reinforces our hypothesis that NL-1 and NL-2 are species variants.

Production of antibodies against NLs

Antisera collected from injected animals were first tested by immunoblotting on GST-antigen fusion proteins produced in *E. coli*. Antiserum from one rabbit recognized the NL-1 -related polypeptide and antisera from one mouse and one rabbit reacted with the NL-3-related polypeptide (results not shown). The anti NL-1 antiserum and the mouse anti NL-3 antiserum, which appeared more specific than the rabbit antiserum, were next tested by immunoblotting on extracts of proteins and culture media from cells expressing NL-1 or NL-3 (see below).

Expression of NL-1 in CHO cells

The cDNA encoding the full-length NL-1 protein was cloned in the mammalian expression vector pcDNA3-RSV and transfected in CHO cells. Stable cell lines were established by selection with the drug G418 and tested by immunoblotting for the presence of NL-1.

Small amounts of NL-1 were found in the extracts of transfected CHO cells (results not shown). This intracellular species was sensitive to endo H digestion, indicating that the sugar moiety was not mature and suggesting ER localization (results not shown). The culture medium of transfected CHO cells showed the presence of soluble NL-1 (FIG. 10). This extracellular species was resistant to endo H suggesting true transport through the late secretory pathway. The cDNA sequence of NL-1 predicts a type II transmembrane protein. The mechanism by which NL-1 is transformed into a soluble protein is not known presently. However, examination of the amino acid sequence revealed the presence of a putative furin cleavage site from residue 58 to 65 (FIG. 3). A similar site is present in NL-2 sequence.

Figure 11:
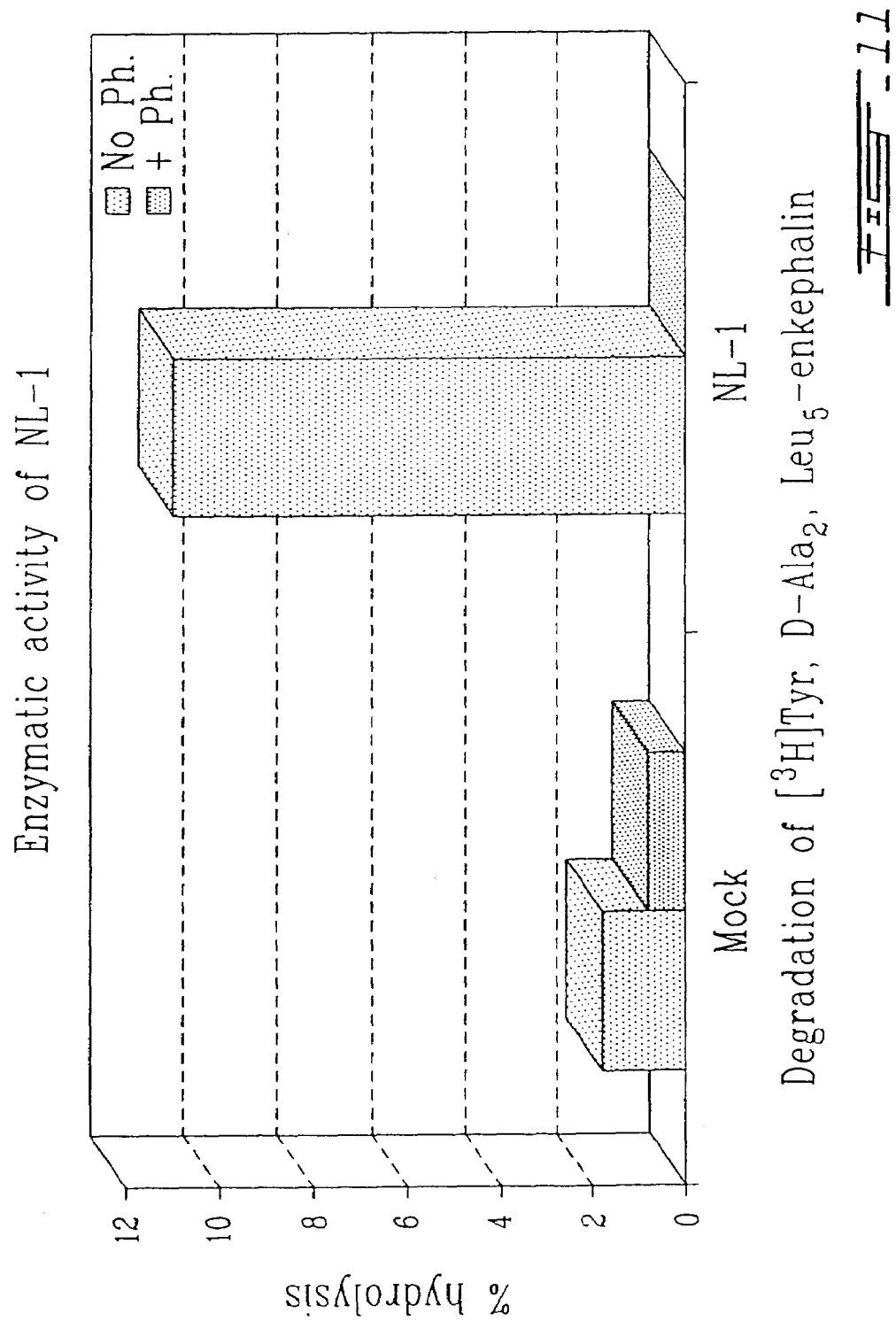
FIG. 11: Activity of recombinant soluble NL-1.

The soluble form of NL-1 was assayed for activity using [$^3$H]-Tyr-(D)Ala$_2$-Leu-enkephalin and bradykinin as substrates. FIG. 11 shows that NL-1 can degrade the enkephalin substrate ($K_m$=18±10 µM) and that this activity can be inhibited by phosphoramidon ($IC_{50}$=0.9±0.3 nM) and thiorphan ($K_m$=47±12 nM), a general inhibitor of enzymes of the NEP family. Bradykinin is also a substrate for NL-1 (not shown).

Use of NL-1 amino-terminal domain to promote secretion

Figure 12:
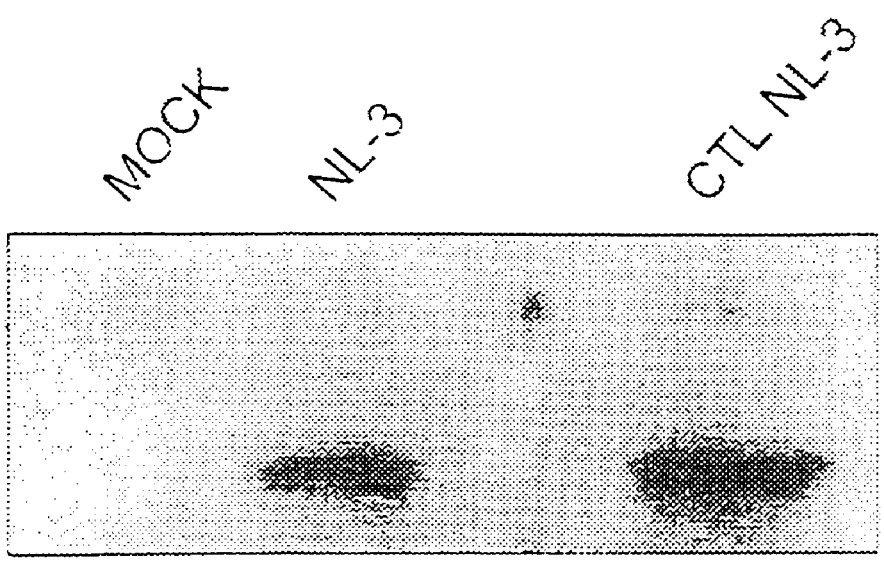
FIG. 12: Expression of a soluble form of NL-3 using NL-1 amino-terminal domain.

The observation that NL-1 ectodomain was secreted, possibly through cleavage of the transmembrane segment by furin, raised the possibility to promote secretion of exogenous proteins that could be spliced to NL-1 amino-terminal domain (from initiator methionine to the furin site). To test this hypothesis, the ectodomain of NL-3 (from the third cysteine to the end) was spliced to NL-1 amino-terminal domain using a PCR strategy and the recombinant DNA cloned in expression vector pRcCMV. The fusion protein was expressed by transfection of the vector in COS-1 and HEK 293 cells. The culture media of transfected cells was analyzed by immunoblotting using the mouse antiserum against NL-3. FIG. 12 shows the presence of NL-3 in the spent culture media of both COS-1 and HEK 293 cells. This result shows that NL-1 amino-terminal domain can be used to promote secretion of exogenous proteins.

The soluble form of NL-3 was assayed for activity using [$^3$H]-Tyr-(D)Ala$_2$-Leu-enkephalin as substrate. No activity was found.

The previous experiment showed that it was possible to use the amino-terminal domain of NL-1 to promote secretion of an otherwise membrane attached protein ectodomain. To verify whether the same strategy could be used to promote secretion of small peptides, a PCR strategy was used to splice human β-endorphin to the amino-terminal domain of NL-1 and the recombinant DNA was cloned in vector pRcCMV. The fusion protein was expressed by transfection of the vector in COS-1 and HEK 293 cells. The culture media of transfected cells was collected 48 h after transfection and the peptides purified as described previously (Noël et al., 1989). The presence of β-endorphin in the extracts was detected by radioimmunoassay. The results showed that both COS-1 and HEK 293 cells produced approximately 100 pg of β-endorphin per ml of culture medium. Therefore, the N-terminus of LN-1 and NL-2 which ends with a furin-recognition site will be useful to produce the soluble form of a protein of interest.

Section 2)

Materials and Methods

DNA manipulations

All DNA manipulations, phage library screening, and plasmid preparations were performed according to standard protocols (Ausubel 1988; Sambrook 1989). Site-directed mutagenesis was performed using a PCR-based strategy as described previously (Le Moual 1994).

mRNA purification and RT-PCR protocol for identification of new members of the neprilysin family mRNAs were prepared from mouse testis using Quick Prep Micro mRNA purification kit (Pharmacia Biotech). First strand cDNA was synthesized from 1 μg of mRNA using the First-Strand cDNA synthesis kit (Pharmacia Biotech).

Two sense primers, oligonucleotide 3817 (5'-TGGATG-GAT/CGA/CIGG/AIACIA/CA-3') and oligonucleotide 3719 (5'-A/GTIGTITTT/CCCIGCIGGIA/GT/AIC/TTG/CCA-3') corresponding respectively to amino acid residues 459 to 465 and 552 to 560 of NEP sequence, and one antisense primer, oligonucleotide 3720 (5'-AIICCICCIA/TC/TA/GTCIGCIG/AC/TA/GTTT/CTC-3') corresponding to amino acid residues 646 to 654 (see FIGS. 1 and 2), were synthesized. PCR was performed with 5 μl of cDNA template and 1 μl of Taq DNA polymerase in a final volume of 100 μl, containing 1 mM MgCl$_2$, 2 μM of each oligonucleotide 3817 and 3720, 200 μM of each dNTP and 5% DMSO. Cycling profiles included an initial denaturation step of 5 min at 94° C., 30 cycles of 1 min at 94° C., 1 min at 40° C. and 1.5 min at 72° C., and a final extension step at 72° C. for 10 min. One half of the amplified DNA was fractionated on a 2% agarose gel and fragments ranging in size between 500–700 bp were purified and resuspended in a final volume of 50 μl. A second round of PCR was done with primers 3719 and 3720, using as template either 10 μl of the first PCR reaction or 5 μl of the purified fragments, and the new PCR products were ligated in pCR2.1 vector (Invitrogen). Several identical clones corresponded to a potential new member of the NEP family. We called this member NL1 for NEP-like 1.

Cloning of full-length NL1 cDNA

The cloned NL1 PCR fragment was used as probe to screen a mouse testis λ Uni-ZAP™XR cDNA library (Stratagene). Twelve out of a hundred positive phages were plaque purified and subcloned into pBS SK vector (Stratagene). As the longest clone analyzed presented an incomplete ORF (pBS-NL1A), 5'RACE with primers located in vector (5'-TAGTGGATCCCCCGGGCTGCAG-3', sense primer) and NL1 (5'-ACCAAACCTTTCCTGTAGCTCC-3', antisense primer, nt 1303 to 1324 of NL1; was subsequently performed on the DNA of the remaining semi-purified positive clones. Amplification was performed with 1 μl of Vent polymerase in a final volume of 100 μl containing 50 ng of DNA, 4 mM of MgSO$_4$, 1 μM of each oligonucleotide, 200 μM of each dNTP and 10% DMSO. Cycling parameters included an initial denaturation step of 1 min at 94° C., 25 cycles of 30 sec at 94° C., 30 sec at 60° C. and 1 min at 72° C., and an incubation of 10 min at 72° C. A PCR fragment of the expected length was subcloned into pCR2.1 vector (clone pCR-NL1A), but sequencing revealed no initiator ATG codon. A nested 5'RACE was then performed on mouse testis cDNA using the Marathon Ready cDNA kit (Clontech) with sense oligonucleotides AP1 and AP2 (from the kit) and NL1 antisense oligonucleotides 5'-CCTGAGGGCTCGTTTTACAACCGTCCT-3' (nt 503 to 529 of NL1) and 5'-CTCATCCCAGGAGAAGTGTAG-CAGGCT-3' (nt 475 to 502 of NL1) as recommended by the supplier. The resulting fragment was cloned into pCR2.1 vector (pCR-NL1B). Since only ten bp were missing for the initiator ATG codon, we reconstructed the 5' end of the cDNA by PCR-amplifying clone pCR-NL1A with sense primer 5'-CCACC ATGGTGGAGAGAGCAGGCTGGTGTCGGAAGAAG-3' (nt 332 to 364 of NL1; the 10 missing nucleotides are underlined) and antisense primer 5'-ACCAAACCTTTCCT-GTAGCTCC-3' (nt 1303 to 1324 of NL1) using Vent polymerase as described above. The DNA fragment was then inserted into pCR2.1 (clone pCR-NL1C). The entire ORF was reconstituted following digestion of pBS-NL1A and pCR-NL1C with EcoRI and PflMI. The 5' end of NL1 cDNA was excised from pCR-NL1C and ligated into pBS-NL1A at the corresponding sites, resulting in plasmid pBS-NL1B. For expression studies, a BamHIIApal fragment generated out of pBS-NL1B, corresponding to the full length cDNA of NL1, was inserted into pCDNA3/RSV [18] vector.

Production of polyclonal antibodies

A plasmid for the production in *Escherichia coli* of a GST fusion protein with NL1 was constructed using pGEX-4T-3 expression vector (Pharmacia Biotechnologies). A 255 bp fragment from NL1 was amplified by PCR with Vent polymerase using sense primer 5'-GCTACG GGATCCGTGGCCACTATGCTTAGGAA-3' (nt 1139 to 1158) and antisense primer 5'-CGATTG CTCGAGTGGGMCAGCTCGACTTCCA-3' (nt 1377 to 1396). Both pGEX-4T-3 and the PCR product were digested with BamHI and XhoI and ligated. The recombinant protein was produced and purified according to the supplier's instructions. Five weeks old female balb/c mice were immunized at monthly intervals for 3 months with 20 μg of the recombinant NL1 fragment in Freund's adjuvant and antisera were subsequently collected.

Cell culture and transfection

Human Embryonic Kidney (HEK 293) cells were maintained in DMEM medium containing 10% fetal bovine serum (FBS), and supplemented with penicillin at 60 µg/ml, streptomycin at 100 µg/ml and fongizone at 0.25 µg/ml. Transfections of cells with appropriate plasmids were performed by the calcium/phosphate-DNA co-precipitation method (Chang 1987). To establish permanent cell lines, G418 selection was initiated 48 h after the transfections at 400 –82 g/ml for 12 days and gradually decreased at 100 µg/ml.

LLC-PK, cells transfected with pRcCMV-sNEP were maintained as described previously (Lanctot 1995).

Immunoblot analysis

For immunoblot analysis, cells were incubated for 16 h in synthetic DMEM medium containing 2 mM sodium butyrate. Cellular proteins were solubilized as previously described (Dion 1995). Secreted proteins recovered in culture media were concentrated approximately 10 fold by ultrafiltration. Immunoblot analysis were performed using the NEN Renaissance kit with the polyclonal antibody specific to NL1 or the α1-antitrypsin inhibitor antibody (Calbiochem; LaJolla, Calif.) followed by the appropriate horseradish peroxidase-conjugated IgG (Vector Laboratories).

For the glycosylation studies, proteins were incubated with endoglycosidase H (endoH) or peptide:N-glycosidase (PNGaseF) as suggested by the distributor (NEB).

Enzymatic activity assays

NL1 activity was monitored and compared to sNEP activity using (Tyrosyl-[3,5-$^3$H])(D-Ala$_2$)-Leu$_5$-enkephalin (50 Ci/mmol) (Research Products International Inc.), as already described (Dion 1995; Devault 1988). $K_m$ values were determined by the isotope-dilution method. The inhibitory effects of phosphoramidon and thiorphan were also assessed as previously described (Dion 1995).

HPLC analysis of the hydrolysis of Leu-enkephalin

Five µg of Leu$_5$-enkephalin were incubated at 37° C. for one hour in 50 mM MES, pH 6.5, with concentrated culture medium of HEK 293 cells expressing NL1 (~300 µg of total proteins) or LLC-PK$_1$ cells expressing sNEP (~30 µg of total proteins), in absence or presence of 0.1 mM phosphoramidon. Hydrolysis products were separated by reversed-phase HPLC as described previously [23]. Tyr-Gly-Gly and Phe-Leu were both identified by elution profiles of synthetic marker peptides.

Northern blot analysis

A mouse multiple tissue poly(A)$^+$ mRNA blot (Clontech) was hybridized with a [$^{32}$P]dCTP random primer labelled probe in ExpressHyb solution (Clontech). The blot was washed according to the manufacturer's recommendations and exposed to Fuji RX film for 7 days at –80° C. with intensifying screens.

RT-PCR screening of mouse tissues

First strand cDNA synthesis was performed with 1 µg of total RNA from mouse tissues and oligo(dT) as primer, using Gene Amp RNA PCR Core Kit (Perkin Elmer). For the PCR reactions, primers 5'-TGGCGAGAGTGTGTCAGCTAT-GTC-3' and 5'-CTTCCAAAATGTAGTCAGGGTAGC-CAATC-3' were used with Taq polymerase. One tenth of the PCR products were visualized on a 4% agarose gel.

In situ hybridization

To construct a plasmid for the synthesis of cRNA probes for ISH, pCR-NL1A was used as template to amplify a 452 bp fragment by PCR with sense primer 5'-GGAGCCAT-AGTGACTCTGGGTGTC-3' (nt 416 to 439) and antisense primer 5'-GACGCTCAGCAGGGGCTCAGAGTC-3' (nt 842 to 865). The amplification product was inserted into pCRII vector (Invitrogen). Synthesis of riboprobes and protocols for ISH were as described previously (Ruchon 1998).

Results

Cloning and sequence analysis of mouse NL1 cDNA

In order to isolate cDNAs for new members of the NEP family, we developed an RT-PCR strategy based on fact that NEP, ECE-1 and PHEX share regions of significant sequence identity. Following RT-PCR on testis mRNAs with nested primers, a DNA fragment of approximately 300 bp was amplified. This DNA fragment was cloned and the plasmids from 24 independent colonies were sequenced: 3 clones had no insert, 4 clones had DNA fragments not related to the NEP family, 7 clones had sequences corresponding to mouse NEP and 3 clones had sequences corresponding to mouse PHEX, showing that our approach efficiently allowed the identification of members of the family. Moreover, 7 identical clones had a new cDNA presenting sequence similarities to members of the NEP family. The full-length cDNA was subsequently obtained by screening a mouse testis λ cDNA library followed by 5'RACE, as described under Materials and Methods. Its nucleotide and deduced amino acid sequences confirm that we cloned a novel NEP-like protein, referred to thereafter as NL1.

NL1 cDNA spans 2925 nt, including a 5'-untranslated region of 331 nt, an open reading frame of 2295 nt from nt 332 to nt 2626, and a 3'-untranslated region of 299 nt. The sequence surrounding the proposed initiator ATG conforms to the Kozak consensus (Kozak 1986). The deduced amino acid sequence of NL1 reveals a putative type 11 transmembrane protein of 765 amino acid residues encompassing a short N-terminal cytoplasmic tail, a unique putative transmembrane domain, and a large C-terminal extracellular domain. The ectodomain contains nine potential N-glycosylation sites (Asn-X-Ser/Thr) and ten cysteine residues corresponding to those conserved among all the members of the family, which are presumably involved in proper folding and in maintenance of the protein in an active conformation. All amino acid residues known to be part of the active site of NEP are present in NL1. The predicted protein presents greater similarities to NEP than to any other member of the family. Although NL1 shares numerous features with proteins of the neprilysin family, a notable aspect distinguishes it from the others: the first conserved cysteine residue of the ectodomain is more distant (34 amino acid residues) from the predicted transmembrane domain in NL1 than it is in NEP (9 residues) or any other members of the family. Moreover, we noticed a putative furin cleavage site (-Arg$_{58}$-Thr-Val-Val-Lys-Arg$_{63}$-) between the end of the transmembrane domain and the first cysteine. This observation suggests that NL1 could exist as a secreted rather than a membrane-bound protein.

NL1 expression in HEK 293 cells

HEK 293 cells were transfected with pCDNA3/RSV expression vector containing NL1 cDNA, and a permanent cell line was established as described under *Materials and Methods* (HEK/NL1 cells). Immunoblotting with a polyclonal antibody showed that after 16 h of culture, most NL1 was present in the culture medium with small amounts of the enzyme in the cell extract. Secreted and cell-associated NL1 had apparent molecular masses of approximately 125 and 110 kDa, respectively. To characterize the glycosylation state of NL1, we next submitted the recombinant protein to deglycosylation by peptide:N-glycosidase F (PNGase F) and endoglycosidase H (endo H). PNGase F removes high mannose as well as most complex N-linked oligosaccharides added in the Golgi complex. In contrast, endo H removes N-linked oligosaccharide side chains of the high mannose type found on proteins in the RER but which have not yet transited through the Golgi complex; thus, resistance to endo H can be used as an indication that the protein has traveled through the Golgi complex. PNGase F treatment showed that the cell-associated and secreted NL1 were N-glycosylated as their electrophoretic mobility increased following digestion. However, the secreted NL1 migrated as a doublet after PNGase F treatment, with one band co-migrating with cell-associated form and the second having a slower rate of migration. Since untreated and endo H-digested secreted NL1 are seen as single bands by SDS-PAGE, our observation suggests that a proportion of secreted NL1 undergoes further post-RER postranslational modification that renders some of the N-linked oligosaccharides resistant to PNGase F digestion.

In contrast to secreted NL1, NL1 from cell extract was sensitive to endo H treatment. This result shows differences in the glycosylation state of the two species and suggests that the cell-associated form observed in transfected cells is an intracellular species that has not traveled through the Golgi complex.

Processing of NL1 by a subtilisin-like convertase

To determine whether a member of the mammalian subtilisine-like convertase family is responsible for NL1 presence in the culture medium of transfected cells, we co-transfected transiently HEK 293 cells with a constant amount of plasmid pCDNA3/RSV/NL1 and increasing amounts of plasmid pCDNA3/CMV/PDX (Benjannet 1997). This latter vector promotes the expression of the α1-antitrypsin Portland variant, α1-PDX, a known inhibitor of subtilisin-like convertases (Anderson 1993). Immunoblot analysis of the culture media of cells expressing both NL1 and α1-PDX indicated that NL1 secretion was strongly inhibited by the presence of α1-PDX: a relation was observed between the amounts of α1-PDX and the level of inhibition of NL1 secretion.

To confirm that proteolysis by the subtilisin-like convertase occurred at the putative furin cleavage site identified in NL1 ectodomain (-$Arg_{58}$-Thr-Val-Val-Lys-$Arg_{63}$-), the amino acid residues $Asn_{62}$-$Gly_{63}$ were substituted for $Lys_{62}$-$Arg_{63}$ by site-directed mutagenesis in vector pCDNA3/RSV/NL1 and the mutated vector used to establish HEK 293 cells expressing the mutant protein (HEK/NL1mut cells). Immunoblot analysis of the culture media of HEK/NL1 mut cells showed that the mutation totally abolished secretion of NL1. Furthermore, an additional form of NL1 with a molecular mass of 127 kDa was detected in the extract of these cells. This new species was resistant to endo H digestion and was found associated with membranes when HEK/NL1mut cells were fractionated according to Chidiac et al. 1996 (result not shown).

NL1 enzymatic activity

Culture media from HEK 293 and HEK/NL1 cells were tested for enzymatic activity using as substrate (Tyrosyl-[3,5-$^3$H](D-$Ala_2$)-$Leu_5$-enkephalin, a known NEP substrate. Activity was detected in the culture medium of HEK/NL1 cells but not in that of HEK 293 cells. This activity increased linearly with the amounts of NL1 and with the incubation period, indicating that degradation of the substrate was due to NL1 enzymatic activity.

We next characterized NL1 enzymatic parameters using the same substrate and compared them to those of an engineered soluble form of NEP (sNEP) (Lemay 1989). NL1 affinity for D-$Ala_2$-$Leu_5$-enkephalin was slightly higher than that of sNEP as shown by their $K_m$ values of 18 μM and 73 μM, respectively. Inhibition assays showed that phosphoramidon had similar effects on NL1 and sNEP activity, with $IC_{50}$ values of 0.9 nM and 0.5 nM respectively, and that thiorphan, a specific inhibitor of NEP, inhibited NL1 with an $IC_{50}$ of 47 nM, as compared with an $IC_{50}$ of 8 nM for NEP.

Very low levels of phosphoramidon-sensitive activity was detected in extracts of HEK/NL1 cells (data not shown) consistent with the small amounts of NL1 observed by immunoblotting.

To determine whether NL1 had cleavage site specificity similar to NEP, we incubated $Leu_5$-enkephalin in the presence of NL1 recovered from the medium of HEK/NL1 cells or in the presence of sNEP, and analyzed the degradation products by RP-HPLC. Peaks co-migrating with standard Tyr-Gly-Gly and Phe-Leu peptides were observed in both RP-HPLC profiles, indicating that both enzymes cleaved the substrate at the $Gly_3$-$Phe_4$ peptide bond. This enkephalin-degrading activity was completely inhibited by phosphoramidon (1 μM).

Tissue and cellular distribution of NL1 mRNA

Tissue distribution of NL1 mRNA was determined by Northern blot analysis with a specific probe corresponding to the 5'end of the coding region of NL1 cDNA. A single transcript of 3.4 kb was detected exclusively in testis among all the mouse tissues tested. Mouse tissues were also screened by RT-PCR. Using this more sensitive technique, expression of NL1 was observed in several other tissues including heart, brain, spleen, lungs, liver and kidney. Consistent with the Northern blot results, RT-PCR analysis, although not strictly quantitative, detected more NL1 mRNA in testis than in other tissues.

To gain more insight into NL1 mRNA distribution, we examined by ISH cryostat sagital sections from a 4-day newborn mouse, as well as sections from a 16-day old animal (p16) and adult tissues (heart, brain, spleen, lungs, liver, kidney and testis). The presence of NL1 mRNA was detected only in adult testis. Only the germinal cells in the luminal face of the seminiferous tubules were labeled. These cells were identified as round and elongated spermatids in all spermiogenesis maturational stages. Neither spermatozoa nor spermatocytes, spermatogonies or Sertoli cells were labeled. Interstitial cells were also negative. Controls were performed with sense riboprobes, which produced only nonspecific background (data not shown). The 4-day old mouse sagital sections and all other tissues tested were negative.

Discussion

The great interest in members of the Neprilysin family as putative therapeutic targets, and the recent discovery of new members of this important family of peptidases led us to investigate whether additional members of the family remained to be identified. Using a PCR-based strategy, we cloned, from mouse testis, a partial cDNA encoding a new NEP-like enzyme that we called NL1. Analysis of the amino acid sequence encoded by the full-length NL1 cDNA revealed that this member of the family resembles NEP the most: 55% identity and 74% similarity. Recently, the primary structure of a new zinc metallopeptidase from total mouse embryo was reported (Ikeda 1999). This enzyme, called SEP, is found either as a soluble or a cell-associated form due to alternative splicing. NL1 shows only 3 amino acid differences with the soluble form of SEP indicating that secreted SEP and NL1 are the same enzyme. Our cloning strategy did not allow characterization of the cell-associated form of NL1 which is a minor species in mouse testis (Ikeda 1999).

The amino acid sequence of NL1 predicts a topology of a type II integral membrane glycoprotein that is similar to the other members of the family. Treatment of the recombinant protein with PNGase F showed that indeed NL1 possesses N-linked carbohydrate side chains. However, it is not possible to determine precisely whether all nine putative N-glycosylation sites are used, but the 30 kDa decrease in molecular mass upon PNGase F treatment suggests that most are glycosylated. It has already been shown that all asparagine residues in a Asn-X-Ser/Thr consensus are glycosylated in rabbit NEP expressed in COS-1 cells and that sugar moieties increase the stability and enzymatic activity of the protein and facilitate its intracellular transport (Lafrance 1994). Three of NEP glycosylated Asn residues (Asn 145, Asn 285 and Asn 628) are conserved in NL1 (Asn 163, Asn 303 and Asn 643). Amongst these residues, Asn 145 and Asn 628 have been reported to influence NEP enzymatic activity (Lafrance 1994). In the same work, it has also been shown that the effect of sugar addition on folding and intracellular transport of NEP is a cumulative effect of all glycosylation sites rather than a contribution of any particular one. Glycosylation of NL1 may share similarities with that of NEP since we found their primary structures and enzymatic activities to be very similar.

Surprisingly, expression of the cDNA by transfection of HEK 293 cells showed that most of the enzyme was secreted in the culture medium. The small amount of NL1 associated with the cells was endo H-sensitive, suggesting that the cell-associated enzyme is a species that has not yet left the RER. The presence of a furin cleavage site in NL1 sequence between the predicted transmembrane domain and the first conserved cysteine residue of the ectodomain led us to believe that a member of the mammalian subtilisin-like family of convertases was responsible for the presence of NL1 in the culture medium. These enzymes are involved in processing a variety of precursor proteins such as growth factors and hormones, receptors, plasma proteins, matrix metalloproteinases, metalloproteases-desintegrins and viral envelope glycoproteins [for a review see: (Nakayama 1997). Site-directed mutagenesis of the furin cleavage site (-$Arg_{58}$-Thr-Val-Val-Lys-$Arg_{63}$-) and expression of α1-PDX, a potent inhibitor of mammalian subtilisin-like convertases (Anderson 1993), confirmed that a member of this family of endoproteases was involved in NL1 secretion presumably by cleaving in carboxy-terminus of $Arg_{63}$. There are only a few examples of proteins which are processed from a membrane-bound precursor to a secreted form following cleavage by subtilisin-like convertases; these include meprin and collagen XVII (Milhiet 1995; Schacke 1998). Three members of the subtilisin-like family of convertases, namely furin, PC4 and PC7, are known to be expressed in germ cells (Nakayama 1992; Torri 1993; Seidah 1992, 1996). Whether one of these convertases generates secreted NL1 from its membrane form is under current investigation. In any case, NL1 is the only known member of the neprilysin family that is secreted. This unique feature suggests that NL1 plays its physiological role in a context different from that of the membrane-bound peptidases, thereby diversifying the role of the peptidases of the neprilysin family. It is of interest that circulating forms of NEP in blood and urine have been described, but they have generally been related to pathological or stressful conditions (Almenoff 1984; Deschodt-Lanckmann 1989; Johnson 1985; Soleilhac 1996; Aviv 1995).

We have observed in cells expressing NL1 mutated at the furin cleavage site the appearance of a species resistant to digestion by endo H. This mutated protein was associated with cellular membranes. Taken together, these results indicate that NL1 is first synthesized and inserted in the RER membrane as a type II transmembrane protein. During intracellular transport, NL1 is converted to a soluble form by the action of a member of the mammalian subtilisin-like convertases. The identity of the cellular compartment where this process occurs is not known. However, mammalian subtilisin-like convertases are usually active in post-Golgi compartments of the secretory pathway suggesting that processing of NL1 from the membrane bound form to the soluble form is a post-Golgi event.

Despite almost total abrogation of NL1 secretion, we observed only a slight accumulation of endo H-resistant NL1 in cells either co-expressing α1-PDX and NL1 (result not shown) or expressing mutated NL1. This observation suggests that unprocessed NL1 is rapidly degraded. A similar behavior was reported for the Notch1 receptor expressed in the furin-deficient cell line LoVo (Logeat 1998). The mechanism(s) by which these unprocessed proteins are degraded is still unknown. It is interesting to point out that the spliceoform of SEP that has lost a 23 amino acid peptide, including the furin cleavage site, generates a cell-associated endo H-sensitive molecule (Ikeda 1999).

The most important observation regarding the NL1 primary structure is the conservation of residues which in NEP are essential for catalysis and binding of substrates or inhibitors. This finding suggests that NL1 could effectively act as an endopeptidase with a catalytic mechanism similar to that of NEP. This hypothesis was supported by the demonstration that D-$Ala_2$-$Leu_5$-enkephalin, a peptide substrate often used to monitor NEP activity, was also an excellent NL1 substrate. The affinity of NL1 for D-$Ala_2$-$Leu_5$-enkephalin was even higher than that of NEP, as reflected by a $K_m$ value 4- to 5-fold lower. Furthermore, two well known NEP inhibitors, phosphoramidon and thiorphan, also abolished NL1 activity. Phosphoramidon, which inhibits NEP as well as ECE-1 activity, albeit to a lesser extent (Turner 1996), had very similar effects on NL1 and NEP, with an $IC_{50}$ value for NL1 varying not more than two-fold from the value determined for NEP. Thiorphan, considered to be a more specific inhibitor of NEP, also inhibited NL1 activity, with an $IC_{50}$ six-fold greater than that for NEP. These results suggest that the active sites of NL1 and NEP are similar. This hypothesis is supported by the observation that secreted SEP degraded a set of peptides known to be NEP substrates, including substance P, bradykinin and atrial natiuretic peptide (Ikeda 1999). Taken together, these results illustrate the importance of identifying and characterizing other member of the family for the design of highly specific inhibitors.

In agreement with the enzymatic parameters demonstrating that NL1 and NEP have similar catalytic sites, we have observed that both enzymes cleaved $Leu_5$-enkephalin at the same peptide bond. This result suggests that NL1 hydrolyzes peptide bonds on the amino side of hydrophobic amino acid residues as does NEP (Turner 1985). However, several other peptides will have to be tested to confirm this specificity and to determine whether NL1 has dipeptidyl carboxypeptidase activity as was shown for NEP (Malfroy 1982; Bateman 1989; Beaumont 1991) and more recently for ECE-1 (Johnson 1999).

RT-PCR experiments with specific primers for the soluble and cell-associated forms of SEP showed a wide tissue distribution of the enzyme with the soluble form of SEP being predominant in testis and the cell-associated form in other tissues (Ikeda 1999). Our RT-PCR results confirmed the wide tissue distribution of NL1. However, Northern blotting and in situ hybridization experiments indicated that expression of NL1 is predominant in germ cells of mature testis. Interestingly, proenkephalin mRNA has been shown to be expressed in germ cells and somatic cells of the testis (Torii 1993, Seidah 1992; Kew 1989; Mehta 1994; Kilpatrick 1986, 1987). Specific functions for testicular enkephalin peptides have not yet been defined, but it is believed that they could act as intratesticular paracrine/autocrine factors. In addition to their putative role as mediators of testicular cell communication, it has also been demonstrated that proenkephalin products synthesized by spermatogenic cells during spermatogenesis are stored in the acrosome of human, hamster, rat and sheep spermatozoa and are release from sperm following acrosomal reaction (Kew 1990). It has thus been proposed that proenkephalin products may act as sperm acrosomal factors during the fertilization process as well as intratesticular regulators secreted by spermatogenic cells. Since $Leu_5$-enkephalin was found to be a good substrate for NL1, opioid peptides originating from proenkephalin could serve as physiological substrate for this new enzyme. In this way, NL1 would serve to regulate the activity of these bioactive peptides.

Testis is the only tissue where the soluble form of SEP is predominant (Ikeda, 1999), suggesting a testis-specific alternative splicing. Expression of testis-specific molecular species of peptidases or prohormones, arising through diverse mechanisms, has been documented in the past (Howard 1990; Jeannotte 1987). However, the physiological significance of these testis-specific species is not always clear. In the case of NL1 or SEP, it might allow local constitutive secretion by germinal cells of an otherwise cell-associated enzyme, to regulate spermatogenesis much like several other proteolytic enzymes of the seminiferous tubules (Monsees 1998). Alternatively, it might allow accumulation in acrosome with proenkephalin peptides and release upon acrosomal reaction. More exhaustive studies concerning NL1 localization and physiological substrate identification will be needed to understand its role in the testis and possibly in the fertilization process.

Cloning of other members of the family

To find other members of the NEP-like family, we will use the same RT-PCR strategy to amplify mRNA isolated from tissues known to be regulated by peptidergic systems (brain, thymus, kidney, heart, lung, ovary, pancreas, bone, bone marrow and lymphoid cells). In fact, many of these tissues are known to express at least one member of the family and/or to control a peptidergic pathway on which peptidase inhibitors have major effects. Amplified fragments will be cloned and the resulting clones will be sequenced and compared to the sequence of known peptidases, as described above. Pairs of degenerate primers in other highly conserved regions will also be designed to increase the possibility of cloning other relevant peptidases.

DISCUSSION

As discussed above, peptidases of the NEP family known to date have often been found to play important physiological roles. This is certainly true for NEP itself, ECEs and PEX, (see review above). For this reason, some of these enzymes (as it was the case for NEP and ECE in the past) might be interesting targets for the design of inhibitors that in turn could be used as therapeutic agents in various pathological conditions. However, it is of some concern that inhibitors designed for one enzyme may also inhibit to some extent other members of the family. This lack of specificity for an inhibitor used as a therapeutic agent in the long term treatments such as those used as antihypertensive agents for instance, may cause unforeseen problems due to unwanted side effects. The objectives of the present work was to develop a strategy to clone new members of the NEP family of peptidases. The results presented in this report clearly show that our strategy can be successful. We have determined the complete or partial nucleotide sequence of three cDNAs encoding putative enzymes of the NEP family.

These cDNA sequences are valuable tools and may be used to:

Produce antibodies

As shown in the present work, knowledge of NL cDNA sequences can be used to raise specific antibodies. For example but not exclusively, regions of less homology between the peptidases (amino acid residues 50 to 450) can be used to synthesize peptides whose sequences are deduced from the translation of the cDNAs, and/or bacterially-expressed fragments of the cDNAs fused for example but not exclusively to GST may be purified and injected into rabbits or mice for polyclonal or monoclonal antibody production. These antibodies can be used to:

identify by immunohistochemistry the peptidergic pathways in which the peptidases are functioning;

study the physiopathology of NL-enzymes by immunoblotting or immunohistochemistry on samples of biological fluids or biopsies;

set up high through put screening assays to identify NL-enzymes inhibitors. This can be done for example but not exclusively by using the antibodies to attach the NL-enzymes to a solid support;

purify NL-enzymes with said antibodies by immunoprecipitation or affinity chromatography by identifying antibodies capable of selectively binding to the NL-enzymes in one set of conditions and releasing it in another set of conditions typically involving a large pH or salt concentration change without denaturing the NL-enzyme;

identify antibodies that block NL-enzymes activities and use them as therapeutic agents. Blocking antibodies can be identified by adding antisera or ascite fluid to an in vitro enzymatic assay and looking for inhibition of NL-enzymes activities. Blocking antibodies could then be injected to normal or disease model animals to test for in vivo effects.

Derive specific RNA or DNA probes

As shown in the present work, knowledge of the nucleotide sequence of the members of the NEP-family allows nucleotide sequence comparisons and facilitate the design of specific RNA or DNA probes by methods such as but not exclusively molecular cloning, in vitro transcription, PCR or DNA synthesis. The probes thus obtained can be used to:

derive specific probes or oligonucleotides for RNA and DNA analysis, such as Northern blot and in situ hybridization, chromosome mapping or PCR testing.

These probes could be used for genetic testing of normal or pathological samples of biological fluids or biopsies;

make vectors for gene knock-out or knock-in in mice. The long range PCR technique and/or screening of a mouse genomic library with probes derived from the 5'-end of the cDNAs can be used to isolate large exon/intron regions. We will then substitute one or more of the cloned genomic DNA exons for the neomycin resistance expression cassette for producing homologous recombination and knock-out mice. Alternatively, cDNAs coding for NLs will be used to overexpressed each of these enzymes in transgenic mice. The cDNAs will be cloned downstream from a promoter sequence, and injected in fertilised mouse eggs. Depending on specific questions to be answered, the chosen promoter sequence will allow expression of the peptidases either in every tissues or in a cell- or tissue-specific manner. Injected eggs will be transferred into foster mothers and the resulting mice analysed for peptidase expression;

replace defective NL genes in a gene therapy strategy. The NL full length cDNAs could be cloned under the control of a constitutive or inducible promoter having a narrow or wide range of tissue expression and introduced with appropriate vectors in subjects having defective genes;

synthesise oligonucleotides that could be used to interfere with the expression of the NLs. For example but not exclusively, oligonucleotides with antisens or ribozyme activity could be developed. These oligonucleotides could be introduced in subjects as described above;

isolate other members of the family. Screening cDNA and/or genomic libraries with these cDNA probes at low stringency may allow to clone new members of the NEP-like family. Alternatively, alignment of the sequences may allow one to design specific degenerate oligonucleotide primers for RT-PCR screening with mRNA from tissues such as but not exclusively, the hearth and the brain.

Production of recombinant NL-enzymes

As shown in the present work, recombinant active NL-enzymes can be obtained by expression of NL-cDNAs in mammalian cells. From past experience with neprilysin, another member of the family (Devault et al., 1988; Fossiez et al., 1992; Ellefsen et al., submitted), expression can also be performed in other expression systems after cloning of NL-cDNAs in appropriate expression vectors. These expression systems may include but not exclusively the baculovirus/insect cells or larvae system and the *Pichia pastoris*-based yeast system. Production of recombinant NL-enzymes includes the production of naturally occurring membrane bound or soluble forms of the proteins or genetically engineered soluble forms of the enzymes. The latter can be obtained by substituting the cytosolic and trans-membrane domain by a cleavable signal peptide such as that of proopiomelanocortin, but not exclusively, as done previously (Lemay et al., 1989) or by transforming by genetic manipulations the non-cleavable signal peptide membrane anchor domain into a cleavable signal peptide, as done previously (Lemire et al., 1997) or by fusion of the ectodomain of NL-enzymes to the amino-terminal domain (from the initiator methionine to amino acid residue 300) of naturally occurring soluble NLs such as, but not exclusively, NL-1 as done in this work. These recombinant NLs could be used to:

find a substrate. A substrate can be identified using one of the following.

Screening of existing bioactive peptides. Peptides are incubated in the presence of NL-enzymes and subsequently analysed by HPLC for degradation. Degradation is observed by disappearance of the peak of substrate and the appearance of peaks of products;

Screening phage libraries specifically designed for the purpose (phage display library). Each phage expresses at its surface, as part of its coat protein, a random peptide sequence preceded by a peptide sequence recognisable by an antibody or any other sequence-recognizing agent. This latter sequence serves to attach the phage to a solid support. Upon addition of the NL-enzyme the random sequences that are NL substrate are cleaved, releasing the phage. After several rounds of cleavage, the phage sequence is determined to identify the peptide segment recognized by the enzyme.

Extract of the tissue where the enzyme is expressed is collected and prepared for chromatographic analysis (HPLC, capillary electrophoresis or any other high resolution separation system) by denaturing the extracted proteins with a solvent (acetonitrile or methanol). The extract is subjected to chromatographic separation. The same extract is incubated with the enzyme for a period sufficient to observe a difference between the 2 chromatograms. The regions with the identified changes are collected and subjected to mass spectrometric analysis to determine the peptide compositions.

Small peptide libraries are prepared with a fluorophore at one extremity and a quencher group at the other (Meldal et al Methods in molecular biology 1998, 87). The substrate can be identified using a strategy described in Apletalina et al (JBC (1998)273, 41, 26589–95). For each hexapeptide library, the identity of one residue at one position remains constant while the rest is randomized (for a total of 6*20=120 individual libraries). Each library is made-up of 3.2 million different members and is identified both by the position of the constant residue along the hexapeptide, and its identity. The NL-enzyme is added to each library and the fluorescence is recorded. The data is organized to identify the libraries producing the most fluorescence for each position along the hexapeptide. This arrangement suggests the identity of important residues at each position along the hexapeptide. Hexapeptide representing the best suggestions are prepared and tested in a similar fashion. From this set, the hexapeptide with the best fluorescence is selected.

set up enzymatic assays. An enzymatic assay consists in the addition of the above-identified substrate to the enzyme in constant conditions of pH, salts, temperature and time. The resulting solution is assayed for the hydrolysed peptide or for the intact peptide. This assay can be realized with specific antibodies, HPLC or, when self-quenched fluorescence tagged peptides are used (Meldal et al), by the appearance of fluorescence. The enzyme may be in solution or attached to a solid substrate;

identify inhibitors. Inhibitors can be identified from synthetic libraries, biota extracts and from rationally designed inhibitors using X-ray crystallography and substituent activity relationships. Each molecule or extract fraction is tested for inhibitory activity using the enzymatic test described above. The molecule responsible for the largest inhibition is further tested to determine its pharmacological and toxicological properties following known procedures. The inhibitor with the best distribution, pharmacological action combined with low toxicity will be selected for drug manufacturing. Pharmaceutically acceptable formulation of the inhibitor or its acceptable salt will be prepared by mixing with known excipients to produce tablets, capsules or injectable solutions. Between 1 and 500 mg of the drug is administered to the patients;

inject the native or soluble purified NL-enzymes into subjects. In the case of disease or pathologies caused by a lack or decrease in NL activity, the purified NL could be injected intravenously or otherwise in patients. Alternatively, immobilized NL-enzymes could be introduced at the site of orthopedic surgery or implantation of devices in bones or dental tissues.

Secretion of foreign proteins and peptides

As shown in the present work, the amino-terminal domain of NL-1 (from the initiator methionine to the furin site) can be used to promote the secretion of a foreign protein (in this case the ectodomain of NL-3 and β-endorphin).

The amino-terminal domain of NL-1 but also of other naturally occurring soluble

NL-enzymes could be used to:
  promote production and secretion of foreign proteins. This can be achieved by genetically fusing sequences coding for said foreign proteins downstream from and in phase with the amino-terminal of NL-1. These chimeric constructs could be introduced with the help of appropriate vectors in any of the expression systems mentioned above for protein production and secretion;
  promote production and secretion of bioactive peptides. Sequences encoding small bioactive peptides such as but not exclusively β-endorphin, the enkephalins, substance P, atrial natriuretic peptide (ANF) and osteostatine, could be fused immediately downstream and in phase the furin site of NL-1. These DNA constructs could be used as described above to produce bioactive peptides.
  serve as model to design artificial (non-naturally occurring) proteins or protein segments (protein vectors) to promote secretion of proteins or peptides. These protein vectors can be constructed to resemble a secreted protein. In this case they would be assembled of an endoplasmic reticulum signal peptide, a spacer of varying length and a furin cleavage site to which the protein or peptide destined for secretion can be fused. The total length of the spacer, furin cleavage site and protein or peptide destined for secretion must be at least 70 amino acid residues. Alternatively, such protein vectors could be assembled to resemble a type II membrane protein. In this case they would comprise from the amino to the carboxy-terminus a cytosolic domain of varying length, a transmembrane domain that also acts as a signal peptide, an extracellular segment of varying length and a furin cleavage site to which the protein or peptide destined for secretion can be fused. The total length of the extracellular segment, furin cleavage site and protein or peptide destined for secretion must be at least 70 amino acid residues.

Therapeutic applications of NL-enzymes

The inappropriate processing of endogenous peptides causes several diseases. The inappropriate processing may result from pathologic concentration of the enzyme itself, its substrate or other elements of the biochemical machinery downstream from the controlling enzyme. In this context it is possible to help the patient by managing the activity of the controlling enzyme.

NL-enzymes have been localized to the brain and may be involved in the improper processing of β-amyloid precursor. Inhibitions of this process by drugs prepared as above, will help patients with Alzheimer disease as well as other patient suffering from diseases caused by plaque formation;
  NL-enzymes may be involved in the improper processing of other peptides involved in neurological diseases, pain or psychiatric disorders. Appropriately designed inhibitors will help in the management of such diseases;
  NL-1 is found in testis and is associated with spermatozoid maturation. Peptides improperly processed by the enzyme may lead to infertility. The addition of NL-1 ex-vivo to seminal liquid or immature spermatozoids taken directly from testis during an in-vitro fertilization procedure will increase fertility. Conversely, the use of a small-molecule inhibitor or removal of NL-1 with an antibody could increase fertility during an in-vitro fertilization procedure. The administration of a NL-1 inhibitor may increase or decrease the fertility potential. This inhibitor is formulated and administered as described above.
  NL-3 is found in ovaries and may be involved in the processing of a peptide involved in the maturation of eggs. The addition of NL-3 ex-vivo to immature eggs taken directly from ovaries during an in-vitro fertilization procedure will increase fertility. Conversely, the use of a small-molecule inhibitor or removal of NL-3 with an antibody could increase fertility during an in-vitro fertilization procedure. This inhibitor is formulated and administered as described above;
  NL-3 is found in bones. The improper processing of peptides by the enzyme may result in bone disease or abnormal phosphate metabolism. Administration of an inhibitor, as described above, will allow the disease management.

TABLE I

Extend of amino acid sequence identity between members of the NEP-like family

|        | hNEP | hPEX | hECE-1A | hECE-2 | hKELL | sNL-1 | hNL-2 | hNL-3 |
|--------|------|------|---------|--------|-------|-------|-------|-------|
| hNEP   | 100* |      |         |        |       |       |       |       |
| hPEX   | 35   | 100  |         |        |       |       |       |       |
| hECE-1A| 39   | 38   | 100     |        |       |       |       |       |
| hECE-2 | 36   | 37   | 62      | 100    |       |       |       |       |
| hKELL  | 23   | 24   | 30      | 31     | 100   |       |       |       |
| sNL-1  | 55   | 39   | 39      | 39     | 26    | 100   |       |       |
| hNL-2  | 54   | 39   | 39      | 39     | 26    | 77    | 100   |       |
| hNL-3  | 35   | 32   | 37      | 37     | 28    | 36    | 34    | 100   |

*percentage of sequence identity

REFERENCE LIST

Almenoff, J., Teirstein, A. S., Thornton, J. C., and Orlowski, M. (1984) J. Lab. Clin. Med. 103, 420–431

Anderson, A. D., Thomas, L., Hayflick, J. S., and Thomas, G. (1993) J. Biol. Chem. 268, 24887–24891

Ausubel, F. M., Brent, R., Kingston, R. E., Moore, D. D., and Smith, J. A. (1988). Current protocols in molecular biology (New York: Wiley Interscience).

Aviv, R., Gurbanov, K., Hoffman, A., Blumberg, S., and Winaver, J. (1995) Kidney Int. 47, 855–860

Bateman, R. C., Jackson D., Slaughter, C. A., Unnithan, S., Chai, Y. G., Moomaw, C., sand Hersh, L. B. (1989) J. Biol. Chem. 264, 6151–6157

Bawab, W., Aloyz, R. S., Crine, P., Roques, B. P., Des-Groseillers, L. (1993) Biochem. J. 296, 459–465

Beaumont, A., Le Moual, H., Boileau, G., Crine, P., and Roques, B. P. (1991). Evidence that both arginine 102 and arginine 747 are involved in substrate binding to neutral endopeptidase (EC 3.4.24.11). J.Biol.Chem. 266, 214–220.

Benjannet, S., Savaria, D., Laslop, A., Munzer, J. S., Chretien, M., Marcinkiewicz, M., and Seidah, N. G. (1997) J. Biol. Chem. 272, 26210–26218.

Chen, C. and Okayama, H. (1987) Mol. Cell Biol. 7, 2745–2752

Chidiac, P., Nouet, S., and Bouvier, M. (1996) Mol. Pharmacol. 50, 662–669

Corvol, P. and Williams, T. A. (1997). Biochemical and molecular aspects of angiotensin I-converting enzyme. In Cell-surface peptidases in health and disease. A. J. Kenny and C. M. Boustead, eds. (Oxford, UK: BIOS Scientific Publishers Ltd), pp. 99–117.

Crine, P., Dion, N., and Boileau, G. (1997). Endopeptidase-24.11. In Cell-Surface Peptidases in Health and Disease. A. J. Kenny and C. M. Boustead, eds. (Oxford: BIOS Scientific Publishers), pp. 79–98.

Crine, P., LeGrimellec, C., Lemieux, E., Labonte, L., Fortin, S., Blachier, A. and Aubry, M. (1985) The production and characterization of a monoclonal antibody specific for the 94000 dalton enkephalin-degrading peptidase from rabbit kidney brush border. Biochem. Biophys Res. Commun. 131, 255–261.

Deschodt-Lanckman, M., Michaux, F., de Prez, E., Abramowicz, D., Vanherweghem, J. L., and Goldman, M. (1989) Life Sci. 45, 133–141

Devault, A., Nault, C., Zollinger, M., Fournie-Zaluski, M.-C., Roques, B. P., Crine, P., and Boileau, G. (1988a). Expression of neutral endopeptidase (enkephalinase) in heterologous COS-1 cells. Characterization of the recombinant enzyme and evidence for a glutamic acid residue at the active site. J.Biol.Chem. 263, 4033–4040.

Devault, A., Sales, V., Nault, C., Beaumont, A., Roques, B. P., Crine, P., and Boileau, G. (1988b). Exploration of the catalytic site of endopeptidase 24.11 by site-directed mutagenesis. Histidine residues 583 and 587 are essential for catalysis. FEBS Lett. 231, 54–58.

Dion, N., Le Moual, H., Crine, P., and Boileau, G. (1993). Kinetic evidence that His-711 of neutral endopeptidase 24.11 is involved in stabilization of the transition state. FEBS Lett. 318, 301–304.

Dion, N., Le Moual, H., Fournié-Zaluski, M. C., Roques, B. P., Crine, P., and Boileau, G. (1995). Evidence that Asn$^{542}$ of neprilysin (EC 3.4.24.11) is involved in binding of the $P_2'$ residue of substrates and inhibitors. Biochem. J. 311, 623–627.

Holmes, M. A. and Matthews, B. W. (1982). Structure of thermolysin refined at 1.6 A resolution. J.Mol.Biol. 160, 623–639.

Hooper, N. M. (1994). Families of zinc metalloproteases. FEBS Lett. 354, 1–6.

Howard, T. E., Shai, S. Y., Langford, K. G., Martin, B. M., Bernstein, K. E. (1990) Mol. Cell. Biol. 10, 4294–4302

Ikeda, K., Emoto, N., Raharjo, S. B., Nurhantari, Y., Saiki, K., Yokoyama, M., Matsuo, M. (1999) J. Biol. Chem. 274, 32469–32477

Jeannotte, L., Burbach, J. P., Drouin, J. (1987) Mol. Endocrinol. 1, 749–757

Johnson, A. R., Coalson, J. J., Ashton, J., Larumbide, M., and Erdos, E. G. (1985) Am. Rev. Respir. Dis. 132, 1262–1267

Johnson, G. D., Stevenson, T., and Ahn, K. (1999) J. Biol. Chem. 274, 4053–4058 Endocrinol. 3, 1191–1196

Kenny, J. (1993). Endopeptidase-24.11: Putative substrates and possible roles. Biochem.Soc.Trans. 21, 663–668.

Kew, D., Jin, D. F., Kim, F., Laddis, T., and Kilpatrick, D. L. (1989) Mol. J. Biol Chem. 266, 214–220

Kew, D., Muffly, K. E., and Kilpatrick, D. L. (1990) Proc. Natl. Acad. Sci. U.S.A 87, 9143–9147

Kilpatrick, D. L., Borland, K., and Jin, D. F. (1987) Proc. Natl. Acad. Sci. U.S.A. 84, 5695–5699

Kilpatrick, D. L. and Millette, C. F. (1986) Proc. Natl. Acad. Sci. U.S.A 83, 5015–5018

Kozak, M. (1986) Cell 44, 283–292

Lafrance, M. H., Vezina, C., Wang, Q., Boileau, G., Crine, P., and Lemay, G. (1994) Biochem. J. 302, 451–454.

Lanctot, C., Fournier, H., Howell, S., Boileau, G., and Crine, P. (1995) Biochem. J. 305, 165–171

Le Moual, H., Devault, A., Roques, B. P., Crine, P., and Boileau, G. (1991). Identification of glutamic acid 646 as a zinc-coordinating residue in endopeptidase-24.11. J.Biol.Chem. 266, 15670–15674.

Le Moual, H., Dion, N., Roques, B. P., Crine, P., and Boileau, G. (1994). Asp650 is crucial for catalytic activity of neutral endopeptidase 24-11. Eur.J.Biochem. 221, 475–480.

Lemay, G., Waksman, G., Roques, B. P., Crine, P., and Boileau, G. (1989). Fusion of a cleavable signal peptide to the ectodomain of neutral endopeptidase (EC 3.4.24.11) results in the secretion of an active enzyme in COS-1 cells. J.Biol.Chem. 264, 15620–15623.

Logeat, F., Bessia, C., Brou, C., LeBail, O., Jarriault, S., Seidah, N. G., and Israel, A. (1998) Proc. Natl. Acad. Sci. USA 95, 8108–8112.

Malfroy, B., and Schwartz, J. C. (1982) Biochem. Biophys. Res.Com. 106, 276–285

Marie-Claire, C., Ruffet, E., Antonczak, S., Beaumont, A., O'Donohue, M., Roques, B. P., and Fournie-Zaluski, M. C. (1997). Evidence by site-directed mutagenesis that arginine 203 of thermolysin and arginine 717 of neprilysin (neutral endopeptidase) play equivalent critical roles in substrate hydrolysis and inhibitor binding. Biochemistry 36, 13938–13945.

Mehta, N. D., Don, J., Zinn, S. A., Millette, C., Wolgemuth, D. J., and Kilpatrick, D. L. (1994) Endocrinology 135, 1543–1550

Milhiet, P. E., Chevallier, S., Corbeil, D., Seidah, N. G., Crine, P., and Boileau, G. (1995) Biochem. J. 309, 683–688

Monsees, T. K., Gornig, M., Schill, W. B., and Miska, W. (1998) Andrologia 30, 185–191

Nakayama, K. (1997) Biochem. J. 327, 625–635

Nakayama, K., Kim, W. S., Torii, S., Hosaka, M., Nakagawa, T., Ikemizu, J., Baba, T., and Murakami, K. (1992) J. Biol. Chem. 267, 5897–5900

Phelan, M. C., Rogers, R. C., Clarkson, K. B., Bowyer, F. P., Levine, M. A., Estabrooks, L. L., Severson, M. C., and Dobyns, W. B. (1995). Albright hereditary osteodystrophy and del(2) (q37.3) in four unrelated individuals. Am.J.Med.Genet. 58, 1–7.

Raut, R., Rouleau, J. L., Blais, C. Jr, Gosselin, H., Molinaro, G., Sirois, M. G., Lepage, Y., Crine, P., and Adam, A. (1999) Bradykinin metabolism in the postinfarcted rat heart: role of ACE and neutral endopeptidase 24.11. Am. J Physiol. 276, H1769–H1779.

Ruchon, A. F., Marcinkiewicz, M., Siegfried, G., Tenenhouse, H. S., DesGroseillers, L., Crine, P., and Boileau, G. (1998). Pex mRNA is localized in developing mouse osteoblasts and odontoblasts. J.Histochem.Cytochem. 46, 459–468.

Sambrook, J., Fritsch, E. F., and Maniatis, T. (1989). Molecular cloning, a laboratory manual (New-York: Cold Spring Harbor Laboratory Press).

Schacke, H., Schumann, H., Hammami-Hauasli, N., Raghunath, M., and Bruckner-Tuderman, L. (1998) J. Biol. Chem. 273, 25937–25943

Seidah, N. G. and Chretien, M. (1995). Pro-protein convertases of subtilisin/kexin family. Methods Enzymol. 244, 175–188.

Seidah, N. G., Day, R., Hamelin, J., Gaspar, A., Collard, M. W., and Chretien, M. (1992) Mol. Endocrinol. 6, 1559–1570

Seidah, N. G., Hamelin, J., Mamarbachi, M., Dong, W., Tadros, H., Mbikai, M., Chretien, M., and Day, R. (1996) Proc. Natl. Acad. Sci. USA 93, 3388–3393

Soleilhac, J. M., Lafuma, C., Porcher, J. M., Auburtin, G., and Roques, B. P. (1996) Eur. J. Clin. Invest. 26, 1011–1017

Torii, S., Yamagishi, T., Murakami, K., and Nakayama, K. (1993) FEBS Lett. 316, 12–16

Turner, A. J. (1997a). Endothelin-converting enzymes. In Cell-surface peptidases in health and disease. A. J. Kenny and C. M. Boustead, eds. (Oxford, UK: BIOS Scientific Publishers Ltd.), pp. 137–153.

Turner, A. J. and Tanzawa, K. (1997b). Mammalian membrane metallopeptidases: NEP, ECE, KELL, and PEX. FASEB J. 11, 355–364.

Turner, A. J., and Murphy, L. (1996) Biochem. Pharmacol. 51, 91–102

Turner, A. J., Matsas, R., and Kenny, A. J. (1985) Biochem. Pharmacol. 34, 1347–1356

Vijayaraghavan, J., Kim, Y.-A., Jackson, D., Orlowski, M., and Hersh, L. B. (1990). Use of site-directed mutagenesis to identify valine-573 in the S'1 binding site of rat neutral endopeptidase 24.11 (enkephalinase). Biochemistry 29, 8052–8056.

---

What is claimed is:

1. An isolated nucleic acid comprising a nucleotide sequence encoding a metallopeptidase having at least about 95% amino acid sequence identity with the complete amino acid sequence of SEQ ID NO: 13.

2. A recombinant vector comprising the isolated nucleotide sequence of claim 1.

3. An isolated host cell transformed with the vector of claim 2.

4. An isolated nucleic acid comprising the nucleotide sequence of SEQ ID NO: 12.

5. A recombinant vector comprising the isolated nucleotide sequence of claim 4.

6. An isolated host cell transformed with the vector of claim 5.

* * * * *

SEQUENCE LISTING

```
<160> NUMBER OF SEQ ID NOS: 17

<210> SEQ ID NO 1
<211> LENGTH: 750
<212> TYPE: PRT
<213> ORGANISM: Homo sapiens

<400> SEQUENCE: 1

Met Gly Lys Ser Glu Ser Gln Met Asp Ile Thr Asp Ile Asn Thr Pro
 1               5                  10                  15

Lys Pro Lys Lys Lys Gln Arg Trp Thr Pro Leu Glu Ile Ser Leu Ser
             20                  25                  30

Val Leu Val Leu Leu Leu Thr Ile Ile Ala Val Thr Met Ile Ala Leu
         35                  40                  45

Tyr Ala Thr Tyr Asp Asp Gly Ile Cys Lys Ser Ser Asp Cys Ile Lys
     50                  55                  60

Ser Ala Ala Arg Leu Ile Gln Asn Met Asp Ala Thr Thr Glu Pro Cys
 65                  70                  75                  80

Thr Asp Phe Phe Lys Tyr Ala Cys Gly Gly Trp Leu Lys Arg Asn Val
                 85                  90                  95

Ile Pro Glu Thr Ser Ser Arg Tyr Gly Asn Phe Asp Ile Leu Arg Asp
            100                 105                 110

Glu Leu Glu Val Val Leu Lys Asp Val Leu Gln Glu Pro Lys Thr Glu
        115                 120                 125

Asp Ile Val Ala Val Gln Lys Ala Lys Ala Leu Tyr Arg Ser Cys Ile
    130                 135                 140

Asn Glu Ser Ala Ile Asp Ser Arg Gly Gly Glu Pro Leu Leu Lys Leu
145                 150                 155                 160

Leu Pro Asp Ile Tyr Gly Trp Pro Val Ala Thr Glu Asn Trp Glu Gln
                165                 170                 175

Lys Tyr Gly Ala Ser Trp Thr Ala Glu Lys Ala Ile Ala Gln Leu Asn
            180                 185                 190
```

-continued

Ser Lys Tyr Gly Lys Lys Val Leu Ile Asn Leu Phe Val Gly Thr Asp
        195                 200                 205

Asp Lys Asn Ser Val Asn His Val Ile His Ile Asp Gln Pro Arg Leu
    210                 215                 220

Gly Leu Pro Ser Arg Asp Tyr Tyr Glu Cys Thr Gly Ile Tyr Lys Glu
225                 230                 235                 240

Ala Cys Thr Ala Tyr Val Asp Phe Met Ile Ser Val Ala Arg Leu Ile
                245                 250                 255

Arg Gln Glu Glu Arg Leu Pro Ile Asp Glu Asn Gln Leu Ala Leu Glu
            260                 265                 270

Met Asn Lys Val Met Glu Leu Glu Lys Glu Ile Ala Asn Ala Thr Ala
        275                 280                 285

Lys Pro Glu Asp Arg Asn Asp Pro Met Leu Leu Tyr Asn Lys Met Thr
    290                 295                 300

Leu Ala Gln Ile Gln Asn Asn Phe Ser Leu Glu Ile Asn Gly Lys Pro
305                 310                 315                 320

Phe Ser Trp Leu Asn Phe Thr Asn Glu Ile Met Ser Thr Val Asn Ile
                325                 330                 335

Ser Ile Thr Asn Glu Glu Asp Val Val Val Tyr Ala Pro Glu Tyr Leu
            340                 345                 350

Thr Lys Leu Lys Pro Ile Leu Thr Lys Tyr Ser Ala Arg Asp Leu Gln
        355                 360                 365

Asn Leu Met Ser Trp Arg Phe Ile Met Asp Leu Val Ser Ser Leu Ser
    370                 375                 380

Arg Thr Tyr Lys Glu Ser Arg Asn Ala Phe Arg Lys Ala Leu Tyr Gly
385                 390                 395                 400

Thr Thr Ser Glu Thr Ala Thr Trp Arg Arg Cys Ala Asn Tyr Val Asn
                405                 410                 415

Gly Asn Met Glu Asn Ala Val Gly Arg Leu Tyr Val Glu Ala Ala Phe
            420                 425                 430

Ala Gly Glu Ser Lys His Val Val Glu Asp Leu Ile Ala Gln Ile Arg
        435                 440                 445

Glu Val Phe Ile Gln Thr Leu Asp Asp Leu Thr Trp Met Asp Ala Glu
    450                 455                 460

Thr Lys Lys Arg Ala Glu Glu Lys Ala Leu Ala Ile Lys Glu Arg Ile
465                 470                 475                 480

Gly Tyr Pro Asp Asp Ile Val Ser Asn Asp Asn Lys Leu Asn Asn Glu
                485                 490                 495

Tyr Leu Glu Leu Asn Tyr Lys Glu Asp Glu Tyr Phe Glu Asn Ile Ile
            500                 505                 510

Gln Asn Leu Lys Phe Ser Gln Ser Lys Gln Leu Lys Lys Leu Arg Glu
        515                 520                 525

Lys Val Asp Lys Asp Glu Trp Ile Ser Gly Ala Ala Val Val Asn Ala
    530                 535                 540

Phe Tyr Ser Ser Gly Arg Asn Gln Ile Val Phe Pro Ala Gly Ile Leu
545                 550                 555                 560

Gln Pro Pro Phe Phe Ser Ala Gln Gln Ser Asn Ser Leu Asn Tyr Gly
                565                 570                 575

Gly Ile Gly Met Val Ile Gly His Glu Ile Thr His Gly Phe Asp Asp
            580                 585                 590

Asn Gly Arg Asn Phe Asn Lys Asp Gly Asp Leu Val Asp Trp Trp Thr
        595                 600                 605

```
Gln Gln Ser Ala Ser Asn Phe Lys Glu Gln Ser Gln Cys Met Val Tyr
        610                 615                 620

Gln Tyr Gly Asn Phe Ser Trp Asp Leu Ala Gly Gln His Leu Asn
625                 630                 635                 640

Gly Ile Asn Thr Leu Gly Glu Asn Ile Ala Asp Asn Gly Gly Leu Gly
                645                 650                 655

Gln Ala Tyr Arg Ala Tyr Gln Asn Tyr Ile Lys Lys Asn Gly Glu Glu
                660                 665                 670

Lys Leu Leu Pro Gly Leu Asp Leu Asn His Lys Gln Leu Phe Phe Leu
                675                 680                 685

Asn Phe Ala Gln Val Trp Cys Gly Thr Tyr Arg Pro Glu Tyr Ala Val
690                 695                 700

Asn Ser Ile Lys Thr Asp Val His Ser Pro Gly Asn Phe Arg Ile Ile
705                 710                 715                 720

Gly Thr Leu Gln Asn Ser Ala Glu Phe Ser Glu Ala Phe His Cys Arg
                725                 730                 735

Lys Asn Ser Tyr Met Asn Pro Glu Lys Lys Cys Arg Val Trp
                740                 745                 750

<210> SEQ ID NO 2
<211> LENGTH: 749
<212> TYPE: PRT
<213> ORGANISM: Homo sapiens

<400> SEQUENCE: 2

Met Glu Ala Glu Thr Gly Ser Ser Val Glu Thr Gly Lys Lys Ala Asn
1               5                   10                  15

Arg Gly Thr Arg Ile Ala Leu Val Val Phe Val Gly Gly Thr Leu Val
                20                  25                  30

Leu Gly Thr Ile Leu Phe Leu Val Ser Gln Gly Leu Leu Ser Leu Gln
                35                  40                  45

Ala Lys Gln Glu Tyr Cys Leu Lys Pro Glu Cys Ile Glu Ala Ala Ala
        50                  55                  60

Ala Ile Leu Ser Lys Val Asn Leu Ser Val Asp Pro Cys Asp Asn Phe
65                  70                  75                  80

Phe Arg Phe Ala Cys Asp Gly Trp Ile Ser Asn Asn Pro Ile Pro Glu
                85                  90                  95

Asp Met Pro Ser Tyr Gly Val Tyr Pro Trp Leu Arg His Asn Val Asp
                100                 105                 110

Leu Lys Leu Lys Glu Leu Leu Glu Lys Ser Ile Ser Arg Arg Arg Asp
        115                 120                 125

Thr Glu Ala Ile Gln Lys Ala Lys Ile Leu Tyr Ser Ser Cys Met Asn
130                 135                 140

Glu Lys Ala Ile Glu Lys Ala Asp Ala Lys Pro Leu Leu His Ile Leu
145                 150                 155                 160

Arg His Ser Pro Phe Arg Trp Pro Val Leu Glu Ser Asn Ile Gly Pro
                165                 170                 175

Glu Gly Val Trp Ser Glu Arg Lys Phe Ser Leu Leu Gln Thr Leu Ala
                180                 185                 190

Thr Phe Arg Gly Gln Tyr Ser Asn Ser Val Phe Ile Arg Leu Tyr Val
        195                 200                 205

Ser Pro Asp Asp Lys Ala Ser Asn Glu His Ile Leu Lys Leu Asp Gln
210                 215                 220

Ala Thr Leu Ser Leu Ala Val Arg Glu Asp Tyr Leu Asp Asn Ser Thr
225                 230                 235                 240
```

```
Glu Ala Lys Ser Tyr Arg Asp Ala Leu Tyr Lys Phe Met Val Asp Thr
                245                 250                 255

Ala Val Leu Leu Gly Ala Asn Ser Ser Arg Ala Glu His Asp Met Lys
            260                 265                 270

Ser Val Leu Arg Leu Glu Ile Lys Ile Ala Glu Ile Met Ile Pro His
        275                 280                 285

Glu Asn Arg Thr Ser Glu Ala Met Tyr Asn Lys Met Asn Ile Ser Glu
    290                 295                 300

Leu Ser Ala Met Ile Pro Gln Phe Asp Trp Leu Gly Tyr Ile Lys Lys
305                 310                 315                 320

Val Ile Asp Thr Arg Leu Tyr Pro His Leu Lys Asp Ile Ser Pro Ser
                325                 330                 335

Glu Asn Val Val Arg Val Pro Gln Tyr Phe Lys Asp Leu Phe Arg
            340                 345                 350

Ile Leu Gly Ser Glu Arg Lys Lys Thr Ile Ala Asn Tyr Leu Val Trp
        355                 360                 365

Arg Met Val Tyr Ser Arg Ile Pro Asn Leu Ser Arg Arg Phe Gln Tyr
    370                 375                 380

Arg Trp Leu Glu Phe Ser Arg Val Ile Gln Gly Thr Thr Thr Leu Leu
385                 390                 395                 400

Pro Gln Trp Asp Lys Cys Val Asn Phe Ile Glu Ser Ala Leu Pro Tyr
                405                 410                 415

Val Val Gly Lys Met Phe Val Asp Val Tyr Phe Gln Glu Asp Lys Lys
            420                 425                 430

Glu Met Met Glu Glu Leu Val Glu Gly Val Arg Trp Ala Phe Ile Asp
        435                 440                 445

Met Leu Glu Lys Glu Asn Glu Trp Met Asp Ala Gly Thr Lys Arg Lys
    450                 455                 460

Ala Lys Glu Lys Ala Arg Ala Val Leu Ala Lys Val Gly Tyr Pro Glu
465                 470                 475                 480

Phe Ile Met Asn Asp Thr His Val Asn Glu Asp Leu Lys Ala Ile Lys
                485                 490                 495

Phe Ser Glu Ala Asp Tyr Phe Gly Asn Val Leu Gln Thr Arg Lys Tyr
            500                 505                 510

Leu Ala Gln Ser Asp Phe Phe Trp Leu Arg Lys Ala Val Pro Lys Thr
        515                 520                 525

Glu Trp Phe Thr Asn Pro Thr Thr Val Asn Ala Phe Tyr Ser Ala Ser
    530                 535                 540

Thr Asn Gln Ile Arg Phe Pro Ala Gly Glu Leu Gln Lys Pro Phe Phe
545                 550                 555                 560

Trp Gly Thr Glu Tyr Pro Arg Ser Leu Ser Tyr Gly Ala Ile Gly Val
                565                 570                 575

Ile Val Gly His Glu Phe Thr His Gly Phe Asp Asn Asn Gly Arg Lys
            580                 585                 590

Tyr Asp Lys Asn Gly Asn Leu Asp Pro Trp Trp Ser Thr Glu Ser Glu
        595                 600                 605

Glu Lys Phe Lys Glu Lys Thr Lys Cys Met Ile Asn Gln Tyr Ser Asn
    610                 615                 620

Tyr Tyr Trp Lys Lys Ala Gly Leu Asn Val Lys Gly Lys Arg Thr Leu
625                 630                 635                 640

Gly Glu Asn Ile Ala Asp Asn Gly Gly Leu Arg Glu Ala Phe Arg Ala
                645                 650                 655
```

-continued

```
Tyr Arg Lys Trp Ile Asn Asp Arg Arg Gln Gly Leu Glu Glu Pro Leu
                660                 665                 670

Leu Pro Gly Ile Thr Phe Thr Asn Asn Gln Leu Phe Phe Leu Ser Tyr
            675                 680                 685

Ala His Val Arg Cys Asn Ser Tyr Arg Pro Glu Ala Ala Arg Glu Gln
        690                 695                 700

Val Gln Ile Gly Ala His Ser Pro Pro Gln Phe Arg Val Asn Gly Ala
705                 710                 715                 720

Ile Ser Asn Phe Glu Glu Phe Gln Lys Ala Phe Asn Cys Pro Pro Asn
                725                 730                 735

Ser Thr Met Asn Arg Gly Met Asp Ser Cys Arg Leu Trp
            740                 745
```

<210> SEQ ID NO 3
<211> LENGTH: 732
<212> TYPE: PRT
<213> ORGANISM: Homo sapiens

<400> SEQUENCE: 3

```
Met Glu Gly Gly Asp Gln Ser Glu Glu Pro Arg Glu Arg Ser Gln
  1               5                  10                  15

Ala Gly Gly Met Gly Thr Leu Trp Ser Gln Glu Ser Thr Pro Glu Glu
                20                  25                  30

Arg Leu Pro Val Glu Gly Ser Arg Pro Trp Ala Val Ala Arg Arg Val
            35                  40                  45

Leu Thr Ala Ile Leu Ile Leu Gly Leu Leu Cys Phe Ser Val Leu
         50                  55                  60

Leu Phe Tyr Asn Phe Gln Asn Cys Gly Pro Arg Pro Cys Glu Thr Ser
 65                  70                  75                  80

Val Cys Leu Asp Leu Arg Asp His Tyr Leu Ala Ser Gly Asn Thr Ser
                 85                  90                  95

Val Ala Pro Cys Thr Asp Phe Phe Ser Phe Ala Cys Gly Arg Ala Lys
            100                 105                 110

Glu Thr Asn Asn Ser Phe Gln Glu Leu Ala Thr Lys Asn Lys Asn Arg
        115                 120                 125

Leu Arg Arg Ile Leu Glu Val Gln Asn Ser Trp His Pro Gly Ser Gly
130                 135                 140

Glu Glu Lys Ala Phe Gln Phe Tyr Asn Ser Cys Met Asp Thr Leu Ala
145                 150                 155                 160

Ile Glu Ala Ala Gly Thr Gly Pro Leu Arg Gln Val Ile Glu Glu Leu
                165                 170                 175

Gly Gly Trp Arg Ile Ser Gly Lys Trp Thr Ser Leu Asn Phe Asn Arg
            180                 185                 190

Thr Leu Arg Leu Leu Met Ser Gln Tyr Gly His Phe Pro Phe Phe Arg
        195                 200                 205

Ala Tyr Leu Gly Pro His Pro Ala Ser Pro His Thr Pro Val Ile Gln
    210                 215                 220

Ile Asp Gln Pro Glu Phe Asp Val Pro Leu Lys Gln Asp Gln Glu Gln
225                 230                 235                 240

Lys Ile Tyr Ala Gln Ile Phe Arg Glu Tyr Leu Thr Tyr Leu Asn Gln
                245                 250                 255

Leu Gly Thr Leu Leu Gly Gly Asp Pro Ser Lys Val Gln Glu His Ser
            260                 265                 270

Ser Leu Ser Ile Ser Ile Thr Ser Arg Leu Phe Gln Phe Leu Arg Pro
        275                 280                 285
```

```
Leu Glu Gln Arg Arg Ala Gln Gly Lys Leu Phe Gln Met Val Thr Ile
    290                 295                 300
Asp Gln Leu Lys Glu Met Ala Pro Ala Ile Asp Trp Leu Ser Cys Leu
305                 310                 315                 320
Gln Ala Thr Phe Thr Pro Met Ser Leu Ser Pro Ser Gln Ser Leu Val
                325                 330                 335
Val His Asp Val Glu Tyr Leu Lys Asn Met Ser Gln Leu Val Glu Glu
                340                 345                 350
Met Leu Leu Lys Gln Arg Asp Phe Leu Gln Ser His Met Ile Leu Gly
            355                 360                 365
Leu Val Val Thr Leu Ser Pro Ala Leu Asp Ser Gln Phe Gln Glu Ala
370                 375                 380
Arg Arg Lys Leu Ser Gln Lys Leu Arg Glu Leu Thr Glu Gln Pro Pro
385                 390                 395                 400
Met Pro Ala Arg Pro Arg Trp Met Lys Cys Val Glu Glu Thr Gly Thr
                405                 410                 415
Phe Phe Glu Pro Thr Leu Ala Ala Leu Phe Val Arg Glu Ala Phe Gly
                420                 425                 430
Pro Ser Thr Arg Ser Ala Ala Met Lys Leu Phe Thr Ala Ile Arg Asp
            435                 440                 445
Ala Leu Ile Thr Arg Leu Arg Asn Leu Pro Trp Met Asn Glu Glu Thr
450                 455                 460
Gln Asn Met Ala Gln Asp Lys Val Ala Gln Leu Gln Val Glu Met Gly
465                 470                 475                 480
Ala Ser Glu Trp Ala Leu Lys Pro Glu Leu Ala Arg Gln Glu Tyr Asn
                485                 490                 495
Asp Ile Gln Leu Gly Ser Ser Phe Leu Gln Ser Val Leu Ser Cys Val
                500                 505                 510
Arg Ser Leu Arg Ala Arg Ile Val Gln Ser Phe Leu Gln Pro His Pro
            515                 520                 525
Gln His Arg Trp Lys Val Ser Pro Trp Asp Val Asn Ala Tyr Tyr Ser
530                 535                 540
Val Ser Asp His Val Val Phe Pro Ala Gly Leu Leu Gln Pro Pro
545                 550                 555                 560
Phe Phe His Pro Gly Tyr Pro Arg Ala Val Asn Phe Gly Ala Ala Gly
                565                 570                 575
Ser Ile Met Ala His Glu Leu Leu His Ile Phe Tyr Gln Leu Leu Leu
                580                 585                 590
Pro Gly Gly Cys Leu Ala Cys Asp Asn His Ala Leu Gln Glu Ala His
            595                 600                 605
Leu Cys Leu Lys Arg His Tyr Ala Ala Phe Pro Leu Pro Ser Arg Thr
610                 615                 620
Ser Phe Asn Asp Ser Leu Thr Phe Leu Glu Asn Ala Ala Asp Val Gly
625                 630                 635                 640
Gly Leu Ala Ile Ala Leu Gln Ala Tyr Ser Lys Arg Leu Leu Arg His
                645                 650                 655
His Gly Glu Thr Val Leu Pro Ser Leu Asp Leu Ser Pro Gln Gln Ile
                660                 665                 670
Phe Phe Arg Ser Tyr Ala Gln Val Met Cys Arg Lys Pro Ser Pro Gln
            675                 680                 685
Asp Ser His Asp Thr His Ser Pro Pro His Leu Arg Val His Gly Pro
690                 695                 700
```

Leu Ser Ser Thr Pro Ala Phe Ala Arg Tyr Phe Arg Cys Ala Arg Gly
705                 710                 715                 720

Ala Leu Leu Asn Pro Ser Ser Arg Cys Gln Leu Trp
                725                 730

<210> SEQ ID NO 4
<211> LENGTH: 753
<212> TYPE: PRT
<213> ORGANISM: Homo sapiens

<400> SEQUENCE: 4

Met Ser Thr Tyr Lys Arg Ala Thr Leu Asp Glu Glu Asp Leu Val Asp
1               5                   10                  15

Ser Leu Ser Glu Gly Asp Ala Tyr Pro Asn Gly Leu Gln Val Asn Phe
            20                  25                  30

His Ser Pro Arg Ser Gly Gln Arg Cys Trp Ala Ala Arg Thr Gln Val
        35                  40                  45

Glu Lys Arg Leu Val Val Leu Val Leu Leu Ala Ala Gly Leu Val
    50                  55                  60

Ala Cys Leu Ala Ala Leu Gly Ile Gln Tyr Gln Thr Arg Ser Pro Ser
65                  70                  75                  80

Val Cys Leu Ser Glu Ala Cys Val Ser Val Thr Ser Ser Ile Leu Ser
                85                  90                  95

Ser Met Asp Pro Thr Val Asp Pro Cys His Asp Phe Phe Ser Tyr Ala
            100                 105                 110

Cys Gly Gly Trp Ile Lys Ala Asn Pro Val Pro Asp Gly His Ser Arg
        115                 120                 125

Trp Gly Thr Phe Ser Asn Leu Trp Glu His Asn Gln Ala Ile Ile Lys
    130                 135                 140

His Leu Leu Glu Asn Ser Thr Ala Ser Val Ser Glu Ala Glu Arg Lys
145                 150                 155                 160

Ala Gln Val Tyr Tyr Arg Ala Cys Met Asn Glu Thr Arg Ile Glu Glu
                165                 170                 175

Leu Arg Ala Lys Pro Leu Met Glu Leu Ile Glu Arg Leu Gly Gly Trp
            180                 185                 190

Asn Ile Thr Gly Pro Trp Ala Lys Asp Asn Phe Gln Asp Thr Leu Gln
        195                 200                 205

Val Val Thr Ala His Tyr Arg Thr Ser Pro Phe Phe Ser Val Tyr Val
    210                 215                 220

Ser Ala Asp Ser Lys Asn Ser Asn Ser Asn Val Ile Gln Val Asp Gln
225                 230                 235                 240

Ser Gly Leu Gly Leu Pro Ser Arg Asp Tyr Tyr Leu Asn Lys Thr Glu
                245                 250                 255

Asn Glu Lys Val Leu Thr Gly Tyr Leu Asn Tyr Met Val Gln Leu Gly
            260                 265                 270

Lys Leu Leu Gly Gly Gly Asp Glu Glu Ala Ile Arg Pro Gln Met Gln
        275                 280                 285

Gln Ile Leu Asp Phe Glu Thr Ala Leu Ala Asn Ile Thr Ile Pro Gln
    290                 295                 300

Glu Lys Arg Arg Asp Glu Glu Leu Ile Tyr His Lys Val Thr Ala Ala
305                 310                 315                 320

Glu Leu Gln Thr Leu Ala Pro Ala Ile Asn Trp Leu Pro Phe Leu Asn
                325                 330                 335

Thr Ile Phe Tyr Pro Val Glu Ile Asn Glu Ser Glu Pro Ile Val Val
            340                 345                 350

```
Tyr Asp Lys Glu Tyr Leu Glu Gln Ile Ser Thr Leu Ile Asn Thr Thr
        355                 360                 365

Asp Arg Cys Leu Leu Asn Asn Tyr Met Ile Trp Asn Leu Val Arg Lys
        370                 375                 380

Thr Ser Ser Phe Leu Asp Gln Arg Phe Gln Asp Ala Asp Glu Lys Phe
385                 390                 395                 400

Met Glu Val Met Tyr Gly Thr Lys Lys Thr Cys Leu Pro Arg Trp Lys
                405                 410                 415

Phe Cys Val Ser Asp Thr Glu Asn Asn Leu Gly Phe Ala Leu Gly Pro
            420                 425                 430

Met Phe Val Lys Ala Thr Phe Ala Glu Asp Ser Lys Ser Ile Ala Thr
            435                 440                 445

Glu Ile Ile Leu Glu Ile Lys Lys Ala Phe Glu Glu Ser Leu Ser Thr
        450                 455                 460

Leu Lys Trp Met Asp Glu Glu Thr Arg Lys Ser Ala Lys Glu Lys Ala
465                 470                 475                 480

Asp Ala Ile Tyr Asn Met Ile Gly Tyr Pro Asn Phe Ile Met Asp Pro
                485                 490                 495

Lys Glu Leu Asp Lys Val Phe Asn Asp Tyr Thr Ala Val Pro Asp Leu
            500                 505                 510

Tyr Phe Glu Asn Ala Met Arg Phe Phe Asn Phe Ser Trp Arg Val Thr
        515                 520                 525

Ala Asp Gln Leu Arg Lys Ala Pro Asn Arg Asp Gln Trp Ser Met Thr
        530                 535                 540

Pro Pro Met Val Asn Ala Tyr Tyr Ser Pro Thr Lys Asn Glu Ile Val
545                 550                 555                 560

Phe Pro Ala Gly Ile Leu Gln Ala Pro Phe Tyr Thr Arg Ser Ser Pro
                565                 570                 575

Lys Ala Leu Asn Phe Gly Gly Ile Gly Val Val Gly His Glu Leu
            580                 585                 590

Thr His Ala Phe Asp Asp Gln Gly Arg Glu Tyr Asp Lys Asp Gly Asn
        595                 600                 605

Leu Arg Pro Trp Trp Lys Asn Ser Ser Val Glu Ala Phe Lys Arg Gln
        610                 615                 620

Thr Glu Cys Met Val Glu Gln Tyr Ser Asn Tyr Ser Val Asn Gly Glu
625                 630                 635                 640

Pro Val Asn Gly Arg His Thr Leu Gly Glu Asn Ile Ala Asp Asn Gly
                645                 650                 655

Gly Leu Lys Ala Ala Tyr Arg Ala Tyr Gln Asn Trp Val Lys Lys Asn
            660                 665                 670

Gly Ala Glu His Ser Leu Pro Thr Leu Gly Leu Thr Asn Asn Gln Leu
        675                 680                 685

Phe Phe Leu Gly Phe Ala Gln Val Trp Cys Ser Val Arg Thr Pro Glu
        690                 695                 700

Ser Ser His Glu Gly Leu Ile Thr Asp Pro His Ser Pro Ser Arg Phe
705                 710                 715                 720

Arg Val Ile Gly Ser Leu Ser Asn Ser Lys Glu Phe Ser Glu His Phe
                725                 730                 735

Arg Cys Pro Pro Gly Ser Pro Met Asn Pro His Lys Cys Glu Val
            740                 745                 750

Trp
```

```
<210> SEQ ID NO 5
<211> LENGTH: 24
<212> TYPE: DNA
<213> ORGANISM: Artificial Sequence
<220> FEATURE:
<221> NAME/KEY: modified_base
<222> LOCATION: (14)
<223> OTHER INFORMATION: i
<220> FEATURE:
<221> NAME/KEY: modified_base
<222> LOCATION: (18)
<223> OTHER INFORMATION: i
<220> FEATURE:
<221> NAME/KEY: modified_base
<222> LOCATION: (21)
<223> OTHER INFORMATION: i
<220> FEATURE:
<223> OTHER INFORMATION: Description of Artificial Sequence:
      Oligonucleotide primers for RT-PCR reactions

<400> SEQUENCE: 5
tggatggatc gacngganac naca                                          24

<210> SEQ ID NO 6
<211> LENGTH: 24
<212> TYPE: DNA
<213> ORGANISM: Artificial Sequence
<220> FEATURE:
<221> NAME/KEY: modified_base
<222> LOCATION: (14)
<223> OTHER INFORMATION: i
<220> FEATURE:
<221> NAME/KEY: modified_base
<222> LOCATION: (18)
<223> OTHER INFORMATION: i
<220> FEATURE:
<221> NAME/KEY: modified_base
<222> LOCATION: (21)
<223> OTHER INFORMATION: i
<220> FEATURE:
<223> OTHER INFORMATION: Description of Artificial Sequence:
      Oligonucleotide primers for RT-PCR reactions

<400> SEQUENCE: 6
tggatggatc gacngganac nacg                                          24

<210> SEQ ID NO 7
<211> LENGTH: 32
<212> TYPE: DNA
<213> ORGANISM: Artificial Sequence
<220> FEATURE:
<221> NAME/KEY: modified_base
<222> LOCATION: (4)
<223> OTHER INFORMATION: i
<220> FEATURE:
<221> NAME/KEY: modified_base
<222> LOCATION: (7)
<223> OTHER INFORMATION: i
<220> FEATURE:
<221> NAME/KEY: modified_base
<222> LOCATION: (14)
<223> OTHER INFORMATION: i
<220> FEATURE:
<221> NAME/KEY: modified_base
<222> LOCATION: (17)
<223> OTHER INFORMATION: i
<220> FEATURE:
<221> NAME/KEY: modified_base
<222> LOCATION: (20)
<223> OTHER INFORMATION: i
<220> FEATURE:
<221> NAME/KEY: modified_base
<222> LOCATION: (25)
<223> OTHER INFORMATION: i
<220> FEATURE:
```

-continued

```
<223> OTHER INFORMATION: Description of Artificial Sequence:
      Oligonucleotide primers for RT-PCR reactions

<400> SEQUENCE: 7
agtngtnttt cccngcnggn agtancttat ca                              32

<210> SEQ ID NO 8
<211> LENGTH: 32
<212> TYPE: DNA
<213> ORGANISM: Artificial Sequence
<220> FEATURE:
<221> NAME/KEY: modified_base
<222> LOCATION: (4)
<223> OTHER INFORMATION: i
<220> FEATURE:
<221> NAME/KEY: modified_base
<222> LOCATION: (7)
<223> OTHER INFORMATION: i
<220> FEATURE:
<221> NAME/KEY: modified_base
<222> LOCATION: (14)
<223> OTHER INFORMATION: i
<220> FEATURE:
<221> NAME/KEY: modified_base
<222> LOCATION: (17)
<223> OTHER INFORMATION: i
<220> FEATURE:
<221> NAME/KEY: modified_base
<222> LOCATION: (20)
<223> OTHER INFORMATION: i
<220> FEATURE:
<221> NAME/KEY: modified_base
<222> LOCATION: (25)
<223> OTHER INFORMATION: i
<220> FEATURE:
<223> OTHER INFORMATION: Description of Artificial Sequence:
      Oligonucleotide primers for RT-PCR reactions

<400> SEQUENCE: 8
agtngtnttt cccngcnggn agtancttgc ca                              32

<210> SEQ ID NO 9
<211> LENGTH: 33
<212> TYPE: DNA
<213> ORGANISM: Artificial Sequence
<220> FEATURE:
<221> NAME/KEY: modified_base
<222> LOCATION: (2)
<223> OTHER INFORMATION: i
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (18)
<223> OTHER INFORMATION: i
<220> FEATURE:
<221> NAME/KEY: modified_base
<222> LOCATION: (21)
<223> OTHER INFORMATION: i
<220> FEATURE:
<223> OTHER INFORMATION: Description of Artificial Sequence:
      Oligonucleotide primers for RT-PCR reactions
<220> FEATURE:
<221> NAME/KEY: modified_base
<222> LOCATION: (3)
<223> OTHER INFORMATION: i

<400> SEQUENCE: 9
```
anncncccna tctagtcngc ngactagttt ctc                                    33

<210> SEQ ID NO 10
<211> LENGTH: 35
<212> TYPE: DNA
<213> ORGANISM: Artificial Sequence
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (24)
<223> OTHER INFORMATION: i
<220> FEATURE:
<223> OTHER INFORMATION: Description of Artificial Sequence:
      Oligonucleotide primers for RT-PCR reactions

<400> SEQUENCE: 10
gatcaatctc tngatcgaag tctnaatctg gatgg                                  35

<210> SEQ ID NO 11
<211> LENGTH: 37
<212> TYPE: DNA
<213> ORGANISM: Artificial Sequence
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (31)
<223> OTHER INFORMATION: i
<220> FEATURE:
<223> OTHER INFORMATION: Description of Artificial Sequence:
      Oligonucleotide primers for RT-PCR reactions

<400> SEQUENCE: 11
tctcaccana tnctgagcat cgttcttcat ngggatg                                37

<210> SEQ ID NO 12
<211> LENGTH: 2925
<212> TYPE: DNA
<213> ORGANISM: Mus musculus
<220> FEATURE:
<221> NAME/KEY: CDS
<222> LOCATION: (332)..(2626)

<400> SEQUENCE: 12
cgggagccag caccgtgtga cctcacaccc agctcagctg ctctactcca cccggagccc        60
accttggcca gctcacccca actctgagac atcccaacct agcctttaag gacttgccta      120
gcagtgactg agagcaccag ggtcccctgg gcacttgggg cacagcttac agcattgaga      180
gcagagacca ggacagtgca ccagcttcag tgtgtcctag gcatccgatc cgggctccag      240
ctgcctctct cctagccctg gcctgggggg cttagcggtg tgccttccac ccagaaccgg      300 ctgatagggga aagtctgaga gcccagtggg g atg gtg gag aga gca ggc tgg        352
                                   Met Val Glu Arg Ala Gly Trp
                                     1               5 tgt cgg aag aag tcc cca ggc ttc gtg gag tat ggg ctg atg gtg ctg        400
Cys Arg Lys Lys Ser Pro Gly Phe Val Glu Tyr Gly Leu Met Val Leu
         10                  15                  20 ctg ctg ctg ttg ctg gga gcc ata gtg act ctg ggt gtc ttc tac agc        448
Leu Leu Leu Leu Leu Gly Ala Ile Val Thr Leu Gly Val Phe Tyr Ser -continued

|  |  |  |  |  |  |  |  |  |  |  |  |  |  |  |  |
|---|---|---|---|---|---|---|---|---|---|---|---|---|---|---|---|
|  |  | 25 |  |  |  |  | 30 |  |  |  |  | 35 |  |  |  |

| ata | ggg | aag | cag | ctg | ccc | ctc | tta | act | agc | ctg | cta | cac | ttc | tcc | tgg | 496 |
|---|---|---|---|---|---|---|---|---|---|---|---|---|---|---|---|---|
| Ile | Gly | Lys | Gln | Leu | Pro | Leu | Leu | Thr | Ser | Leu | Leu | His | Phe | Ser | Trp |  |
| 40 |  |  |  |  | 45 |  |  |  |  | 50 |  |  |  |  | 55 |  |

| gat | gag | agg | acg | gtt | gta | aaa | cga | gcc | ctc | agg | gat | tca | tca | ctg | aaa | 544 |
|---|---|---|---|---|---|---|---|---|---|---|---|---|---|---|---|---|
| Asp | Glu | Arg | Thr | Val | Val | Lys | Arg | Ala | Leu | Arg | Asp | Ser | Ser | Leu | Lys |  |
|  |  |  |  |  | 60 |  |  |  |  | 65 |  |  |  |  | 70 |  |

| agt | gac | atc | tgc | acc | acc | cca | agc | tgt | gtg | ata | gca | gct | gcc | aga | atc | 592 |
|---|---|---|---|---|---|---|---|---|---|---|---|---|---|---|---|---|
| Ser | Asp | Ile | Cys | Thr | Thr | Pro | Ser | Cys | Val | Ile | Ala | Ala | Ala | Arg | Ile |  |
|  |  |  |  | 75 |  |  |  |  | 80 |  |  |  |  | 85 |  |  |

| ctc | gaa | aac | atg | gac | caa | tcg | agg | aac | ccc | tgt | gaa | aac | ttc | tac | cag | 640 |
|---|---|---|---|---|---|---|---|---|---|---|---|---|---|---|---|---|
| Leu | Glu | Asn | Met | Asp | Gln | Ser | Arg | Asn | Pro | Cys | Glu | Asn | Phe | Tyr | Gln |  |
|  |  |  | 90 |  |  |  |  | 95 |  |  |  |  | 100 |  |  |  |

| tac | gcc | tgc | gga | ggc | tgg | ctg | agg | cac | cac | gtg | atc | cca | gag | acc | aac | 688 |
|---|---|---|---|---|---|---|---|---|---|---|---|---|---|---|---|---|
| Tyr | Ala | Cys | Gly | Gly | Trp | Leu | Arg | His | His | Val | Ile | Pro | Glu | Thr | Asn |  |
|  |  | 105 |  |  |  |  | 110 |  |  |  |  | 115 |  |  |  |  |

| tcc | cga | tac | agc | gtc | ttt | gac | atc | ctg | cgg | gac | gag | ctg | gag | gtt | atc | 736 |
|---|---|---|---|---|---|---|---|---|---|---|---|---|---|---|---|---|
| Ser | Arg | Tyr | Ser | Val | Phe | Asp | Ile | Leu | Arg | Asp | Glu | Leu | Glu | Val | Ile |  |
| 120 |  |  |  |  | 125 |  |  |  |  | 130 |  |  |  |  | 135 |  |

| ctc | aaa | ggg | gtg | ctg | gag | gat | tcc | act | tcc | cag | cat | cgc | ccg | gcc | gtg | 784 |
|---|---|---|---|---|---|---|---|---|---|---|---|---|---|---|---|---|
| Leu | Lys | Gly | Val | Leu | Glu | Asp | Ser | Thr | Ser | Gln | His | Arg | Pro | Ala | Val |  |
|  |  |  |  | 140 |  |  |  |  | 145 |  |  |  |  | 150 |  |  |

| gag | aag | gcc | aag | aca | cta | tat | cgc | tcc | tgc | atg | aac | caa | agt | gtg | atc | 832 |
|---|---|---|---|---|---|---|---|---|---|---|---|---|---|---|---|---|
| Glu | Lys | Ala | Lys | Thr | Leu | Tyr | Arg | Ser | Cys | Met | Asn | Gln | Ser | Val | Ile |  |
|  |  |  | 155 |  |  |  |  | 160 |  |  |  |  | 165 |  |  |  |

| gag | aag | aga | gac | tct | gag | ccc | ctg | ctg | agc | gtc | tta | aaa | atg | gta | gga | 880 |
|---|---|---|---|---|---|---|---|---|---|---|---|---|---|---|---|---|
| Glu | Lys | Arg | Asp | Ser | Glu | Pro | Leu | Leu | Ser | Val | Leu | Lys | Met | Val | Gly |  |
|  |  | 170 |  |  |  |  | 175 |  |  |  |  | 180 |  |  |  |  |

| ggt | tgg | cct | gtg | gcc | atg | gat | aag | tgg | aac | gag | acc | atg | ggc | ctc | aag | 928 |
|---|---|---|---|---|---|---|---|---|---|---|---|---|---|---|---|---|
| Gly | Trp | Pro | Val | Ala | Met | Asp | Lys | Trp | Asn | Glu | Thr | Met | Gly | Leu | Lys |  |
| 185 |  |  |  |  | 190 |  |  |  |  | 195 |  |  |  |  |  |  |

| tgg | gaa | ctg | gag | cga | cag | ttg | gct | gtg | ttg | aac | tcg | cag | ttc | aac | agg | 976 |
|---|---|---|---|---|---|---|---|---|---|---|---|---|---|---|---|---|
| Trp | Glu | Leu | Glu | Arg | Gln | Leu | Ala | Val | Leu | Asn | Ser | Gln | Phe | Asn | Arg |  |
| 200 |  |  |  |  | 205 |  |  |  |  | 210 |  |  |  |  | 215 |  |

| cgg | gtc | ctc | atc | gac | ctc | ttc | atc | tgg | aat | gac | gac | cag | aac | tcc | agc | 1024 |
|---|---|---|---|---|---|---|---|---|---|---|---|---|---|---|---|---|
| Arg | Val | Leu | Ile | Asp | Leu | Phe | Ile | Trp | Asn | Asp | Asp | Gln | Asn | Ser | Ser |  |
|  |  |  |  | 220 |  |  |  |  | 225 |  |  |  |  | 230 |  |  |

| cgg | cat | gtc | atc | tac | ata | gac | cag | ccc | acc | ttg | ggc | atg | cca | tcc | cgg | 1072 |
|---|---|---|---|---|---|---|---|---|---|---|---|---|---|---|---|---|
| Arg | His | Val | Ile | Tyr | Ile | Asp | Gln | Pro | Thr | Leu | Gly | Met | Pro | Ser | Arg |  |
|  |  |  | 235 |  |  |  |  | 240 |  |  |  |  | 245 |  |  |  |

| gag | tac | tat | ttc | cag | gag | gac | aac | aac | cac | aag | gta | cgg | aaa | gcc | tac | 1120 |
|---|---|---|---|---|---|---|---|---|---|---|---|---|---|---|---|---|
| Glu | Tyr | Tyr | Phe | Gln | Glu | Asp | Asn | Asn | His | Lys | Val | Arg | Lys | Ala | Tyr |  |
|  |  | 250 |  |  |  |  | 255 |  |  |  |  | 260 |  |  |  |  |

| ctg | gag | ttc | atg | acg | tca | gtg | gcc | act | atg | ctt | agg | aaa | gac | cag | aac | 1168 |
|---|---|---|---|---|---|---|---|---|---|---|---|---|---|---|---|---|
| Leu | Glu | Phe | Met | Thr | Ser | Val | Ala | Thr | Met | Leu | Arg | Lys | Asp | Gln | Asn |  |
|  | 265 |  |  |  |  | 270 |  |  |  |  | 275 |  |  |  |  |  |

| ctg | tcc | aag | gag | agc | gcc | atg | gtg | cgg | gag | gag | atg | gcg | gag | gtg | ctg | 1216 |
|---|---|---|---|---|---|---|---|---|---|---|---|---|---|---|---|---|
| Leu | Ser | Lys | Glu | Ser | Ala | Met | Val | Arg | Glu | Glu | Met | Ala | Glu | Val | Leu |  |
| 280 |  |  |  |  | 285 |  |  |  |  | 290 |  |  |  |  | 295 |  |

| gaa | ctg | gag | acg | cat | ctg | gcc | aac | gcc | aca | gtc | ccc | cag | gag | aaa | agg | 1264 |
|---|---|---|---|---|---|---|---|---|---|---|---|---|---|---|---|---|
| Glu | Leu | Glu | Thr | His | Leu | Ala | Asn | Ala | Thr | Val | Pro | Gln | Glu | Lys | Arg |  |
|  |  |  |  | 300 |  |  |  |  | 305 |  |  |  |  | 310 |  |  |

| cat | gat | gtc | act | gcc | ctg | tac | cac | cga | atg | gac | ctg | atg | gag | cta | cag | 1312 |
|---|---|---|---|---|---|---|---|---|---|---|---|---|---|---|---|---|
| His | Asp | Val | Thr | Ala | Leu | Tyr | His | Arg | Met | Asp | Leu | Met | Glu | Leu | Gln |  |
|  |  |  | 315 |  |  |  |  | 320 |  |  |  |  | 325 |  |  |  |

| gaa | agg | ttt | ggt | ctg | aag | ggg | ttt | aac | tgg | act | ctc | ttc | ata | caa | aac | 1360 |
|---|---|---|---|---|---|---|---|---|---|---|---|---|---|---|---|---|
| Glu | Arg | Phe | Gly | Leu | Lys | Gly | Phe | Asn | Trp | Thr | Leu | Phe | Ile | Gln | Asn |  |
|  |  | 330 |  |  |  |  | 335 |  |  |  |  | 340 |  |  |  |  |

| gtg | ttg | tct | tct | gtg | gaa | gtc | gag | ctg | ttc | cca | gat | gag | gag | gtg | gtg | 1408 |

|     |     |     |     |     |     |     |     |     |     |     |     |      |
| --- | --- | --- | --- | --- | --- | --- | --- | --- | --- | --- | --- | ---- |
| Val | Leu | Ser | Ser | Val | Glu | Val | Glu | Leu | Phe | Pro | Asp | Glu Val Val |
|     |     | 345 |     |     |     | 350 |     |     |     | 355 |     |      |

```
gtc tac ggc atc ccc tac ctg gag aat ctg gag gat atc att gat agc      1456
Val Tyr Gly Ile Pro Tyr Leu Glu Asn Leu Glu Asp Ile Ile Asp Ser
360             365             370             375 tac tca gca cgg acc atg cag aac tac ctg gta tgg cgc ctg gtg cta      1504
Tyr Ser Ala Arg Thr Met Gln Asn Tyr Leu Val Trp Arg Leu Val Leu
            380             385             390 gat cga att ggc agc ctg agc cag aga ttc aaa gag gcg cgt gtg gac      1552
Asp Arg Ile Gly Ser Leu Ser Gln Arg Phe Lys Glu Ala Arg Val Asp
        395             400             405 tac cgc aag gcg ctg tac ggc acg acc gtg gag gag gta cgc tgg cga      1600
Tyr Arg Lys Ala Leu Tyr Gly Thr Thr Val Glu Glu Val Arg Trp Arg
    410             415             420 gag tgt gtc agc tat gtc aac agt aac atg gag agc gcc gtg ggc tcc      1648
Glu Cys Val Ser Tyr Val Asn Ser Asn Met Glu Ser Ala Val Gly Ser
425             430             435 ctc tac atc aag cgg gcc ttc tcc aag gac agc aag agc acg gtc aga      1696
Leu Tyr Ile Lys Arg Ala Phe Ser Lys Asp Ser Lys Ser Thr Val Arg
440             445             450             455 gag ctg att gag aag ata agg tcc gtg ttt gtg gat aac ctg gat gag      1744
Glu Leu Ile Glu Lys Ile Arg Ser Val Phe Val Asp Asn Leu Asp Glu
        460             465             470 ctg aac tgg atg gac gag gaa tcc aag aag aag gcc cag gaa aag gcc      1792
Leu Asn Trp Met Asp Glu Glu Ser Lys Lys Lys Ala Gln Glu Lys Ala
    475             480             485 atg aat ata cgg gaa cag att ggc tac cct gac tac att ttg gaa gat      1840
Met Asn Ile Arg Glu Gln Ile Gly Tyr Pro Asp Tyr Ile Leu Glu Asp
490             495             500 aac aat aaa cac ctg gat gag gaa tac tcc agt ttg act ttc tat gag      1888
Asn Asn Lys His Leu Asp Glu Glu Tyr Ser Ser Leu Thr Phe Tyr Glu
505             510             515 gac ctg tat ttt gag aac gga ctt cag aac ctc aag aac aat gcc cag      1936
Asp Leu Tyr Phe Glu Asn Gly Leu Gln Asn Leu Lys Asn Asn Ala Gln
520             525             530             535 agg agc ctc aag aag ctt cgg gaa aag gtg gac cag aat ctc tgg atc      1984
Arg Ser Leu Lys Lys Leu Arg Glu Lys Val Asp Gln Asn Leu Trp Ile
        540             545             550 atc ggg gct gca gtg gtc aat gca ttc tac tcc cca aac aga aac cag      2032
Ile Gly Ala Ala Val Val Asn Ala Phe Tyr Ser Pro Asn Arg Asn Gln
    555             560             565 atc gtc ttt cca gca ggg att ctc cag ccg ccc ttc ttc agc aag gac      2080
Ile Val Phe Pro Ala Gly Ile Leu Gln Pro Pro Phe Phe Ser Lys Asp
570             575             580 caa cca cag tcc ttg aat ttt ggg ggc atc ggg atg gtg att ggg cac      2128
Gln Pro Gln Ser Leu Asn Phe Gly Gly Ile Gly Met Val Ile Gly His
585             590             595 gag atc aca cac ggc ttt gat gat aat ggt cgt aac ttt gac aag aac      2176
Glu Ile Thr His Gly Phe Asp Asp Asn Gly Arg Asn Phe Asp Lys Asn
600             605             610             615 ggc aac atg ctg gac tgg tgg agt aac ttc tcg gcc cgg cac ttc caa      2224
Gly Asn Met Leu Asp Trp Trp Ser Asn Phe Ser Ala Arg His Phe Gln
        620             625             630 cag cag tcg caa tgc atg atc tat cag tac ggc aac ttc tct tgg gaa      2272
Gln Gln Ser Gln Cys Met Ile Tyr Gln Tyr Gly Asn Phe Ser Trp Glu
    635             640             645 cta gca gac aac cag aat gtg aac gga ttc agt acc ctc ggg gag aac      2320
Leu Ala Asp Asn Gln Asn Val Asn Gly Phe Ser Thr Leu Gly Glu Asn
650             655             660
```

-continued

```
att gcc gac aac gga ggt gtg cga cag gca tac aag gct tac cta cgg      2368
Ile Ala Asp Asn Gly Gly Val Arg Gln Ala Tyr Lys Ala Tyr Leu Arg
            665                 670                 675 tgg ctg gct gat ggc ggc aaa gat cag cga ctg ccg gga ctg aac ctg      2416
Trp Leu Ala Asp Gly Gly Lys Asp Gln Arg Leu Pro Gly Leu Asn Leu
680                 685                 690                 695 acc tat gcc cag ctt ttc ttc atc aac tat gcc cag gtg tgg tgt ggg      2464
Thr Tyr Ala Gln Leu Phe Phe Ile Asn Tyr Ala Gln Val Trp Cys Gly
                700                 705                 710 tcc tat agg ccg gag ttc gcc gtc cag tcc atc aag acg gac gtc cac      2512
Ser Tyr Arg Pro Glu Phe Ala Val Gln Ser Ile Lys Thr Asp Val His
            715                 720                 725 agt cct ctt aag tac agg gtg ctg ggc tca cta cag aac ctg cca ggc      2560
Ser Pro Leu Lys Tyr Arg Val Leu Gly Ser Leu Gln Asn Leu Pro Gly
        730                 735                 740 ttc tct gag gca ttc cac tgc cca cga ggc agc ccc atg cac ccc atg      2608
Phe Ser Glu Ala Phe His Cys Pro Arg Gly Ser Pro Met His Pro Met
745                 750                 755 aag cga tgt cgc atc tgg tagccaaggc tgagctatgc tgcggccac              2656
Lys Arg Cys Arg Ile Trp
760                 765 gccccgccac ccagaggctt cgcgaatggt gtagctggca gagatgtgca ggtctttgcc    2716
tgaaggccac cggagccacc agccagccct ccgcgcccag cctagagtgt agccaccgc    2776 ccacacccgg gatgagtggt gccggtcctg cgcccctca ggccagtgag ggtcagcagc    2836
ccaggaagag cagtcagctg ccttccaccc tctccatagt gtgtggctaa atgttctcga   2896
gcttcagact tgagctaagt aaacgcttc                                     2925
```

<210> SEQ ID NO 13
<211> LENGTH: 765
<212> TYPE: PRT
<213> ORGANISM: Mus musculus

<400> SEQUENCE: 13

```
Met Val Glu Arg Ala Gly Trp Cys Arg Lys Lys Ser Pro Gly Phe Val
 1               5                  10                  15

Glu Tyr Gly Leu Met Val Leu Leu Leu Leu Leu Gly Ala Ile Val
            20                  25                  30

Thr Leu Gly Val Phe Tyr Ser Ile Gly Lys Gln Leu Pro Leu Leu Thr
        35                  40                  45

Ser Leu Leu His Phe Ser Trp Asp Glu Arg Thr Val Val Lys Arg Ala
    50                  55                  60

Leu Arg Asp Ser Ser Leu Lys Ser Asp Ile Cys Thr Thr Pro Ser Cys
65                  70                  75                  80

Val Ile Ala Ala Ala Arg Ile Leu Glu Asn Met Asp Gln Ser Arg Asn
                85                  90                  95

Pro Cys Glu Asn Phe Tyr Gln Tyr Ala Cys Gly Gly Trp Leu Arg His
            100                 105                 110

His Val Ile Pro Glu Thr Asn Ser Arg Tyr Ser Val Phe Asp Ile Leu
        115                 120                 125

Arg Asp Glu Leu Glu Val Ile Leu Lys Gly Val Leu Glu Asp Ser Thr
    130                 135                 140

Ser Gln His Arg Pro Ala Val Glu Lys Ala Lys Thr Leu Tyr Arg Ser
145                 150                 155                 160

Cys Met Asn Gln Ser Val Ile Glu Lys Arg Asp Ser Glu Pro Leu Leu
                165                 170                 175
```

-continued

```
Ser Val Leu Lys Met Val Gly Gly Trp Pro Val Ala Met Asp Lys Trp
            180                 185                 190

Asn Glu Thr Met Gly Leu Lys Trp Glu Leu Glu Arg Gln Leu Ala Val
            195                 200             205

Leu Asn Ser Gln Phe Asn Arg Arg Val Leu Ile Asp Leu Phe Ile Trp
            210                 215                 220

Asn Asp Asp Gln Asn Ser Ser Arg His Val Ile Tyr Ile Asp Gln Pro
225                 230                 235                 240

Thr Leu Gly Met Pro Ser Arg Glu Tyr Tyr Phe Gln Glu Asp Asn Asn
                245                 250                 255

His Lys Val Arg Lys Ala Tyr Leu Glu Phe Met Thr Ser Val Ala Thr
                260                 265                 270

Met Leu Arg Lys Asp Gln Asn Leu Ser Lys Glu Ser Ala Met Val Arg
            275                 280             285

Glu Glu Met Ala Glu Val Leu Glu Leu Glu Thr His Leu Ala Asn Ala
        290                 295                 300

Thr Val Pro Gln Glu Lys Arg His Asp Val Thr Ala Leu Tyr His Arg
305                 310                 315                 320

Met Asp Leu Met Glu Leu Gln Glu Arg Phe Gly Leu Lys Gly Phe Asn
                325                 330                 335

Trp Thr Leu Phe Ile Gln Asn Val Leu Ser Ser Val Glu Val Glu Leu
                340                 345                 350

Phe Pro Asp Glu Glu Val Val Val Tyr Gly Ile Pro Tyr Leu Glu Asn
                355                 360                 365

Leu Glu Asp Ile Ile Asp Ser Tyr Ser Ala Arg Thr Met Gln Asn Tyr
            370                 375                 380

Leu Val Trp Arg Leu Val Leu Asp Arg Ile Gly Ser Leu Ser Gln Arg
385                 390                 395                 400

Phe Lys Glu Ala Arg Val Asp Tyr Arg Lys Ala Leu Tyr Gly Thr Thr
                405                 410                 415

Val Glu Glu Val Arg Trp Arg Glu Cys Val Ser Tyr Val Asn Ser Asn
            420                 425                 430

Met Glu Ser Ala Val Gly Ser Leu Tyr Ile Lys Arg Ala Phe Ser Lys
        435                 440                 445

Asp Ser Lys Ser Thr Val Arg Glu Leu Ile Glu Lys Ile Arg Ser Val
450                 455                 460

Phe Val Asp Asn Leu Asp Glu Leu Asn Trp Met Asp Glu Glu Ser Lys
465                 470                 475                 480

Lys Lys Ala Gln Glu Lys Ala Met Asn Ile Arg Glu Gln Ile Gly Tyr
                485                 490                 495

Pro Asp Tyr Ile Leu Glu Asp Asn Lys His Leu Asp Glu Glu Tyr
                500                 505                 510

Ser Ser Leu Thr Phe Tyr Glu Asp Leu Tyr Phe Glu Asn Gly Leu Gln
            515                 520                 525

Asn Leu Lys Asn Ala Gln Arg Ser Leu Lys Lys Leu Arg Glu Lys
        530                 535                 540

Val Asp Gln Asn Leu Trp Ile Ile Gly Ala Ala Val Val Asn Ala Phe
545                 550                 555                 560

Tyr Ser Pro Asn Arg Asn Gln Ile Val Phe Pro Ala Gly Ile Leu Gln
                565                 570                 575

Pro Pro Phe Phe Ser Lys Asp Gln Pro Gln Ser Leu Asn Phe Gly Gly
                580                 585                 590

Ile Gly Met Val Ile Gly His Glu Ile Thr His Gly Phe Asp Asp Asn
```

-continued

```
              595                 600                 605
Gly Arg Asn Phe Asp Lys Asn Gly Asn Met Leu Asp Trp Trp Ser Asn
    610                 615                 620

Phe Ser Ala Arg His Phe Gln Gln Gln Ser Gln Cys Met Ile Tyr Gln
625                 630                 635                 640

Tyr Gly Asn Phe Ser Trp Glu Leu Ala Asp Asn Gln Asn Val Asn Gly
                645                 650                 655

Phe Ser Thr Leu Gly Glu Asn Ile Ala Asp Asn Gly Gly Val Arg Gln
                660                 665                 670

Ala Tyr Lys Ala Tyr Leu Arg Trp Leu Ala Asp Gly Gly Lys Asp Gln
                675                 680                 685

Arg Leu Pro Gly Leu Asn Leu Thr Tyr Ala Gln Leu Phe Phe Ile Asn
    690                 695                 700

Tyr Ala Gln Val Trp Cys Gly Ser Tyr Arg Pro Glu Phe Ala Val Gln
705                 710                 715                 720

Ser Ile Lys Thr Asp Val His Ser Pro Leu Lys Tyr Arg Val Leu Gly
                725                 730                 735

Ser Leu Gln Asn Leu Pro Gly Phe Ser Glu Ala Phe His Cys Pro Arg
                740                 745                 750

Gly Ser Pro Met His Pro Met Lys Arg Cys Arg Ile Trp
                755                 760                 765

<210> SEQ ID NO 14
<211> LENGTH: 2676
<212> TYPE: DNA
<213> ORGANISM: Homo sapiens
<220> FEATURE:
<221> NAME/KEY: CDS
<222> LOCATION: (7)..(2316)

<400> SEQUENCE: 14 gtgggg atg gtg gag agc gcc ggc cgt gca ggg cag aag cgc ccg ggg          48
       Met Val Glu Ser Ala Gly Arg Ala Gly Gln Lys Arg Pro Gly
         1               5                  10 ttc ctg gag ggg ggg ctg ctg ctg ctg ctg ctg gtg acc gct gcc             96
Phe Leu Glu Gly Gly Leu Leu Leu Leu Leu Leu Val Thr Ala Ala
 15                  20                  25                  30 ctg gtg gcc ttg ggt gtc ctc tac gcc gac cgc aga ggg aag cag ctg        144
Leu Val Ala Leu Gly Val Leu Tyr Ala Asp Arg Arg Gly Lys Gln Leu
                 35                  40                  45 cca cgc ctt gct agc cgg ctg tgc ttc tta cag gag gag agg acc ttt        192
Pro Arg Leu Ala Ser Arg Leu Cys Phe Leu Gln Glu Glu Arg Thr Phe
             50                  55                  60 gta aaa cga aaa ccc cga ggg atc cca gag gcc caa gag gtg agc gag        240
Val Lys Arg Lys Pro Arg Gly Ile Pro Glu Ala Gln Glu Val Ser Glu
         65                  70                  75 gtc tgc acc acc cct ggc tgc gtg ata gca gcc gcc agg atc ctc cag        288
Val Cys Thr Thr Pro Gly Cys Val Ile Ala Ala Ala Arg Ile Leu Gln
     80                  85                  90 aac atg gac ccg acc acg gaa ccg tgt gac gac ttc tac cag ttt gca        336
Asn Met Asp Pro Thr Thr Glu Pro Cys Asp Asp Phe Tyr Gln Phe Ala
 95                 100                 105                 110 tgc gga ggc tgg ctg cgg cgc cac gtg atc cct gag acc aac tca aga        384
Cys Gly Gly Trp Leu Arg Arg His Val Ile Pro Glu Thr Asn Ser Arg
                115                 120                 125 tac agc atc ttt gac gtc ctc cgc gac gag ctg gag gtc atc ctc aaa        432
Tyr Ser Ile Phe Asp Val Leu Arg Asp Glu Leu Glu Val Ile Leu Lys
            130                 135                 140
```

-continued

| | | |
|---|---|---|
| gcg gtg ctg gag aat tcg act gcc aag gac cgg ccg gct gtg gag aag<br>Ala Val Leu Glu Asn Ser Thr Ala Lys Asp Arg Pro Ala Val Glu Lys<br>     145                    150                      155 | | 480 |
| gcc agg acg ctg tac cgc tcc tgc atg aac cag agt gtg ata gag aag<br>Ala Arg Thr Leu Tyr Arg Ser Cys Met Asn Gln Ser Val Ile Glu Lys<br>160                    165                      170 | | 528 |
| cga ggc tct cag ccc ctg ctg gac atc ttg gag gtg gtg gga ggc tgg<br>Arg Gly Ser Gln Pro Leu Leu Asp Ile Leu Glu Val Val Gly Gly Trp<br>175                      180                      185                      190 | | 576 |
| ccg gtg gcg atg gac agg tgg aac gag acc gta gga ctc gag tgg gag<br>Pro Val Ala Met Asp Arg Trp Asn Glu Thr Val Gly Leu Glu Trp Glu<br>                      195                      200                      205 | | 624 |
| ctg gag cgg cag ctg gcg ctg atg aac tca cag ttc aac agg cgc gtc<br>Leu Glu Arg Gln Leu Ala Leu Met Asn Ser Gln Phe Asn Arg Arg Val<br>                      210                      215                      220 | | 672 |
| ctc atc gac ctc ttc atc tgg aac gac gac cag aac tcc agc cgg cac<br>Leu Ile Asp Leu Phe Ile Trp Asn Asp Asp Gln Asn Ser Ser Arg His<br>                      225                      230                      235 | | 720 |
| atc atc tac ata gac cag ccc acc ttg ggc atg ccc tcc cga gag tac<br>Ile Ile Tyr Ile Asp Gln Pro Thr Leu Gly Met Pro Ser Arg Glu Tyr<br>                      240                      245                      250 | | 768 |
| tac ttc aac ggc ggc agc aac cgg aag gtg cgg gaa gcc tac ctg cag<br>Tyr Phe Asn Gly Gly Ser Asn Arg Lys Val Arg Glu Ala Tyr Leu Gln<br>255                      260                      265                      270 | | 816 |
| ttc atg gtg tca gtg gcc acg ttg ctg cgg gag gat gca aac ctg ccc<br>Phe Met Val Ser Val Ala Thr Leu Leu Arg Glu Asp Ala Asn Leu Pro<br>                                    275                      280                      285 | | 864 |
| agg gac agc tgc ctg gtg cag gag gac atg gtg cag gtt ctg gag ctg<br>Arg Asp Ser Cys Leu Val Gln Glu Asp Met Val Gln Val Leu Glu Leu<br>                      290                      295                      300 | | 912 |
| gag aca cag ctg gcc aag gcc acg gta ccc cag gag gag aga cac gac<br>Glu Thr Gln Leu Ala Lys Ala Thr Val Pro Gln Glu Glu Arg His Asp<br>                                    305                      310                      315 | | 960 |
| gtc atc gcc ttg tac cac cgg atg gga ctg gag gag ctg caa agc cag<br>Val Ile Ala Leu Tyr His Arg Met Gly Leu Glu Glu Leu Gln Ser Gln<br>320                      325                      330 | | 1008 |
| ttt ggc ctg aag gga ttt aac tgg act ctg ttc ata caa act gtg cta<br>Phe Gly Leu Lys Gly Phe Asn Trp Thr Leu Phe Ile Gln Thr Val Leu<br>335                      340                      345                      350 | | 1056 |
| tcc tct gtc aaa atc aag ctg ctg cca gat gag gaa gtg gtg gtc tat<br>Ser Ser Val Lys Ile Lys Leu Leu Pro Asp Glu Glu Val Val Val Tyr<br>                      355                      360                      365 | | 1104 |
| ggc atc ccc tac ctg cag aac ctt gaa aac atc atc gac acc tac tca<br>Gly Ile Pro Tyr Leu Gln Asn Leu Glu Asn Ile Ile Asp Thr Tyr Ser<br>                                    370                      375                      380 | | 1152 |
| gcc agg acc ata cag aac tac ctg gtc tgg cgc ctg gtg ctg gac cgc<br>Ala Arg Thr Ile Gln Asn Tyr Leu Val Trp Arg Leu Val Leu Asp Arg<br>                      385                      390                      395 | | 1200 |
| att ggt agc cta agc cag aga ttc aag gac aca cga gtg aac tac cgc<br>Ile Gly Ser Leu Ser Gln Arg Phe Lys Asp Thr Arg Val Asn Tyr Arg<br>400                      405                      410 | | 1248 |
| aag gcg ctg ttt ggc aca atg gtg gag gag gtg cgc tgg cgt gaa tgt<br>Lys Ala Leu Phe Gly Thr Met Val Glu Glu Val Arg Trp Arg Glu Cys<br>415                      420                      425                      430 | | 1296 |
| gtg ggc tac gtc aac agc aac atg gag aac gcc gtg ggc tcc ctc tac<br>Val Gly Tyr Val Asn Ser Asn Met Glu Asn Ala Val Gly Ser Leu Tyr<br>                                    435                      440                      445 | | 1344 |
| gtc agg gag gcg ttc cct gga gac agc aag agc atg gtc aga gaa ctc<br>Val Arg Glu Ala Phe Pro Gly Asp Ser Lys Ser Met Val Arg Glu Leu<br>                      450                      455                      460 | | 1392 |

-continued

| | | |
|---|---|---|
| att gac aag gtg cgg aca gtg ttt gtg gag acg ctg gac gag ctg ggc<br>Ile Asp Lys Val Arg Thr Val Phe Val Glu Thr Leu Asp Glu Leu Gly<br>465 470 475 | | 1440 |
| tgg atg gac gag gag tcc aag aag aag gcg cag gag aag gcc atg agc<br>Trp Met Asp Glu Glu Ser Lys Lys Lys Ala Gln Glu Lys Ala Met Ser<br>480 485 490 | | 1488 |
| atc cgg gag cag atc ggg cac cct gac tac atc ctg gag gag atg aac<br>Ile Arg Glu Gln Ile Gly His Pro Asp Tyr Ile Leu Glu Glu Met Asn<br>495 500 505 510 | | 1536 |
| agg cgc ctg gac gag gag tac tcc aat ctg aac ttc tca gag gac ctg<br>Arg Arg Leu Asp Glu Glu Tyr Ser Asn Leu Asn Phe Ser Glu Asp Leu<br>515 520 525 | | 1584 |
| tac ttt gag aac agt ctg cag aac ctc aag gtg gcc gcc cag cgg agc<br>Tyr Phe Glu Asn Ser Leu Gln Asn Leu Lys Val Gly Ala Gln Arg Ser<br>530 535 540 | | 1632 |
| ctc agg aag ctt cgg gaa aag gtg gac cca aat ctc tgg atc atc ggg<br>Leu Arg Lys Leu Arg Glu Lys Val Asp Pro Asn Leu Trp Ile Ile Gly<br>545 550 555 | | 1680 |
| gcg gcg gtg gtc aat gcg ttc tac tcc cca aac cga aac cag att gta<br>Ala Ala Val Val Asn Ala Phe Tyr Ser Pro Asn Arg Asn Gln Ile Val<br>560 565 570 | | 1728 |
| ttc cct gcc ggg atc ctc cag ccc ccc ttc ttc agc aag gag cag cca<br>Phe Pro Ala Gly Ile Leu Gln Pro Pro Phe Phe Ser Lys Glu Gln Pro<br>575 580 585 590 | | 1776 |
| cag gcc ttg aac ttt gga ggc att ggg atg gtg atc ggg cac gag atc<br>Gln Ala Leu Asn Phe Gly Gly Ile Gly Met Val Ile Gly His Glu Ile<br>595 600 605 | | 1824 |
| acg cac ggc ttt gac gac aat ggc cgg aac ttc gac aag aat ggc aac<br>Thr His Gly Phe Asp Asp Asn Gly Arg Asn Phe Asp Lys Asn Gly Asn<br>610 615 620 | | 1872 |
| atg atg gat tgg tgg agt aac ttc tcc acc cag cac ttc cgg gag cag<br>Met Met Asp Trp Trp Ser Asn Phe Ser Thr Gln His Phe Arg Glu Gln<br>625 630 635 | | 1920 |
| tca gag tgc atg atc tac cag tac ggc aac tac tcc tgg gac ctg gca<br>Ser Glu Cys Met Ile Tyr Gln Tyr Gly Asn Tyr Ser Trp Asp Leu Ala<br>640 645 650 | | 1968 |
| gac gaa cag aac gtg aac gga ttc aac acc ctt ggg gaa aac att gct<br>Asp Glu Gln Asn Val Asn Gly Phe Asn Thr Leu Gly Glu Asn Ile Ala<br>655 660 665 670 | | 2016 |
| gac aac gga ggg gtg cgg caa gcc tat aag gcc tac ctc aag tgg atg<br>Asp Asn Gly Gly Val Arg Gln Ala Tyr Lys Ala Tyr Leu Lys Trp Met<br>675 680 685 | | 2064 |
| gca gag ggt ggc aag gac cag cag ctg ccc ggc ctg gat ctc acc cat<br>Ala Glu Gly Gly Lys Asp Gln Gln Leu Pro Gly Leu Asp Leu Thr His<br>690 695 700 | | 2112 |
| gag cag ctc ttc ttc atc aac tat gcc cag gtg tgg tgc ggg tcc tac<br>Glu Gln Leu Phe Phe Ile Asn Tyr Ala Gln Val Trp Cys Gly Ser Tyr<br>705 710 715 | | 2160 |
| cgg ccc gag ttc gcc atc caa tcc atc aag aca gac gtc cac agt ccc<br>Arg Pro Glu Phe Ala Ile Gln Ser Ile Lys Thr Asp Val His Ser Pro<br>720 725 730 | | 2208 |
| ctg aag tac agg gta ctg ggg tcg ctg cag aac ctg gcc gcc ttc gca<br>Leu Lys Tyr Arg Val Leu Gly Ser Leu Gln Asn Leu Ala Ala Phe Ala<br>735 740 745 750 | | 2256 |
| gac acg ttc cac tgt gcc cgg ggc acc ccc atg cac ccc aag gag cga<br>Asp Thr Phe His Cys Ala Arg Gly Thr Pro Met His Pro Lys Glu Arg<br>755 760 765 | | 2304 |
| tgc cgc gtg tgg tagccaaggc cctgccgcgc tgtgcggccc acgcccaccc<br>Cys Arg Val Trp | | 2356 |

```
                    770
gctgctcgga ggcatctgtg cgaaggtgca gctagcggcg acccagtgta cgtcccgccc    2416
cggccaacca tgccaagcct gcctgccagg cctctgcgcc tggcctaggg tgcagccacc    2476
tgcctgacac ccagggatga gcagtgtcca gtgcagtacc tggaccggag ccccttcac    2536 agacaccccgc ggggctcagt gcccccgtca caactctgta gagacaatca actgtgtcct   2596 gcccacccctt caaggtgcat tgtcttccag tatctacagc ttcagaactt gagctaagta   2656
aatgctttca aagaaaaaaa                                                2676
```

<210> SEQ ID NO 15
<211> LENGTH: 770
<212> TYPE: PRT
<213> ORGANISM: Homo sapiens

<400> SEQUENCE: 15

```
Met Val Glu Ser Ala Gly Arg Ala Gly Gln Lys Arg Pro Gly Phe Leu
  1               5                  10                  15

Glu Gly Gly Leu Leu Leu Leu Leu Val Thr Ala Ala Leu Val
             20                  25                  30

Ala Leu Gly Val Leu Tyr Ala Asp Arg Arg Gly Lys Gln Leu Pro Arg
         35                  40                  45

Leu Ala Ser Arg Leu Cys Phe Leu Gln Glu Glu Arg Thr Phe Val Lys
     50                  55                  60

Arg Lys Pro Arg Gly Ile Pro Glu Ala Gln Glu Val Ser Glu Val Cys
 65                  70                  75                  80

Thr Thr Pro Gly Cys Val Ile Ala Ala Arg Ile Leu Gln Asn Met
                 85                  90                  95

Asp Pro Thr Thr Glu Pro Cys Asp Asp Phe Tyr Gln Phe Ala Cys Gly
            100                 105                 110

Gly Trp Leu Arg Arg His Val Ile Pro Glu Thr Asn Ser Arg Tyr Ser
        115                 120                 125

Ile Phe Asp Val Leu Arg Asp Glu Leu Glu Val Ile Leu Lys Ala Val
    130                 135                 140

Leu Glu Asn Ser Thr Ala Lys Asp Arg Pro Ala Val Glu Lys Ala Arg
145                 150                 155                 160

Thr Leu Tyr Arg Ser Cys Met Asn Gln Ser Val Ile Glu Lys Arg Gly
                165                 170                 175

Ser Gln Pro Leu Leu Asp Ile Leu Glu Val Val Gly Gly Trp Pro Val
            180                 185                 190

Ala Met Asp Arg Trp Asn Glu Thr Val Gly Leu Glu Trp Glu Leu Glu
        195                 200                 205

Arg Gln Leu Ala Leu Met Asn Ser Gln Phe Asn Arg Arg Val Leu Ile
    210                 215                 220

Asp Leu Phe Ile Trp Asn Asp Asp Gln Asn Ser Ser Arg His Ile Ile
225                 230                 235                 240

Tyr Ile Asp Gln Pro Thr Leu Gly Met Pro Ser Arg Glu Tyr Tyr Phe
                245                 250                 255

Asn Gly Gly Ser Asn Arg Lys Val Arg Glu Ala Tyr Leu Gln Phe Met
            260                 265                 270

Val Ser Val Ala Thr Leu Leu Arg Glu Asp Ala Asn Leu Pro Arg Asp
        275                 280                 285

Ser Cys Leu Val Gln Glu Asp Met Val Gln Val Leu Glu Leu Glu Thr
    290                 295                 300
```

-continued

```
Gln Leu Ala Lys Ala Thr Val Pro Gln Glu Arg His Asp Val Ile
305                 310                 315                 320

Ala Leu Tyr His Arg Met Gly Leu Glu Glu Leu Gln Ser Gln Phe Gly
                325                 330                 335

Leu Lys Gly Phe Asn Trp Thr Leu Phe Ile Gln Thr Val Leu Ser Ser
            340                 345                 350

Val Lys Ile Lys Leu Leu Pro Asp Glu Glu Val Val Tyr Gly Ile
        355                 360                 365

Pro Tyr Leu Gln Asn Leu Glu Asn Ile Ile Asp Thr Tyr Ser Ala Arg
    370                 375                 380

Thr Ile Gln Asn Tyr Leu Val Trp Arg Leu Val Leu Asp Arg Ile Gly
385                 390                 395                 400

Ser Leu Ser Gln Arg Phe Lys Asp Thr Arg Val Asn Tyr Arg Lys Ala
                405                 410                 415

Leu Phe Gly Thr Met Val Glu Val Arg Trp Arg Glu Cys Val Gly
            420                 425                 430

Tyr Val Asn Ser Asn Met Glu Asn Ala Val Gly Ser Leu Tyr Val Arg
        435                 440                 445

Glu Ala Phe Pro Gly Asp Ser Lys Ser Met Val Arg Glu Leu Ile Asp
    450                 455                 460

Lys Val Arg Thr Val Phe Val Glu Thr Leu Asp Glu Leu Gly Trp Met
465                 470                 475                 480

Asp Glu Glu Ser Lys Lys Ala Gln Glu Lys Ala Met Ser Ile Arg
                485                 490                 495

Glu Gln Ile Gly His Pro Asp Tyr Ile Leu Glu Met Asn Arg Arg
            500                 505                 510

Leu Asp Glu Glu Tyr Ser Asn Leu Asn Phe Ser Glu Asp Leu Tyr Phe
        515                 520                 525

Glu Asn Ser Leu Gln Asn Leu Lys Val Gly Ala Gln Arg Ser Leu Arg
    530                 535                 540

Lys Leu Arg Glu Lys Val Asp Pro Asn Leu Trp Ile Ile Gly Ala Ala
545                 550                 555                 560

Val Val Asn Ala Phe Tyr Ser Pro Asn Arg Asn Gln Ile Val Phe Pro
                565                 570                 575

Ala Gly Ile Leu Gln Pro Pro Phe Phe Ser Lys Glu Gln Pro Gln Ala
            580                 585                 590

Leu Asn Phe Gly Gly Ile Gly Met Val Ile Gly His Glu Ile Thr His
        595                 600                 605

Gly Phe Asp Asp Asn Gly Arg Asn Phe Asp Lys Asn Gly Asn Met Met
    610                 615                 620

Asp Trp Trp Ser Asn Phe Ser Thr Gln His Phe Arg Glu Gln Ser Glu
625                 630                 635                 640

Cys Met Ile Tyr Gln Tyr Gly Asn Tyr Ser Trp Asp Leu Ala Asp Glu
                645                 650                 655

Gln Asn Val Asn Gly Phe Asn Thr Leu Gly Glu Asn Ile Ala Asp Asn
            660                 665                 670

Gly Gly Val Arg Gln Ala Tyr Lys Ala Tyr Leu Lys Trp Met Ala Glu
        675                 680                 685

Gly Gly Lys Asp Gln Gln Leu Pro Gly Leu Asp Leu Thr His Glu Gln
    690                 695                 700

Leu Phe Phe Ile Asn Tyr Ala Gln Val Trp Cys Gly Ser Tyr Arg Pro
705                 710                 715                 720

Glu Phe Ala Ile Gln Ser Ile Lys Thr Asp Val His Ser Pro Leu Lys
```

```
                      725                 730                 735
Tyr Arg Val Leu Gly Ser Leu Gln Asn Leu Ala Ala Phe Ala Asp Thr
                740                 745                 750
Phe His Cys Ala Arg Gly Thr Pro Met His Pro Lys Glu Arg Cys Arg
            755                 760                 765
Val Trp
    770

<210> SEQ ID NO 16
<211> LENGTH: 2871
<212> TYPE: DNA
<213> ORGANISM: Homo sapiens
<220> FEATURE:
<221> NAME/KEY: CDS
<222> LOCATION: (205)..(2529)

<400> SEQUENCE: 16
ggcgctggga gacaccggac gcccgctcgg ctgcgctgcg gctcaggccc ccgctcggcc      60
cgacccgctc ggtcaccgcc ggctcgggcg cgcacctgcc ggctgcggcc ccagggccat     120
gcggaggccc acgaggaggc cggcggccac gcgcatcccg tagcccaggt ggcccaggtc     180
tgcaccgcgg cggcctcggc gccg atg gag ccc ccg tat tcg ctg acg gcg       231
                           Met Glu Pro Pro Tyr Ser Leu Thr Ala
                             1               5 cac tac gat gag ttc caa gag gtc aag tac gtg agc cgc tgc ggc gcg      279
His Tyr Asp Glu Phe Gln Glu Val Lys Tyr Val Ser Arg Cys Gly Ala
 10                  15                  20                  25 ggg ggc gcg cgc ggg gcc tcc ctg ccc ccg ggc ttc ccg ttg ggc gct      327
Gly Gly Ala Arg Gly Ala Ser Leu Pro Pro Gly Phe Pro Leu Gly Ala
                 30                  35                  40 gcg cgc agc gcc acc ggg gcc cgg tcc ggg ctg ccg cgc tgg aac cgg      375
Ala Arg Ser Ala Thr Gly Ala Arg Ser Gly Leu Pro Arg Trp Asn Arg
             45                  50                  55 cgc gag gtg tgc ctg ctg tcg ggg ctg gtg ttc gcc gcc ggc ctc tgc      423
Arg Glu Val Cys Leu Leu Ser Gly Leu Val Phe Ala Ala Gly Leu Cys
         60                  65                  70 gcc att ctg gcg gct atg ctg gcc ctc aag tac ctg ggc ccg gtc gcg      471
Ala Ile Leu Ala Ala Met Leu Ala Leu Lys Tyr Leu Gly Pro Val Ala
 75                  80                  85 gcc ggc ggc ggc gcc tgt ccc gag ggc tgc cct gag cgc aag gcc ttc      519
Ala Gly Gly Gly Ala Cys Pro Glu Gly Cys Pro Glu Arg Lys Ala Phe
 90                  95                 100                 105 gcg cgc gcc gct cgc ttc ctg gcc gcc aac ctg gac gcc agc atc gac      567
Ala Arg Ala Ala Arg Phe Leu Ala Ala Asn Leu Asp Ala Ser Ile Asp
                110                 115                 120 cca tgc cag gac ttc tac tcg ttc gcc tgc ggc ggt tgg ctg cgg cgc      615
Pro Cys Gln Asp Phe Tyr Ser Phe Ala Cys Gly Gly Trp Leu Arg Arg
            125                 130                 135 cac gcc atc ccc gac gac aag ctc acc tat ggc acc atc gcg gca atc      663
His Ala Ile Pro Asp Asp Lys Leu Thr Tyr Gly Thr Ile Ala Ala Ile
        140                 145                 150 ggc gag caa aac gag gag cgc cta cgg cgc ctg ctg gcg cgg ccc ggg      711
Gly Glu Gln Asn Glu Glu Arg Leu Arg Arg Leu Leu Ala Arg Pro Gly
    155                 160                 165 ggt ggg cct ggc ggc gcg gcc cag cgc aag gtg cgc gcc ttc ttc cgc      759
Gly Gly Pro Gly Gly Ala Ala Gln Arg Lys Val Arg Ala Phe Phe Arg
170                 175                 180                 185 tcg tgc ctc gac atg cgc gag atc gag cga ctg ggc ccg cga ccc atg      807
Ser Cys Leu Asp Met Arg Glu Ile Glu Arg Leu Gly Pro Arg Pro Met
                190                 195                 200
```

```
cta gag gtc atc gag gac tgc ggg ggc tgg gac ctg ggc ggc gcg gag        855
Leu Glu Val Ile Glu Asp Cys Gly Gly Trp Asp Leu Gly Gly Ala Glu
            205                 210                 215 gag cgt ccg ggg gtc gcg gcg cga tgg gac ctc aac cgg ctg ctg tac        903
Glu Arg Pro Gly Val Ala Ala Arg Trp Asp Leu Asn Arg Leu Leu Tyr
        220                 225                 230 aag gcg cag ggc gtg tac agc gcc gcc gcg ctc ttc tcg ctc acg gtc        951
Lys Ala Gln Gly Val Tyr Ser Ala Ala Ala Leu Phe Ser Leu Thr Val
    235                 240                 245 agc ctg gac gac agg aac tcc tcg cgc tac gtc atc cgc att gac cag        999
Ser Leu Asp Asp Arg Asn Ser Ser Arg Tyr Val Ile Arg Ile Asp Gln
250                 255                 260                 265 gat ggg ctc acc ctg cca gag agg acc ctg tac ctc gct cag gat gag       1047
Asp Gly Leu Thr Leu Pro Glu Arg Thr Leu Tyr Leu Ala Gln Asp Glu
                270                 275                 280 gac agt gag aag gtc ctg gca gca tac agg gtg ttc atg gag cga gtg       1095
Asp Ser Glu Lys Val Leu Ala Ala Tyr Arg Val Phe Met Glu Arg Val
            285                 290                 295 ctc agc ctc ctg ggt gca gac gct gtg gaa cag aag gcc caa gag atc       1143
Leu Ser Leu Leu Gly Ala Asp Ala Val Glu Gln Lys Ala Gln Glu Ile
        300                 305                 310 ctg caa gtg gag cag cag ctg gcc aac atc act gtg tca gag tat gac       1191
Leu Gln Val Glu Gln Gln Leu Ala Asn Ile Thr Val Ser Glu Tyr Asp
    315                 320                 325 gac cta cgg cga gat gtc agc tcc atg tac aac aag gtg acg ctg ggg       1239
Asp Leu Arg Arg Asp Val Ser Ser Met Tyr Asn Lys Val Thr Leu Gly
330                 335                 340                 345 cag ctg cag aag atc acc ccc cac ttg cgg tgg aag tgg ctg cta gac       1287
Gln Leu Gln Lys Ile Thr Pro His Leu Arg Trp Lys Trp Leu Leu Asp
                350                 355                 360 cag atc ttc cag gag gac ttc tca gag gaa gag gag gtg gtg ctg ctg       1335
Gln Ile Phe Gln Glu Asp Phe Ser Glu Glu Glu Glu Val Val Leu Leu
            365                 370                 375 gcg aca gac tac atg cag cag gtg tcg cag ctc atc cgc tcc aca ccc       1383
Ala Thr Asp Tyr Met Gln Gln Val Ser Gln Leu Ile Arg Ser Thr Pro
        380                 385                 390 cac cgg gtc ctg cac aac tac ctg gtg tgg cgc gtg gtg gtg gtc ctg       1431
His Arg Val Leu His Asn Tyr Leu Val Trp Arg Val Val Val Val Leu
    395                 400                 405 agt gaa cac ctg tcc ccg cca ttc cgt gag gca ctg cac gag ctg gca       1479
Ser Glu His Leu Ser Pro Pro Phe Arg Glu Ala Leu His Glu Leu Ala
410                 415                 420                 425 cag gag atg gag ggc agc gac aag cca cag gag ctg gcc cgg gtc tgc       1527
Gln Glu Met Glu Gly Ser Asp Lys Pro Gln Glu Leu Ala Arg Val Cys
                430                 435                 440 ttg ggc cag gcc aat cgc cac ttt ggc atg gcg ctt gcc ctc ttt           1575
Leu Gly Gln Ala Asn Arg His Phe Gly Met Ala Leu Gly Ala Leu Phe
            445                 450                 455 gta cat gag cac ttc tca gct gcc agc aaa gcc aag gtg cag cag cta       1623
Val His Glu His Phe Ser Ala Ala Ser Lys Ala Lys Val Gln Gln Leu
        460                 465                 470 gtg gaa gac atc aag tac atc ctg ggc cag cgc ctg gag gag ctg gac       1671
Val Glu Asp Ile Lys Tyr Ile Leu Gly Gln Arg Leu Glu Glu Leu Asp
    475                 480                 485 tgg atg gac gcc gag acc agg gct gct gct cgg gcc aag ctc cag tac       1719
Trp Met Asp Ala Glu Thr Arg Ala Ala Ala Arg Ala Lys Leu Gln Tyr
490                 495                 500                 505 atg atg gtg atg gtc ggc tac ccg gac ttc ctg ctg aaa ccc gat gct       1767
Met Met Val Met Val Gly Tyr Pro Asp Phe Leu Leu Lys Pro Asp Ala
```

```
                 510              515              520
gtg gac aag gag tat gag ttt gag gtc cat gag aag acc tac ttc aag    1815
Val Asp Lys Glu Tyr Glu Phe Glu Val His Glu Lys Thr Tyr Phe Lys
                 525              530              535 aac atc ttg aac agc atc cgc ttc agc atc cag ctc tca gtt aag aag    1863
Asn Ile Leu Asn Ser Ile Arg Phe Ser Ile Gln Leu Ser Val Lys Lys
             540              545              550 att cgg cag gag gtg gac aag tcc acg tgg ctg ctc ccc cca cag gcg    1911
Ile Arg Gln Glu Val Asp Lys Ser Thr Trp Leu Leu Pro Pro Gln Ala
555              560              565 ctc aat gcc tac tat cta ccc aac aag aac cag atg gtg ttc ccc gcg    1959
Leu Asn Ala Tyr Tyr Leu Pro Asn Lys Asn Gln Met Val Phe Pro Ala
570              575              580              585 ggc atc ctg cag ccc acc ctg tac gac cct gac ttc cca cag tct ctc    2007
Gly Ile Leu Gln Pro Thr Leu Tyr Asp Pro Asp Phe Pro Gln Ser Leu
             590              595              600 aac tac ggg ggc atc ggc acc atc att gga cat gag ctg acc cac ggc    2055
Asn Tyr Gly Gly Ile Gly Thr Ile Ile Gly His Glu Leu Thr His Gly
                 605              610              615 tac gac gac tgg ggg ggc cag tat gac cgc tca ggg aac ctg ctg cac    2103
Tyr Asp Asp Trp Gly Gly Gln Tyr Asp Arg Ser Gly Asn Leu Leu His
             620              625              630 tgg tgg acg gag gcc tcc tac agc cgc ttc ctg cga aag gct gag tgc    2151
Trp Trp Thr Glu Ala Ser Tyr Ser Arg Phe Leu Arg Lys Ala Glu Cys
635              640              645 atc gtc cgt ctc tat gac aac ttc act gtc tac aac cag cgg gtg aac    2199
Ile Val Arg Leu Tyr Asp Asn Phe Thr Val Tyr Asn Gln Arg Val Asn
650              655              660              665 ggg aaa cac acg ctt ggg gag aac atc gca gat atg ggc ggc ctc aag    2247
Gly Lys His Thr Leu Gly Glu Asn Ile Ala Asp Met Gly Gly Leu Lys
             670              675              680 ctg gcc tac cac gcc tat cag aag tgg gtg cgg gag cac ggc cca gag    2295
Leu Ala Tyr His Ala Tyr Gln Lys Trp Val Arg Glu His Gly Pro Glu
                 685              690              695 cac cca ctt ccc cgg ctc aag tac aca cat gac cag ctc ttc ttc att    2343
His Pro Leu Pro Arg Leu Lys Tyr Thr His Asp Gln Leu Phe Phe Ile
                 700              705              710 gcc ttt gcc cag aac tgg tgc atc aag cgg cgg tcg cag tcc atc tac    2391
Ala Phe Ala Gln Asn Trp Cys Ile Lys Arg Arg Ser Gln Ser Ile Tyr
715              720              725 ctg cag gtg ctg act gac aag cat gcc cct gag cac tac agg gtg ctg    2439
Leu Gln Val Leu Thr Asp Lys His Ala Pro Glu His Tyr Arg Val Leu
730              735              740              745 ggc agt gtg tcc cag ttt gag gag ttt ggc cgg gtt tta cac tgt cca    2487
Gly Ser Val Ser Gln Phe Glu Glu Phe Gly Arg Val Leu His Cys Pro
             750              755              760 aag gtc tca ccc atg aac cct gcc cac aag tgt tcc gtg tgg              2529
Lys Val Ser Pro Met Asn Pro Ala His Lys Cys Ser Val Trp
             765              770              775 tgaccctggc tgcccgcctg cacgccccca ctgcccccgc acgaatcacc tcctgctggc    2589
taccggggca ggcatgcacc cggtgccagc cccgctctgg gcaccacctg ccttccagcc    2649
cctccaggac ccggtccccc tgctgcccct cacttcagga ggggcctgga gcagggtgag    2709
gctggacttt gggggggctgt gagggaaata tactgggggtc cccagattct gctctaaggg    2769
ggccagaccc tctgccaggc tggattgtac gggcccccacc ttcgctgtgt tcttgctgca    2829
agtctggtca aataaatcac tgcactgtta aaaaaaaaa aa                         2871
```

-continued

<210> SEQ ID NO 17
<211> LENGTH: 775
<212> TYPE: PRT
<213> ORGANISM: Homo sapiens

<400> SEQUENCE: 17

```
Met Glu Pro Pro Tyr Ser Leu Thr Ala His Tyr Asp Glu Phe Gln Glu
  1               5                  10                  15

Val Lys Tyr Val Ser Arg Cys Gly Ala Gly Ala Arg Gly Ala Ser
             20                  25                  30

Leu Pro Pro Gly Phe Pro Leu Gly Ala Ala Arg Ser Ala Thr Gly Ala
             35                  40                  45

Arg Ser Gly Leu Pro Arg Trp Asn Arg Arg Glu Val Cys Leu Leu Ser
 50                  55                  60

Gly Leu Val Phe Ala Ala Gly Leu Cys Ala Ile Leu Ala Ala Met Leu
 65                  70                  75                  80

Ala Leu Lys Tyr Leu Gly Pro Val Ala Gly Gly Ala Cys Pro
             85                  90                  95

Glu Gly Cys Pro Glu Arg Lys Ala Phe Ala Arg Ala Arg Phe Leu
            100                 105                 110

Ala Ala Asn Leu Asp Ala Ser Ile Asp Pro Cys Gln Asp Phe Tyr Ser
            115                 120                 125

Phe Ala Cys Gly Gly Trp Leu Arg Arg His Ala Ile Pro Asp Asp Lys
130                 135                 140

Leu Thr Tyr Gly Thr Ile Ala Ala Ile Gly Glu Gln Asn Glu Glu Arg
145                 150                 155                 160

Leu Arg Arg Leu Leu Ala Arg Pro Gly Gly Pro Gly Gly Ala Ala
            165                 170                 175

Gln Arg Lys Val Arg Ala Phe Phe Arg Ser Cys Leu Asp Met Arg Glu
            180                 185                 190

Ile Glu Arg Leu Gly Pro Arg Pro Met Leu Glu Val Ile Glu Asp Cys
            195                 200                 205

Gly Gly Trp Asp Leu Gly Gly Ala Glu Glu Arg Pro Gly Val Ala Ala
210                 215                 220

Arg Trp Asp Leu Asn Arg Leu Leu Tyr Lys Ala Gln Gly Val Tyr Ser
225                 230                 235                 240

Ala Ala Ala Leu Phe Ser Leu Thr Val Ser Leu Asp Asp Arg Asn Ser
                245                 250                 255

Ser Arg Tyr Val Ile Arg Ile Asp Gln Asp Gly Leu Thr Leu Pro Glu
            260                 265                 270

Arg Thr Leu Tyr Leu Ala Gln Asp Glu Asp Ser Glu Lys Val Leu Ala
            275                 280                 285

Ala Tyr Arg Val Phe Met Glu Arg Val Leu Ser Leu Leu Gly Ala Asp
            290                 295                 300

Ala Val Glu Gln Lys Ala Gln Glu Ile Leu Gln Val Glu Gln Gln Leu
305                 310                 315                 320

Ala Asn Ile Thr Val Ser Glu Tyr Asp Asp Leu Arg Arg Asp Val Ser
                325                 330                 335

Ser Met Tyr Asn Lys Val Thr Leu Gly Gln Leu Gln Lys Ile Thr Pro
            340                 345                 350

His Leu Arg Trp Lys Trp Leu Leu Asp Gln Ile Phe Gln Glu Asp Phe
            355                 360                 365

Ser Glu Glu Glu Val Val Leu Leu Ala Thr Asp Tyr Met Gln Gln
            370                 375                 380
```

-continued

```
Val Ser Gln Leu Ile Arg Ser Thr Pro His Arg Val Leu His Asn Tyr
385                 390                 395                 400

Leu Val Trp Arg Val Val Val Leu Ser Glu His Leu Ser Pro Pro
            405                 410                 415

Phe Arg Glu Ala Leu His Glu Leu Ala Gln Glu Met Glu Gly Ser Asp
            420                 425                 430

Lys Pro Gln Glu Leu Ala Arg Val Cys Leu Gly Gln Ala Asn Arg His
            435                 440                 445

Phe Gly Met Ala Leu Gly Ala Leu Phe Val His Glu His Phe Ser Ala
            450                 455                 460

Ala Ser Lys Ala Lys Val Gln Gln Leu Val Glu Asp Ile Lys Tyr Ile
465                 470                 475                 480

Leu Gly Gln Arg Leu Glu Glu Leu Asp Trp Met Asp Ala Glu Thr Arg
            485                 490                 495

Ala Ala Ala Arg Ala Lys Leu Gln Tyr Met Met Val Met Val Gly Tyr
            500                 505                 510

Pro Asp Phe Leu Leu Lys Pro Asp Ala Val Asp Lys Glu Tyr Glu Phe
            515                 520                 525

Glu Val His Glu Lys Thr Tyr Phe Lys Asn Ile Leu Asn Ser Ile Arg
530                 535                 540

Phe Ser Ile Gln Leu Ser Val Lys Lys Ile Arg Gln Glu Val Asp Lys
545                 550                 555                 560

Ser Thr Trp Leu Leu Pro Pro Gln Ala Leu Asn Ala Tyr Tyr Leu Pro
            565                 570                 575

Asn Lys Asn Gln Met Val Phe Pro Ala Gly Ile Leu Gln Pro Thr Leu
            580                 585                 590

Tyr Asp Pro Asp Phe Pro Gln Ser Leu Asn Tyr Gly Gly Ile Gly Thr
            595                 600                 605

Ile Ile Gly His Glu Leu Thr His Gly Tyr Asp Asp Trp Gly Gly Gln
610                 615                 620

Tyr Asp Arg Ser Gly Asn Leu Leu His Trp Trp Thr Glu Ala Ser Tyr
625                 630                 635                 640

Ser Arg Phe Leu Arg Lys Ala Glu Cys Ile Val Arg Leu Tyr Asp Asn
            645                 650                 655

Phe Thr Val Tyr Asn Gln Arg Val Asn Gly Lys His Thr Leu Gly Glu
            660                 665                 670

Asn Ile Ala Asp Met Gly Gly Leu Lys Leu Ala Tyr His Ala Tyr Gln
            675                 680                 685

Lys Trp Val Arg Glu His Gly Pro Glu His Pro Leu Pro Arg Leu Lys
            690                 695                 700

Tyr Thr His Asp Gln Leu Phe Phe Ile Ala Phe Ala Gln Asn Trp Cys
705                 710                 715                 720

Ile Lys Arg Arg Ser Gln Ser Ile Tyr Leu Gln Val Leu Thr Asp Lys
            725                 730                 735

His Ala Pro Glu His Tyr Arg Val Leu Gly Ser Val Ser Gln Phe Glu
            740                 745                 750

Glu Phe Gly Arg Val Leu His Cys Pro Lys Val Ser Pro Met Asn Pro
            755                 760                 765

Ala His Lys Cys Ser Val Trp
            770                 775
```